(12) United States Patent
Tegels et al.

(10) Patent No.: US 9,241,694 B2
(45) Date of Patent: Jan. 26, 2016

(54) BIOADHESIVE DELIVERY SYSTEMS AND METHODS FOR VASCULAR CLOSURE

(71) Applicant: ST. JUDE MEDICAL PUERTO RICO LLC, Caguas, PR (US)

(72) Inventors: Zachary J. Tegels, Minneapolis, MN (US); Robert M. Vidlund, Forest Lake, MN (US); Douglas P. Killion, Maple Grove, MN (US); Martha Escobar, Jordan, MN (US); Khoi Le, Excelsior, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 154 days.

(21) Appl. No.: 13/773,334

(22) Filed: Feb. 21, 2013

(65) Prior Publication Data

US 2014/0236225 A1    Aug. 21, 2014

(51) Int. Cl.
*A61B 17/08* (2006.01)
*A61D 1/00* (2006.01)
*A61B 17/00* (2006.01)

(52) U.S. Cl.
CPC ....... *A61B 17/00491* (2013.01); *A61B 17/0057* (2013.01); *A61B 2017/0065* (2013.01); *A61B 2017/00654* (2013.01); *A61B 2017/00672* (2013.01)

(58) Field of Classification Search
CPC ..................................................... A61B 17/08
USPC .................. 606/108, 191, 194, 198, 200, 213; 604/57, 502, 15, 48
See application file for complete search history.

(56) References Cited

U.S. PATENT DOCUMENTS

| 5,486,195 | A  | * | 1/1996 | Myers et al. ................... 606/213 |
| 2008/0109029 | A1 | * | 5/2008 | Gurm ............................. 606/194 |
| 2008/0249519 | A1 | * | 10/2008 | Goldman et al. ............... 606/27 |
| 2010/0211000 | A1 | * | 8/2010 | Killion et al. ................... 604/57 |
| 2011/0166595 | A1 |   | 7/2011 | Vidlund |
| 2012/0016344 | A1 | * | 1/2012 | Kusakabe ...................... 604/528 |
| 2013/0190808 | A1 |   | 7/2013 | Tegels et al. |
| 2013/0190812 | A1 |   | 7/2013 | Vidlund et al. |

FOREIGN PATENT DOCUMENTS

WO    2010027693 A2    3/2010

OTHER PUBLICATIONS

PCT International Search Report for PCT International Application No. PCT/US2013/069616, mailed Feb. 18, 2014. (5 pp.).

* cited by examiner

*Primary Examiner* — Katherine M Shi
*Assistant Examiner* — Mohamed Gabr
(74) *Attorney, Agent, or Firm* — Holland & Hart

(57) ABSTRACT

A vascular closure system includes a balloon location device, a bioadhesive delivery device, and a sealing tip. The balloon location device includes a balloon for temporarily sealing a vessel puncture internally and at least one lumen for delivering inflation fluid to the balloon. The bioadhesive delivery device includes at least one lumen for delivery of the balloon location device to the vessel puncture. One of the balloon location device and the bioadhesive delivery device includes a first lumen for delivery of a first volume of bioadhesive to the vessel puncture. The sealing tip is releasable within a channel formed in the first volume of bioadhesive upon withdrawal of the balloon. One of the balloon location device and the bioadhesive delivery device is configured for delivery of a second volume of bioadhesive to the vessel puncture after the sealing tip is released in the channel.

13 Claims, 49 Drawing Sheets

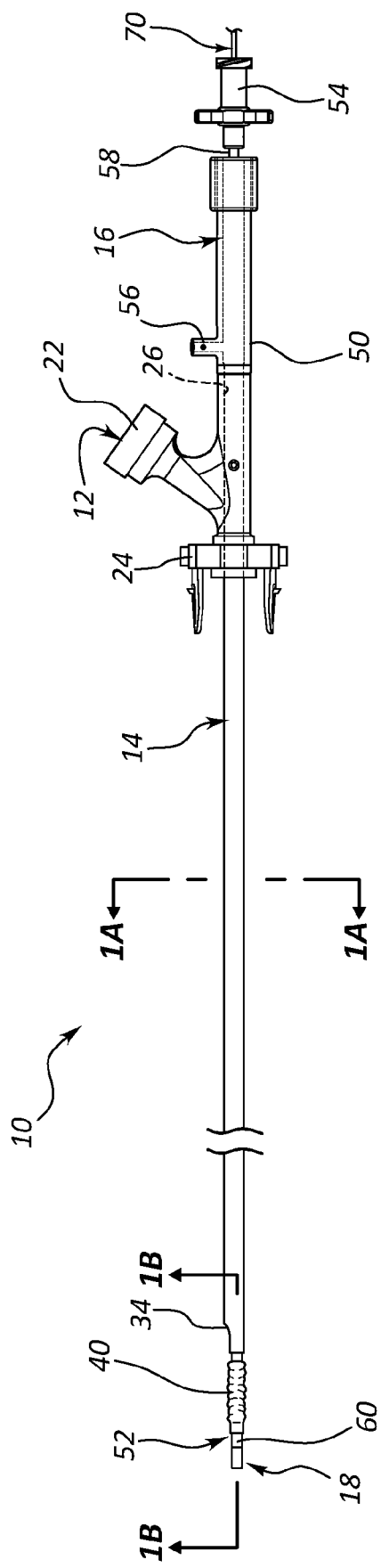
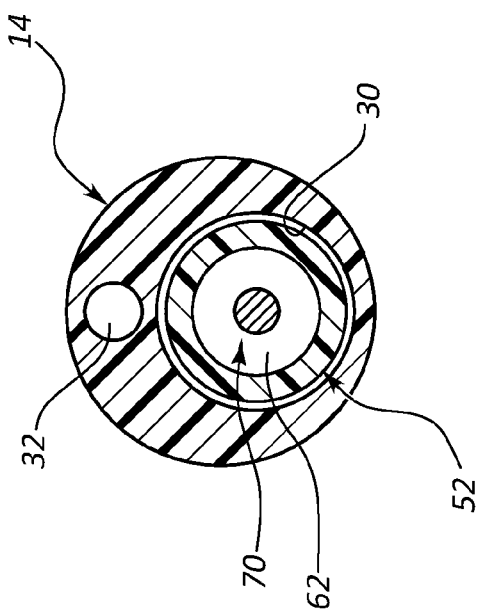
FIG. 1
FIG. 1A

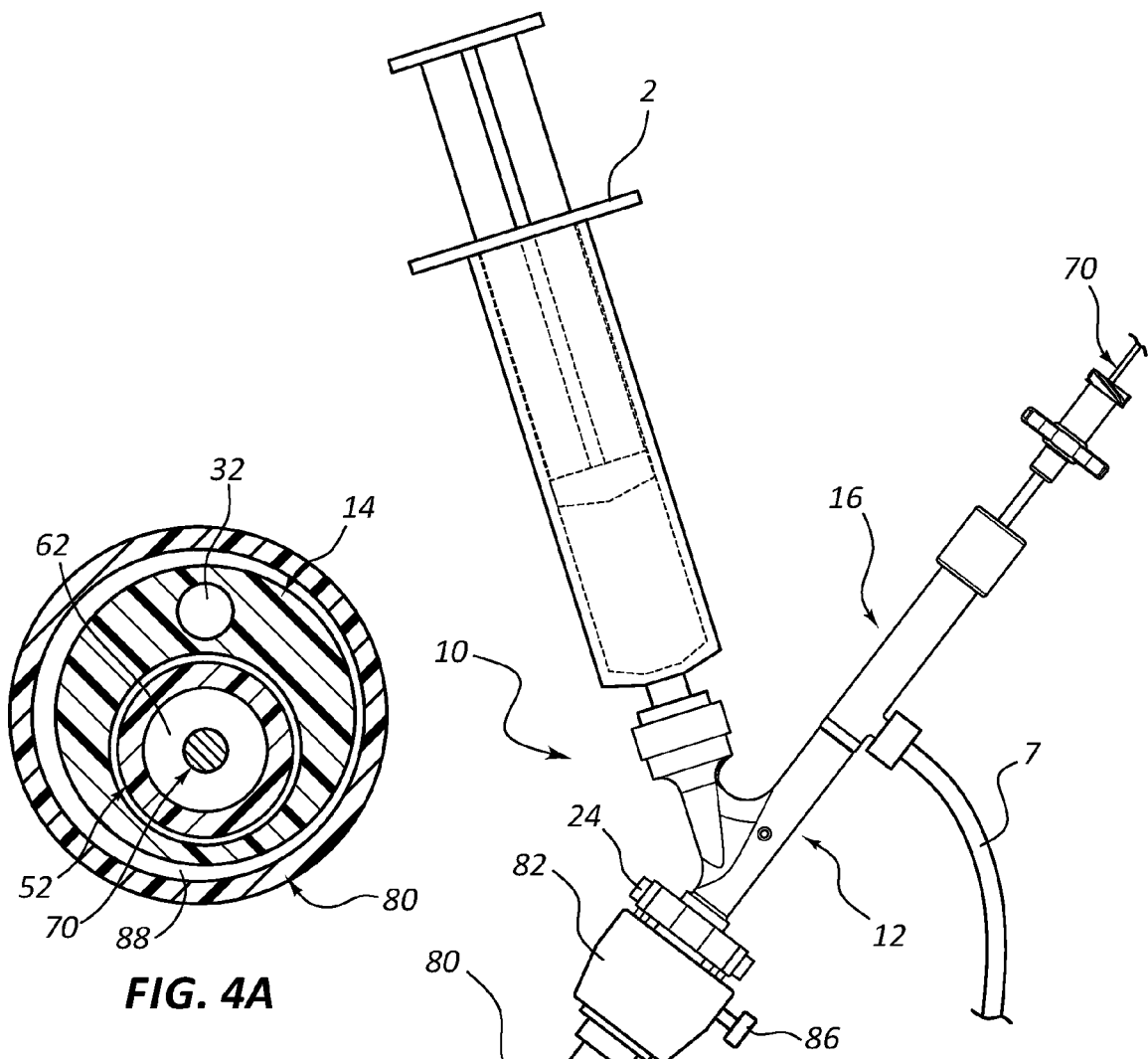
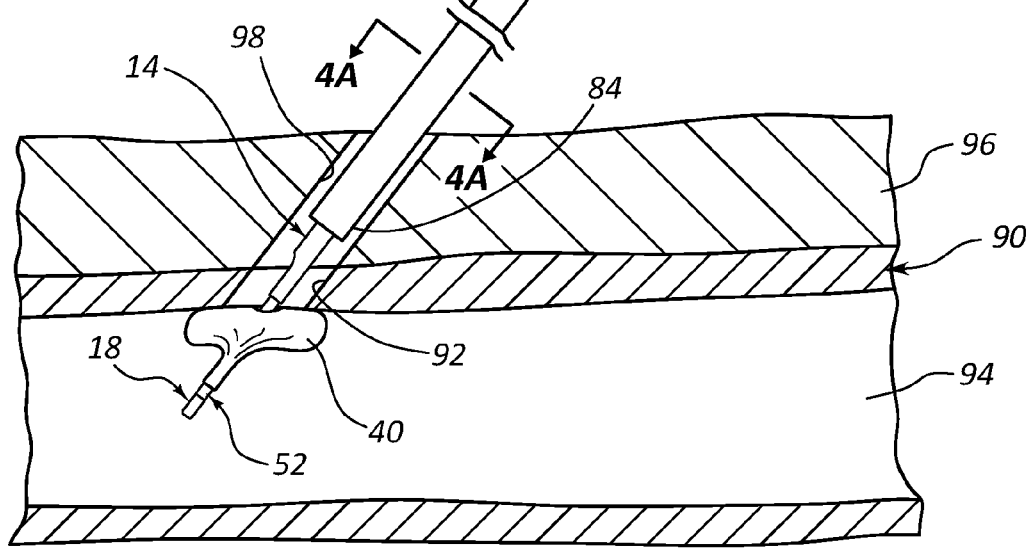
FIG. 4A
FIG. 4

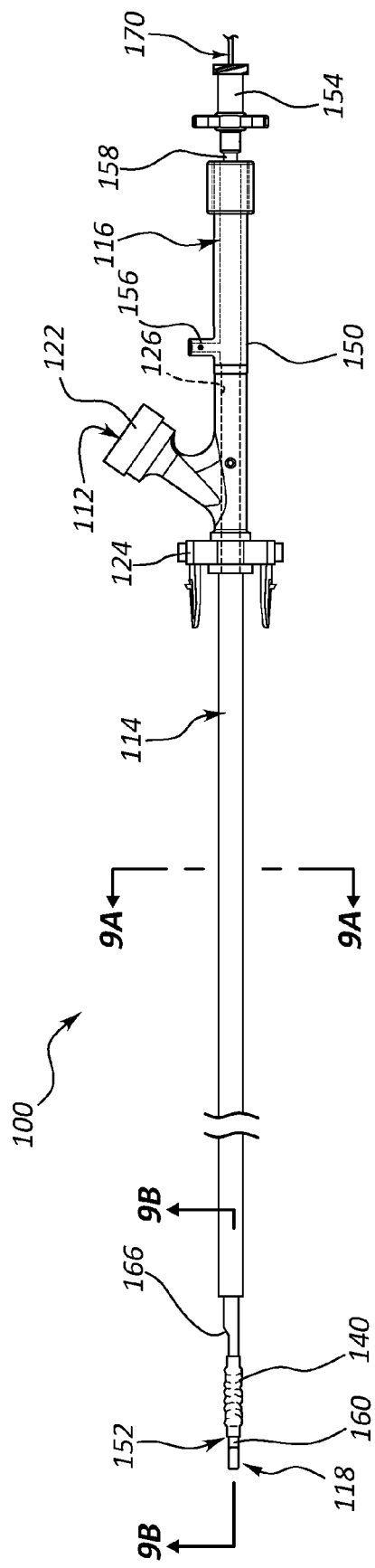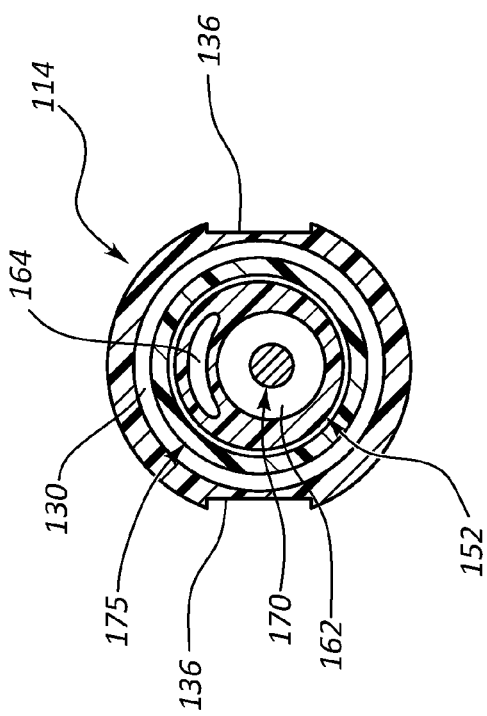
FIG. 9
FIG. 9A

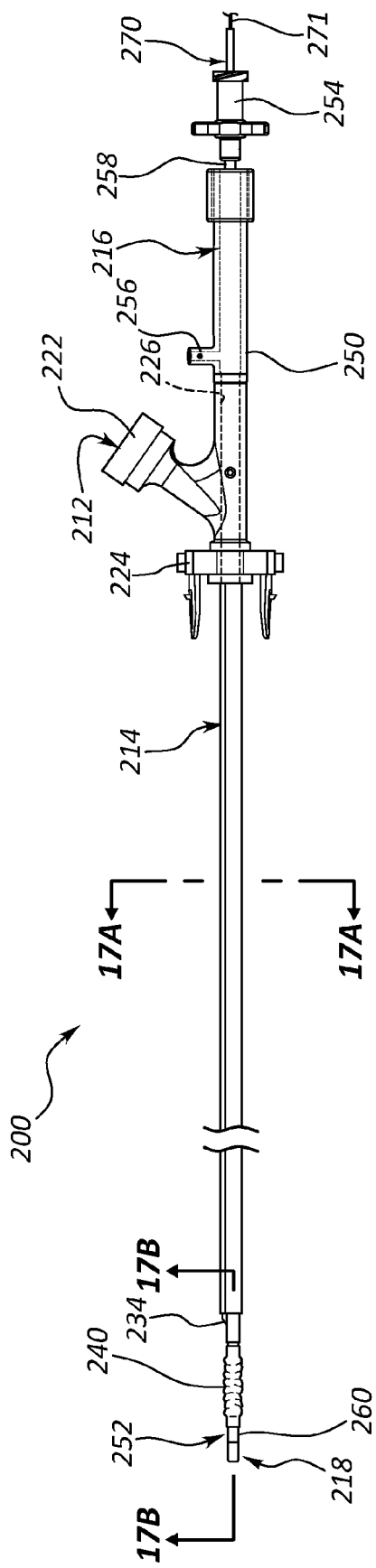
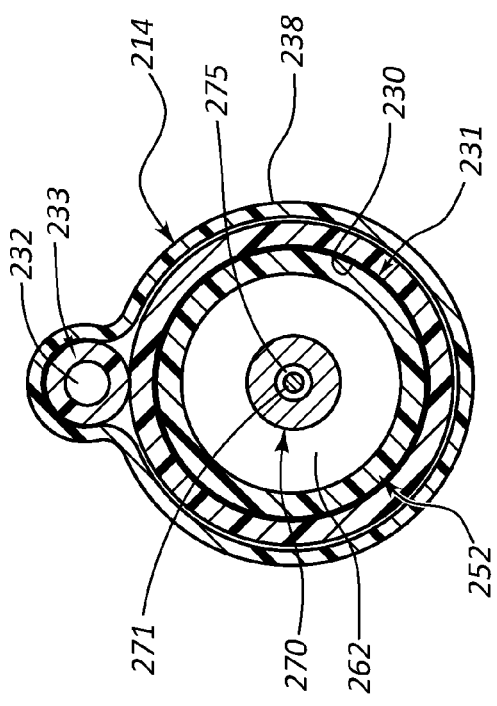
FIG. 17
FIG. 17A

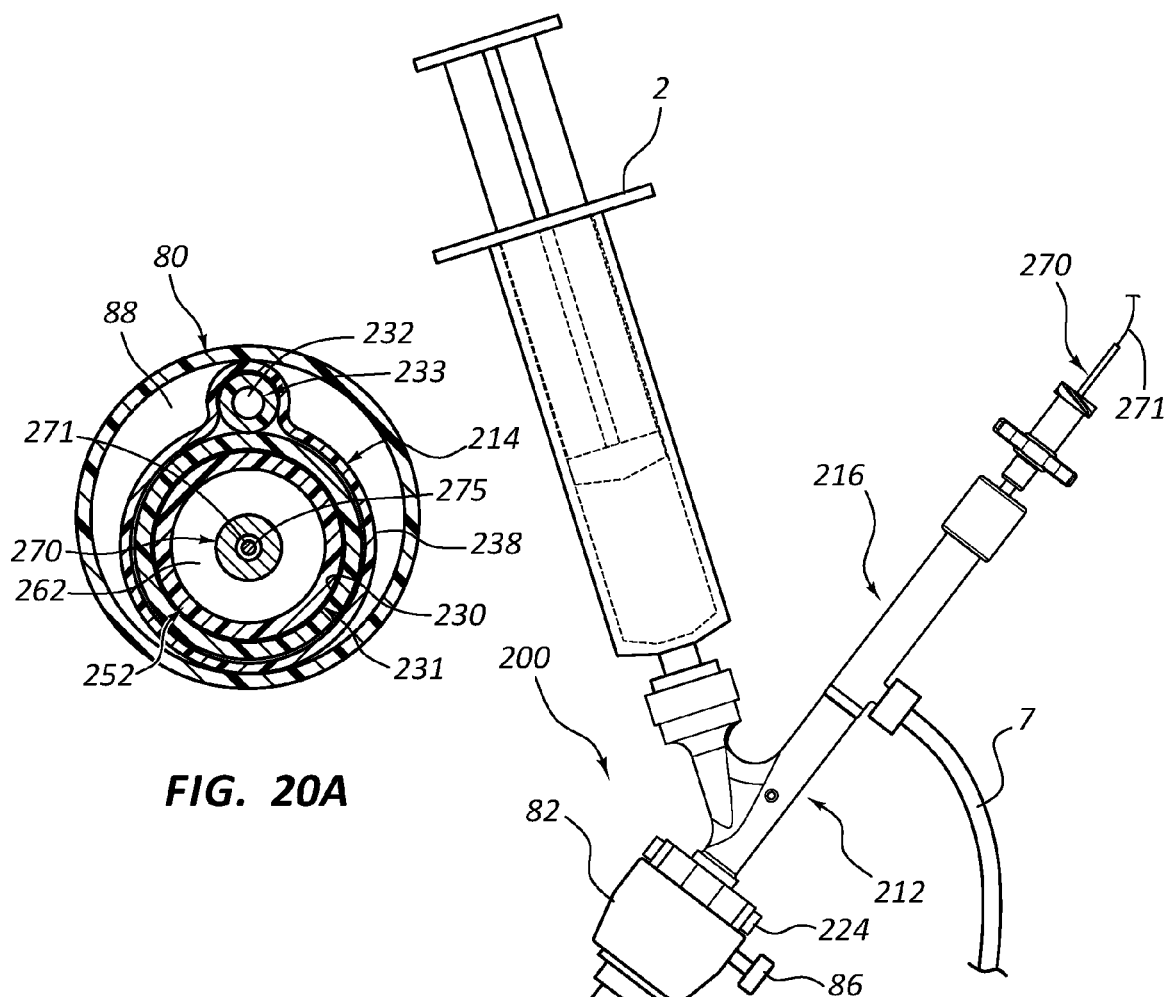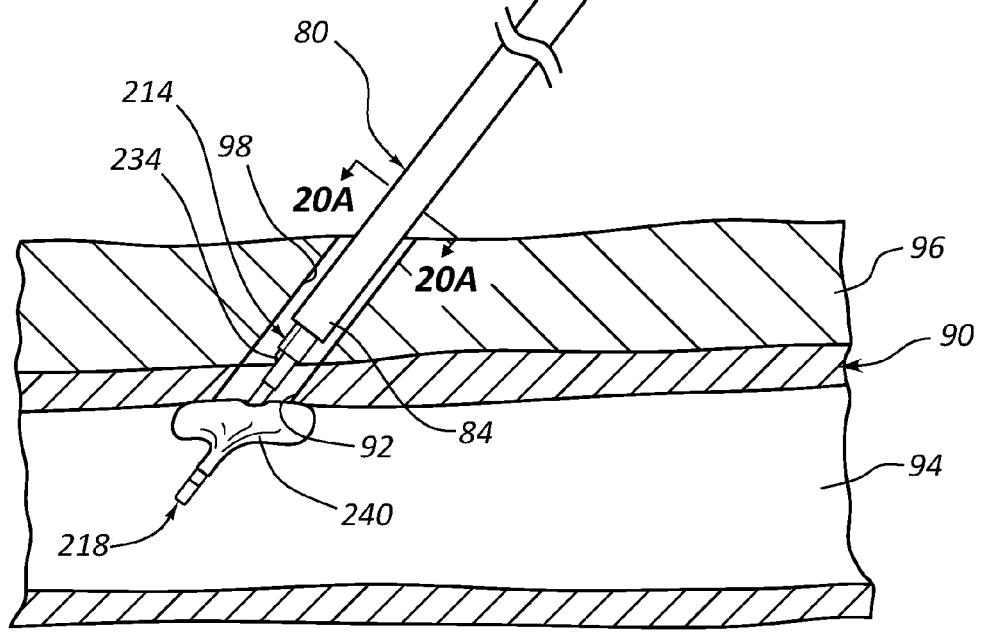
FIG. 20A
FIG. 20

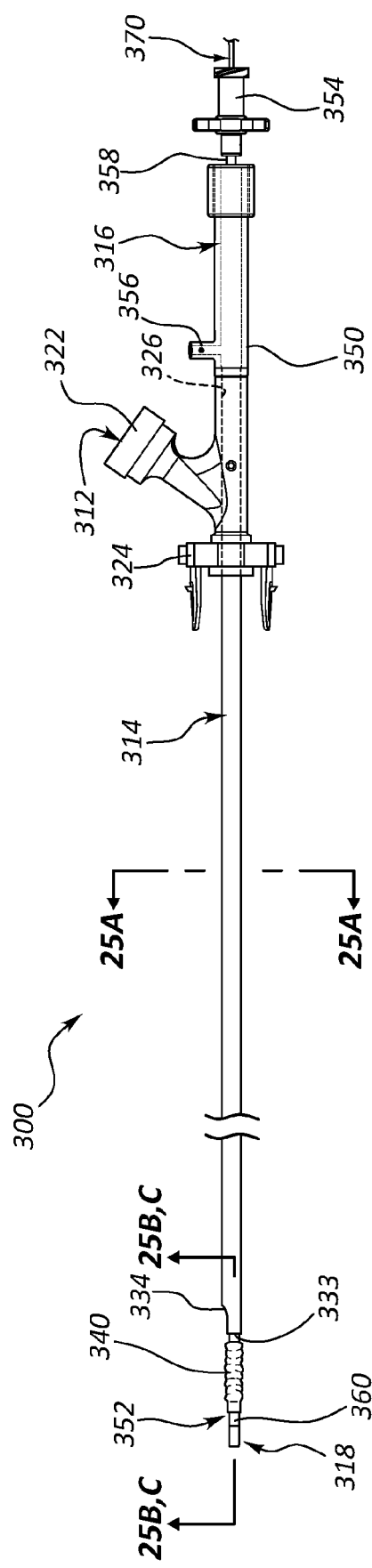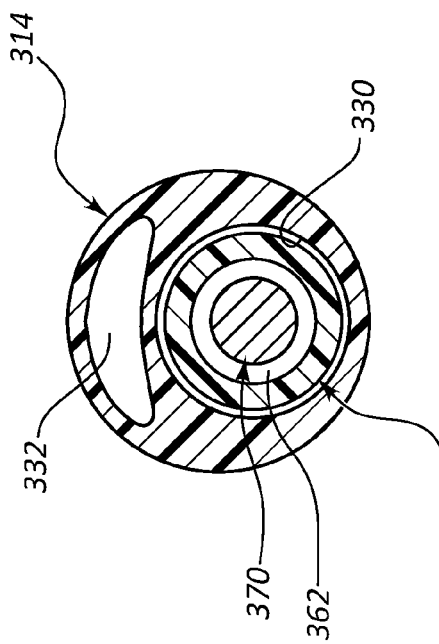
FIG. 25
FIG. 25A

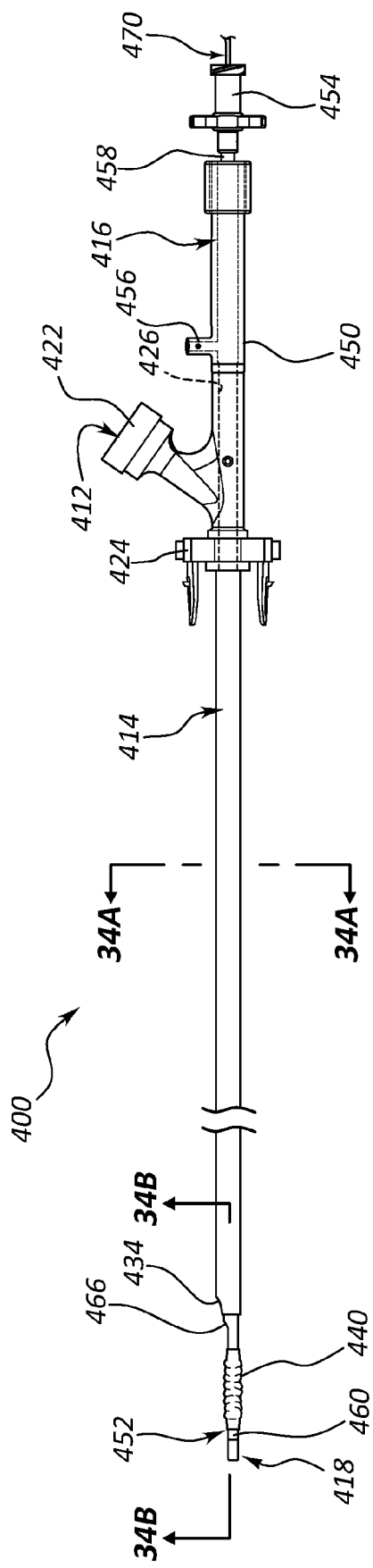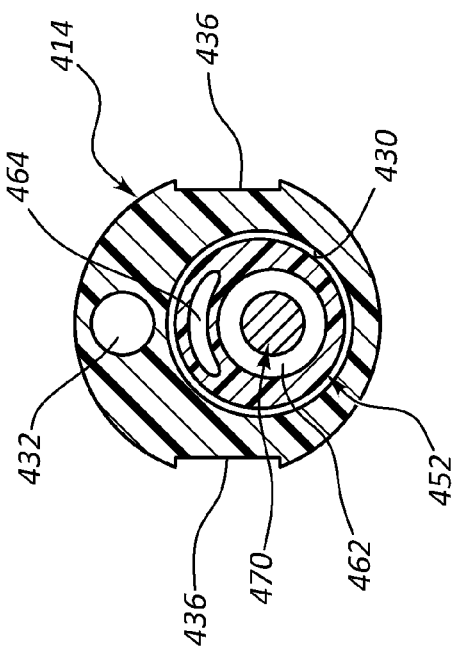
FIG. 34
FIG. 34A

US 9,241,694 B2

BIOADHESIVE DELIVERY SYSTEMS AND METHODS FOR VASCULAR CLOSURE

TECHNICAL FIELD

The present disclosure relates generally to methods and systems for sealing closed tissue punctures, and more particularly, to methods and systems for delivering bioadhesive to seal vessel punctures.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped using a vascular closure device.

While there are a variety of prior art devices and techniques for closing such punctures, one method includes temporarily sealing the tissue puncture intravascularly using an inflation balloon. A sealing material may be delivered to an outer surface of the tissue to seal the tissue puncture while maintaining the temporary seal from the balloon. Removing the collapsed balloon through the delivered sealing material may leave a tract through the sealing material. Challenges exist in closing the tract. Other challenges exist in providing multiple ejections of sealing material to the vessel puncture.

SUMMARY

One aspect of the present disclosure relates to a vascular closure system including a balloon location device, a bioadhesive delivery device, and a sealing tip. The balloon location device includes a balloon for temporarily sealing a vessel puncture internally and at least one lumen for delivering inflation fluid to the balloon. The bioadhesive delivery device includes at least one lumen for delivery of the balloon location device to the vessel puncture. One of the balloon location device and the bioadhesive delivery device includes a first lumen for delivery of a first volume of bioadhesive to the vessel puncture. The sealing tip is carried by the balloon location device at a location distal of the balloon and is releasable within a channel formed in the first volume of bioadhesive upon withdrawal of the balloon. One of the balloon location device and the bioadhesive delivery device is configured for delivery of a second volume of bioadhesive to the vessel puncture after the sealing tip is released in the channel.

The bioadhesive delivery device may include a first lumen configured to deliver the first volume of bioadhesive to the vessel puncture, and a second lumen configured for delivery of the balloon location device to the vessel puncture and for delivery of the second volume of bioadhesive to the vessel puncture after removal of the balloon location device from the second lumen. The balloon location device may include a first lumen for delivery of the inflation fluid to the balloon. The vascular closure system may further include a dilator having a lumen, and the second volume of bioadhesive may be delivered through the lumen of the dilator. The vascular closure system may further include a core wire extending through the first lumen of the balloon location device. The core wire may be connected to the sealing tip and be operable to release the sealing tip in the channel. The second volume of bioadhesive may be in direct contact with the second lumen of the bioadhesive delivery device during delivery to the vessel puncture.

The bioadhesive delivery device may include a first lumen configured to deliver the balloon location device to the vessel puncture, and to deliver the second volume of bioadhesive to the vessel puncture after removal of the balloon location device from the first lumen. The balloon location device may include a first lumen for delivery of the first volume of bioadhesive to the vessel puncture and a second lumen configured for delivery of inflation fluid to the balloon. The vascular closure system may further include a hypotube positioned in the first lumen of the bioadhesive delivery device, wherein the hypotube includes a lumen and a flared distal end, wherein the balloon location device extends through the lumen of the hypotube. The flared distal end of the hypotube may be positioned within the first lumen of the bioadhesive delivery device during delivery of the first volume of bioadhesive to block backflow of the first volume of bioadhesive into a space between the first lumen of the bioadhesive delivery device and an outer surface of the hypotube. The hypotube may be configured to advance distally to position the flared distal end out of the first lumen of the bioadhesive delivery device after delivery of the first volume of bioadhesive to permit delivery of the second volume of bioadhesive through the first lumen of the bioadhesive delivery device.

The bioadhesive delivery device may include a first lumen configured to deliver the first volume of bioadhesive to the vessel puncture, and a second lumen configured for delivery of the balloon location device to the vessel puncture, wherein the balloon location device includes a first lumen for delivery of the inflation fluid to the balloon. The first lumen may be defined by a first tube and the second lumen is defined by a second tube, wherein the first and second tubes are secured together. The vascular closure system may further include a hypotube extending through the first lumen of the balloon location device, wherein the hypotube includes a lumen for delivery of the second volume of bioadhesive. The vascular closure system may further include a filament extending through the lumen of the hypotube and connected to the sealing tip.

The bioadhesive delivery device may include a first lumen configured to deliver the first volume of bioadhesive to the vessel puncture, and a second lumen configured for delivery of the balloon location device to the vessel puncture, wherein the balloon location device defines a first lumen for delivery of the inflation fluid to the balloon and a second lumen for delivery of the second volume of bioadhesive to the vessel puncture. The bioadhesive delivery device may include a dual lumen tube defining the first and second lumens of the bioadhesive delivery device. The dual lumen tube may include at least one longitudinally extending recess formed in an outer surface thereof. The recess may define a channel when the bioadhesive delivery device is inserted through an insertion sheath for at least one of aspirating blood from the vessel puncture and providing blood flashback.

Another aspect of the present disclosure relates to a vascular closure device including a bioadhesive delivery device and a balloon location device. The bioadhesive delivery device includes at least one lumen. The balloon location device includes a balloon carried at a distal end thereof and at least one lumen. The balloon location device is insertable through the at least one lumen of the bioadhesive delivery device to position the balloon through a vessel puncture. The balloon is expandable to temporarily seal the vessel puncture internally. One of the bioadhesive delivery device and the balloon location device is configured for delivery of a first volume of bioadhesive to the vessel puncture through one of the at least one lumen, and one of the bioadhesive delivery device and the balloon location device is configured for delivery of a second volume of bioadhesive to the vessel puncture through another of the at least one lumen.

The at least one lumen of the bioadhesive delivery device may include first and second lumens, wherein the first lumen is configured for delivery of the first volume of bioadhesive, and the second lumen is receptive of the balloon location device and configured for delivery of the second volume of bioadhesive after delivery of the first volume of bioadhesive and after removal of the balloon location device. The at least one lumen of the balloon location device may include first and second lumens, wherein the first lumen is configured for delivery of inflation fluid to the balloon, and the second lumen is configured for delivery of one of the first and second volumes of bioadhesive.

The vascular closure device may further include a hypotube extending through the at least one lumen of the bioadhesive delivery device and having a lumen sized to receive the balloon location device. At least one of the first and second volumes of bioadhesive may be delivered between an outer surface of the hypotube and the lumen of the bioadhesive delivery device. The vascular closure device may further include a hypotube having a lumen and extending through the at least one lumen of the balloon location device, wherein at least one of the first and second volumes of bioadhesive is delivered through the lumen of the hypotube. The vascular closure device may further include a sealing tip carried at a distal end of the balloon location device and configured to be deposited in a channel formed in the first volume of bioadhesive after removal of the vascular closure device through the first volume of bioadhesive.

A further aspect of the present disclosure relates to a method of closing a vessel puncture in a wall of a vessel. The method includes providing a bioadhesive delivery device and a balloon location device each having at least one lumen, a balloon carried by the balloon location device, and a sealing tip carried at a distal end of the balloon location device. The method further includes advancing the balloon location device through the at least one lumen of the bioadhesive delivery device and through the vessel puncture to position the balloon within the vessel, inflating the balloon and contacting the balloon against an inner surface of the vessel to temporarily seal the vessel puncture. The method includes delivering a first volume of bioadhesive through one of the at least one lumen of the bioadhesive delivery device and the at least one lumen of the balloon location device, deflating the balloon and withdrawing the balloon through the first volume of bioadhesive, depositing the sealing tip in the first volume of bioadhesive, and delivering a second volume of bioadhesive through another one of the at least one lumen of the bioadhesive delivery device and the at least one lumen of the balloon location device at a location proximal of the first volume of bioadhesive.

The bioadhesive delivery device may include first and second lumens, wherein the first volume of bioadhesive may be delivered through the first lumen and the balloon location device is delivered through the second lumen. In another embodiment, the balloon location device may include first and second lumens, the first lumen is configured to deliver one of the first and second volumes of bioadhesive, and the second lumen is configured for delivery of inflation fluid to the balloon. The method may further include providing an insertion sheath, positioning the insertion sheath adjacent to the vessel puncture, and advancing the bioadhesive delivery device through the insertion sheath to the vessel puncture. The method may further include providing a space between an outer surface of the bioadhesive delivery device and an inner surface of the insertion sheath and conducting at least one of aspirating through the space and providing blood flashback through the space.

The method may include providing a core wire and extending the core wire through the at least one lumen of the balloon location device to stiffen the balloon location device. The method may include providing a filament, connecting the filament to the sealing tip, and extending the filament through the at least one lumen of the balloon location device.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example vascular closure device in accordance with the present disclosure.

FIG. 1A is a cross-sectional view of the vascular closure device of FIG. 1 taken along cross-section indicators 1A-1A.

FIGS. 3-8 illustrate use of the vascular closure device of FIG. 1 with a sheath to seal a vessel puncture in accordance with the present disclosure.

FIG. 9 is a side view of an example vascular closure device in accordance with the present disclosure.

FIG. 9A is a cross-sectional view of the vascular closure device of FIG. 9 taken along cross-section indicators 9A-9A.

FIG. 17 is a side view of an example vascular closure device in accordance with the present disclosure.

FIG. 17A is a cross-sectional view of the vascular closure device of FIG. 17 taken along cross-section indicators 17A-17A.

FIGS. 19-24 illustrate use of the vascular closure device of FIG. 17 with a sheath to seal a vessel puncture in accordance with the present disclosure.

FIG. 25 is a side view of an example vascular closure device in accordance with the present disclosure.

FIG. 25A is a cross-sectional view of the vascular closure device of FIG. 25 taken along cross-section indicators 25A-25A.

FIG. 34 is a side view of an example vascular closure device in accordance with the present disclosure.

FIG. 34A is a cross-sectional view of the vascular closure device of FIG. 34 taken along cross-section indicators 34A-34A.

Throughout the drawings, identical reference numbers designate similar, but not necessarily identical, elements.

DETAILED DESCRIPTION

Figure 1B:
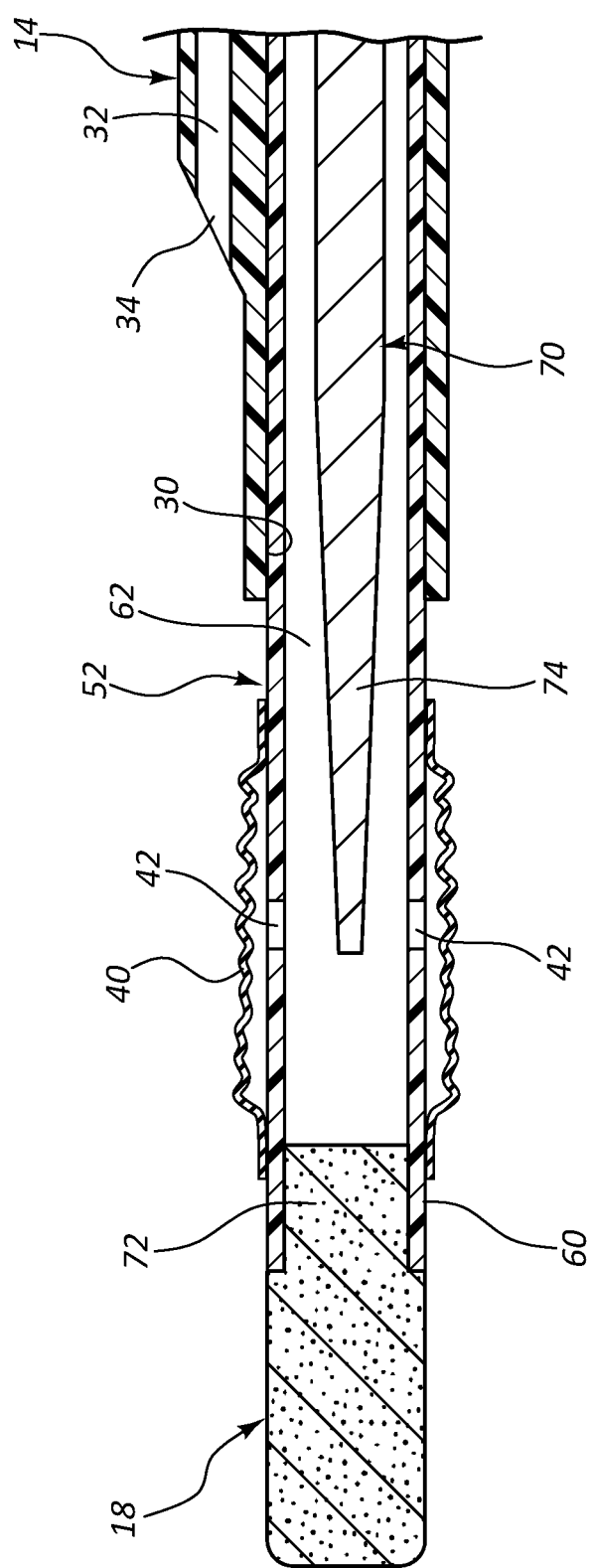
FIG. 1B is a cross-sectional view of a distal end portion of the vascular closure device of FIG. 1 taken along cross-section indicators 1B-1B.
Figure 2:
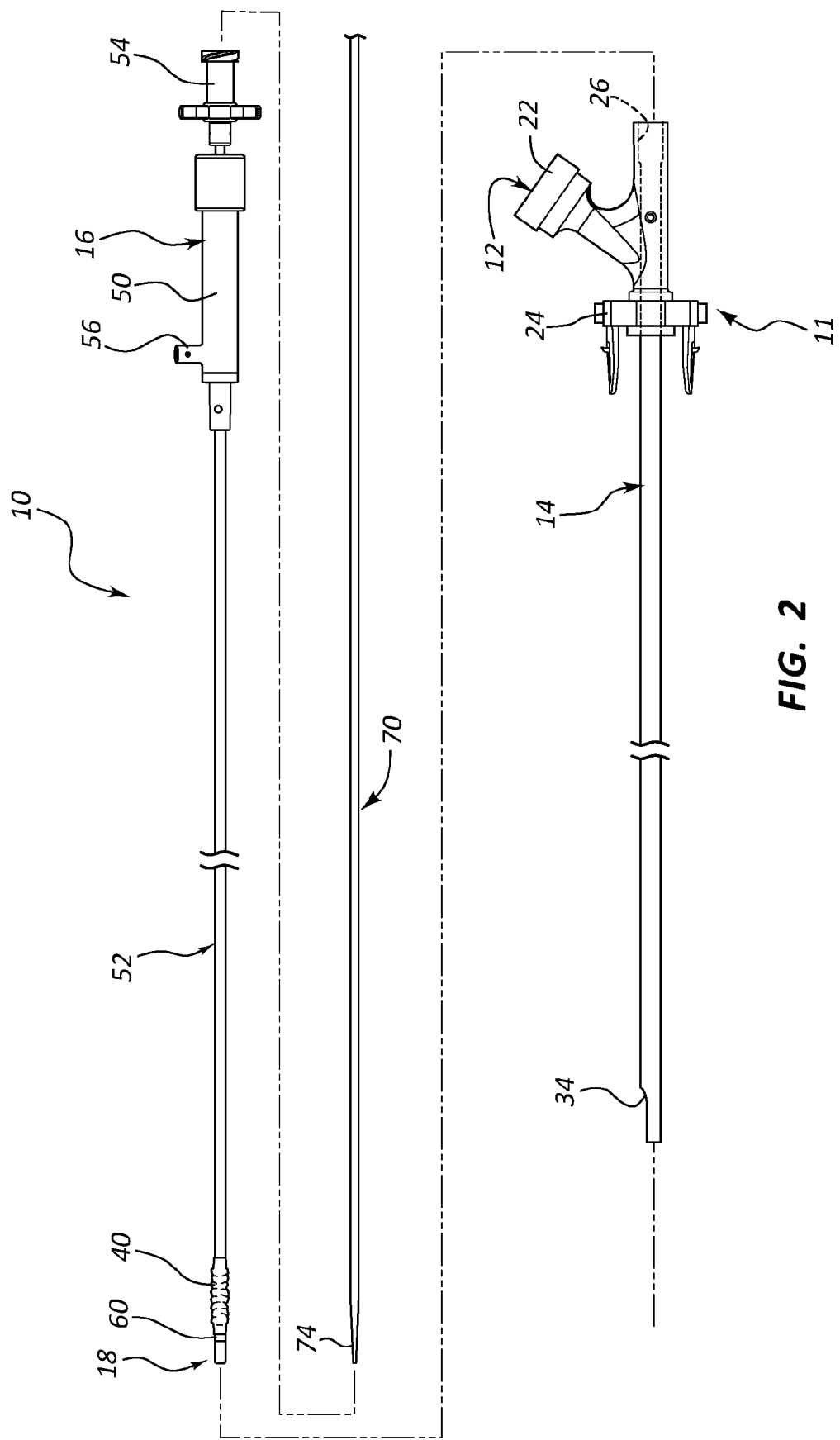
FIG. 2 is an exploded view of the vascular closure device of FIG. 1.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

An example embodiment of the present disclosure includes a vascular closure device used to deposit a volume of bioadhesive for sealing a vessel puncture. The vascular closure device may operate to deposit a single volume or multiple volumes of bioadhesive. The vascular closure device may include a detachable sealing tip. The vascular closure device is typically used with an insertion sheath that provides access through a vessel puncture and into an inner lumen of the vessel. The vascular closure device may include a bioadhesive delivery device having a delivery tube.

The delivery tube may include a single lumen or dual lumen construction. In a dual lumen construction of the delivery tube, one lumen is used to deliver bioadhesive to the tissue puncture and the other lumen is used for delivering a balloon location device to the vessel puncture. The balloon location device may include one or more lumens. In a dual lumen construction of the balloon location device, one lumen is configured for delivery of inflation fluid to a balloon carried at a distal end portion of the balloon location device, and another lumen is used for delivering bioadhesive to the vessel puncture. In some arrangements, a filament (e.g., suture) extends through a lumen of the balloon location device and is connected to the sealing tip. A core wire may extend through a lumen of the balloon location device to provide additional stiffness along a length of the balloon location device. The core wire may be connected to the sealing tip to provide a positive connection of the sealing tip to the balloon location device. The core wire may assist in depositing the sealing tip in the first volume of bioadhesive. In other arrangements, the core wire or a separate hypotube may include a lumen through which a filament extends to the sealing tip.

Typically, the sealing tip is released within the sealing material upon refraction of the vascular closure device from the vessel puncture. The sealing tip may be configured to detach from the vascular closure device within the first volume of bioadhesive after the balloon has been withdrawn through the first volume of bioadhesive. Removing the balloon through the first volume of bioadhesive may form a channel, and the sealing tip may be deposited in the channel. The second volume of bioadhesive may provide additional sealing of the channel. The second volume of bioadhesive may bond with the sealing tip to hold the sealing tip in the channel. The second volume of bioadhesive may further seal a tissue tract leading to the vessel puncture. The second volume of bioadhesive may seal the vessel puncture in general.

The example vascular closure devices disclosed herein may include different numbers of lumens and different configurations for the lumens. The lumens may be used for different purposes such as, for example, delivering a volume of bioadhesive, providing a path for delivering another object (e.g., a suture, core wire, etc.), providing blood flashback, or aspirating. The vascular closure devices disclosed herein are typically configured to deposit at least two separate volumes of bioadhesive at the vessel puncture. Typically, at least two of the lumens of the vascular closure device provide for separate delivery of the volumes of bioadhesive. The lumens may be carried either by a bioadhesive delivery device, a vessel location device of the vascular closure device, or a combination thereof.

Some lumens of the vascular closure device may have multiple purposes. For example, one lumen of the bioadhesive delivery device may be used for delivery of the balloon location device to the vessel puncture. In a later step of sealing the vessel puncture, the balloon location device may be withdrawn and that same lumen of the bioadhesive delivery device may be used for delivery of a second volume of bioadhesive, delivery of a dilator (which itself may be used for delivery of a second volume of bioadhesive), or movement of a prepositioned device such as, for example, positioning of a flared hypotube used to control backflow or delivery of one of the volumes of bioadhesive, as described below with reference to FIGS. 9-16.

Referring now to FIGS. 1-8, an example vascular closure device 10 is shown including a bioadhesive delivery device 11 (see FIG. 2), a balloon location device 16 and a detachable sealing tip 18. The bioadhesive delivery device 11 includes a manifold 12 and a delivery tube 14. The detachable sealing tip 18 may be positioned at a distal end of the balloon location device 16. The balloon location device 16 may be configured for insertion through the bioadhesive delivery device 11 to a vessel puncture as described in further detail below relating to FIGS. 3-8. Typically, the bioadhesive delivery device 11 is configured for delivery of a first volume of bioadhesive to the vessel puncture. In a further method step, the balloon location device 16 may be removed from the bioadhesive delivery device 11 and a second volume of bioadhesive is delivered either directly through a lumen of the bioadhesive delivery device 11 or through a separate device (e.g., a dilator), which is inserted through the bioadhesive delivery device 11 in place of the balloon location device 16.

The manifold 12 may include an injection port 22, a latch or connector 24, and a proximal seat 26. The delivery tube 14 may be secured to the manifold 12. A lumen of the delivery tube 14 may be arranged in flow communication with the injection port 22. Details concerning example manifolds that may be used as manifold 12 are disclosed in U.S. patent application Ser. No. 13/744,018, filed on 17 Jan. 2013, and entitled "Bioadhesive Delivery Catheter Manifold with Mixing Fixture and Methods," which application is incorporated herein in its entirety by this reference.

The latch 24 may be configured to releasably attach the vascular closure device 10 to a sheath 80 (see FIGS. 3-8) to limit axial movement of the vascular closure device 10 relative to the sheath 80. In operation, the sheath 80 may first be positioned extending through a vessel puncture and into an internal lumen of the vessel. Inserting the vascular closure device 10 through the sheath 80 and attaching a latch 24 to a hub 82 of the sheath 80 positions a balloon of the balloon location device 16 distal of a distal end 84 of the sheath 80 and within the vessel lumen.

The delivery tube 14 includes a first lumen 30 and a second lumen 32 having a distal opening 34. The first lumen 30 is connected in flow communication with the injection port 22. The second lumen 32 is open to the proximal seat 26 and arranged to receive the balloon location device 16.

The balloon location device 16 includes a balloon 40, a housing 50, an inner tube 52, an inner tube manifold 54, and an inflation manifold 56, as shown in FIG. 1. The inner tube 52 includes proximal and distal ends 58, 60 and a first lumen 62. When the bioadhesive delivery device 11 and balloon location device 16 are assembled together as shown in FIG. 1, the distal end 60 of the inner tube 52 extends distally beyond the distal most end of the delivery tube 14. The proximal end 58 of inner tube 52 extends proximal of housing 50. The inner tube manifold 54 is connected to the proximal end 58. The inflation manifold 56 may be coupled to the housing 50. The inflation manifold 56 may be in flow communication with, for example, the first lumen 62 of inner tube 52. In other arrangements, the inflation manifold 56 may be coupled in flow communication with the second lumen 32 and the second lumen 32 is coupled in flow communication with the balloon 40. FIG. 1B shows the first lumen 62 of inner tube 52 connected in flow communication with balloon 40 via inflation openings 42.

The inner tube manifold 54 may be configured for attachment to other devices such as, for example, a source of bioadhesive used as one of the first and second volumes of bioadhesive described below.

The detachable sealing tip 18 may include a proximal end 72 as shown in FIG. 1B. The proximal end 72 may extend into the first lumen 62 of inner tube 52. The remaining portions of detachable sealing tip 18 may extend distal of the inner tube 52. The detachable sealing tip 18 may have various shapes, sizes and constructions. Some example detachable sealing tips are described in U.S. patent application Ser. No. 13/744,099, filed on 17 Jan. 2013, and entitled "Bioreservable Tip with Low Force Release and Methods," which application is incorporated herein in its entirety by this reference.

The detachable sealing tip 18 may be secured to the balloon location device 16 in any desired manner. In one example, the detachable sealing tip 18 is connected to the inner tube 52 with an interference fit. The detachable sealing tip 18 may be lodged within a first volume of bioadhesive delivered to the vessel puncture and be detached from the balloon location device 16 automatically upon lodging the detachable sealing tip within a channel formed in the first volume of bioadhesive. In another example, a positive connection such as, for example, attachment via a filament maintains connection of the detachable sealing tip 18 to the balloon location device 16 until an appropriate time for release. The filament may be disconnected from the detachable sealing tip 18. Alternatively, the tension in the filament may be released thereby permitting the detachable sealing tip 18 to detach from the balloon location device 16 and be left behind as part of sealing the vessel puncture.

The vascular closure device 10 may also include a core wire 70, which extends through at least a portion of the balloon location device 16 (see FIGS. 1 and 1B). The core wire 70 may include a tapered distal portion 74 (see FIG. 1B). The core wire 70 may provide additional stiffness for the balloon location device 16 that limits kinking and undesired bending of the balloon location device 16 and vascular closure device 10 generally. A proximal end of the core wire 70 may extend proximally from the balloon location device 16. The core wire 70 may be inserted into or removed from the vascular closure device 10 as desired.

Referring now to FIGS. 3-8, the vascular closure device is shown in use with sheath 80 to seal a vessel puncture 92 and a vessel 90. The sheath 80 includes a hub 82, a distal end 84, an aspiration port 86, and an aspiration lumen 88. The aspiration lumen 88 is defined between an outer surface of the portion of the vascular closure device 10, which is positioned within the sheath 80, and an inner surface of the sheath 80 as shown in FIG. 4A. The vessel 90 includes a vessel lumen 94. The vessel puncture 92 is accessible through a tissue tract 98 of a tissue layer 96.

Figure 3:
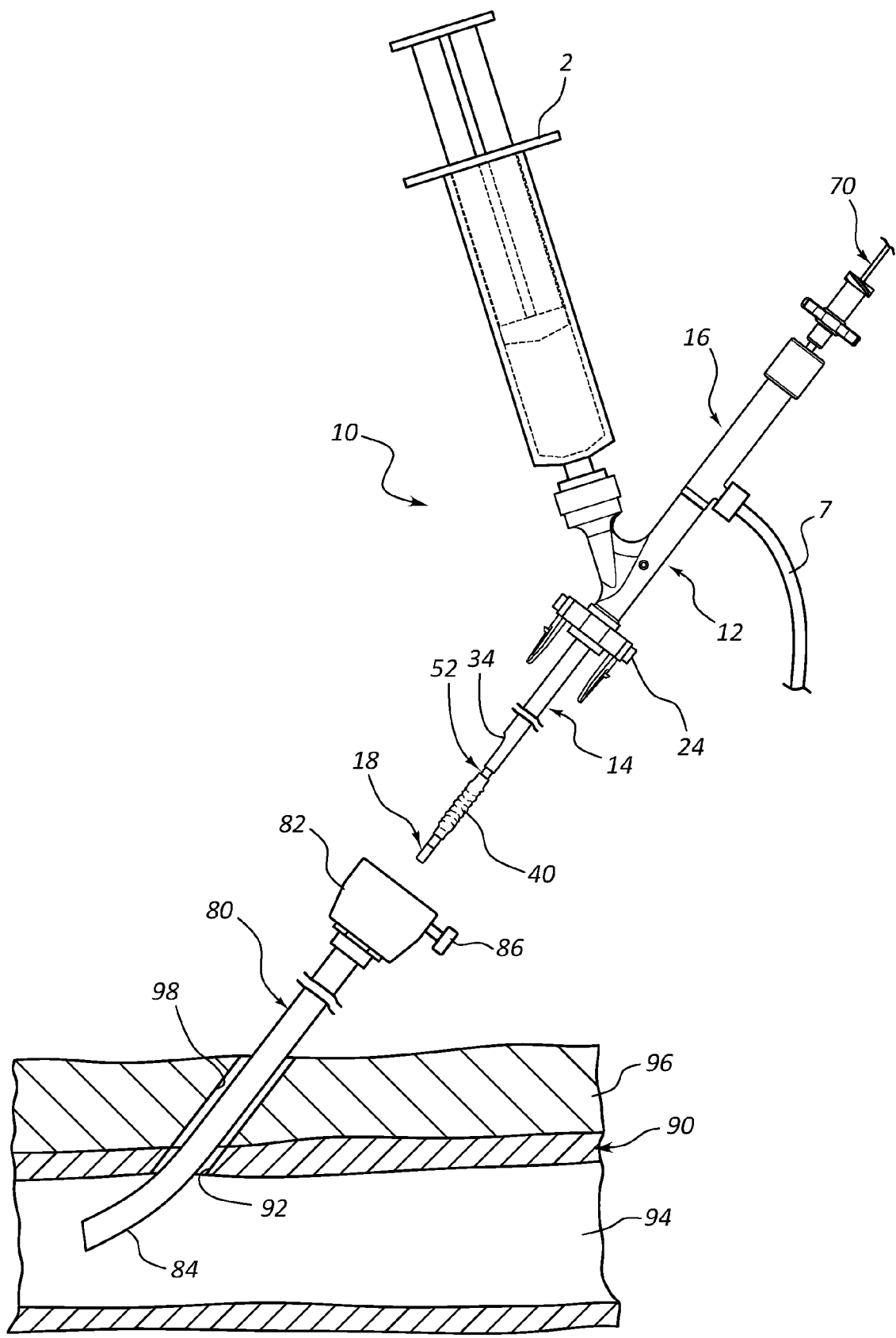

FIG. 3 shows the sheath 80 inserted through the tissue tract 98, through the vessel puncture 92, and into the vessel lumen 94. The vascular closure device 10 may be aligned with an opening into the hub 82. A first bioadhesive carrier 2 is mounted to the vascular closure device 10.

FIG. 4 shows the vascular closure device 10 inserted through the sheath 80 to position the balloon 40 within the vessel lumen 94. The latch 24 may be connected to hub 82 to provide a positive connection therebetween. A first volume of inflation fluid is delivered via inflation fluid source 7 to balloon 40 to expand balloon 40. The vascular closure device 10 and sheath 80 are withdrawn to contact the inflated balloon 40 against an inner surface of the vessel 90 to temporarily occlude blood flow through the vessel puncture 92. The area around vessel puncture 92 may be aspirated by applying a vacuum force at aspiration port 86, which draws fluids from in and around vessel puncture 92 through aspiration lumen 88 (see FIG. 4A). In some arrangements, the aspiration lumen 88 may be used as a blood flashback lumen to assist the operator in determining a position of the distal end 84 of sheath 80 relative to vessel lumen 94 prior to or after insertion of the vascular closure device 10 into sheath 80. Blood flashback may be visible at the aspiration port 86 or other location along sheath 80. Other blood flashback features may be integrated into sheath 80.

Figure 5:
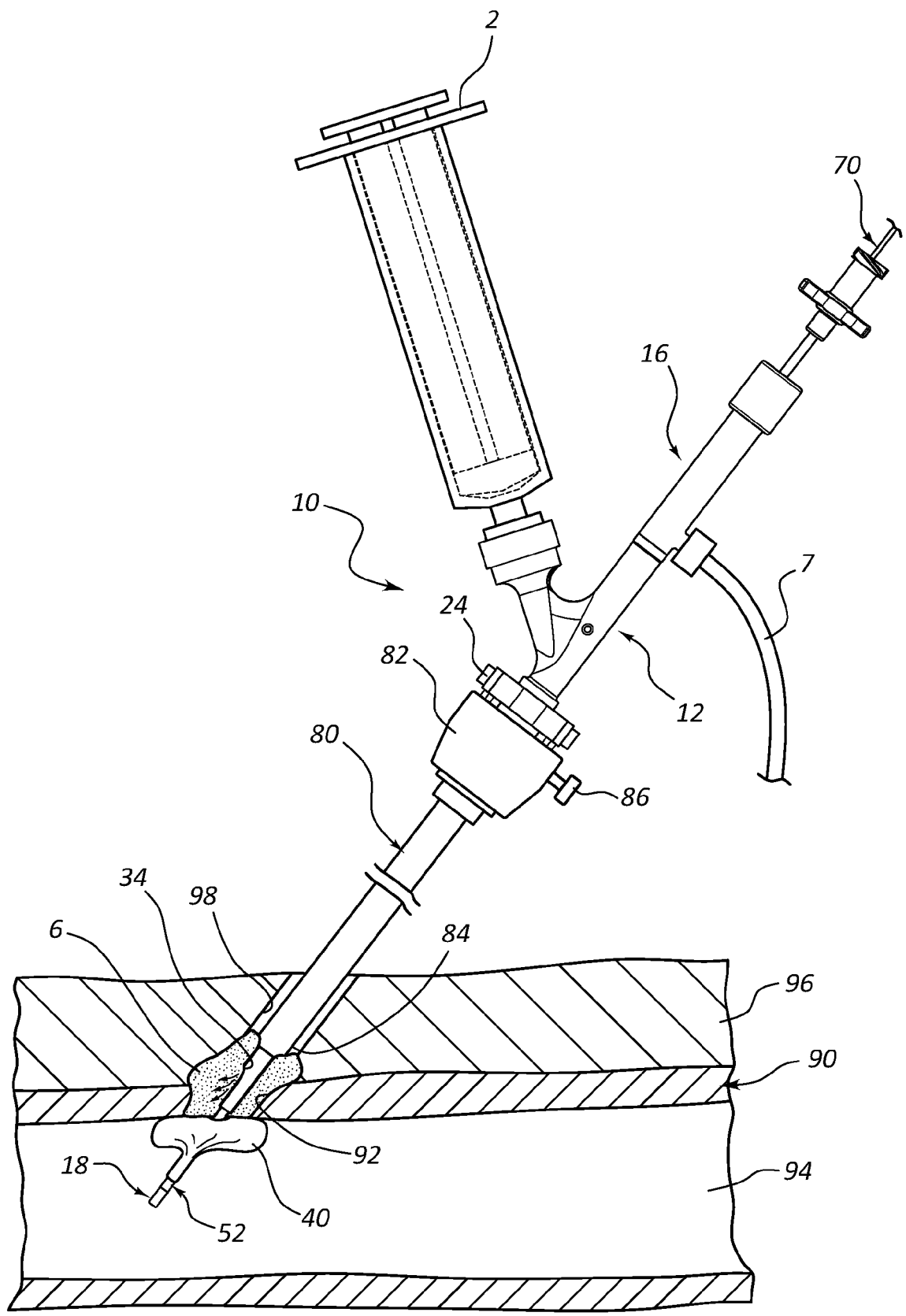

FIG. 5 shows a first volume of bioadhesive delivered through the second lumen 32 to the vessel puncture 92. The first volume of bioadhesive is expelled from the distal opening 34 of the second lumen 32. The first volume of bioadhesive may cure to form a first bioadhesive plug 6. The curing time for the first volume of bioadhesive may be in the range of about, for example, 5 seconds to about 5 minutes, and more preferably in the range of about 10 seconds to about 60 seconds. The first volume of bioadhesive is provided by operating the first bioadhesive carrier 2.

Figure 6:
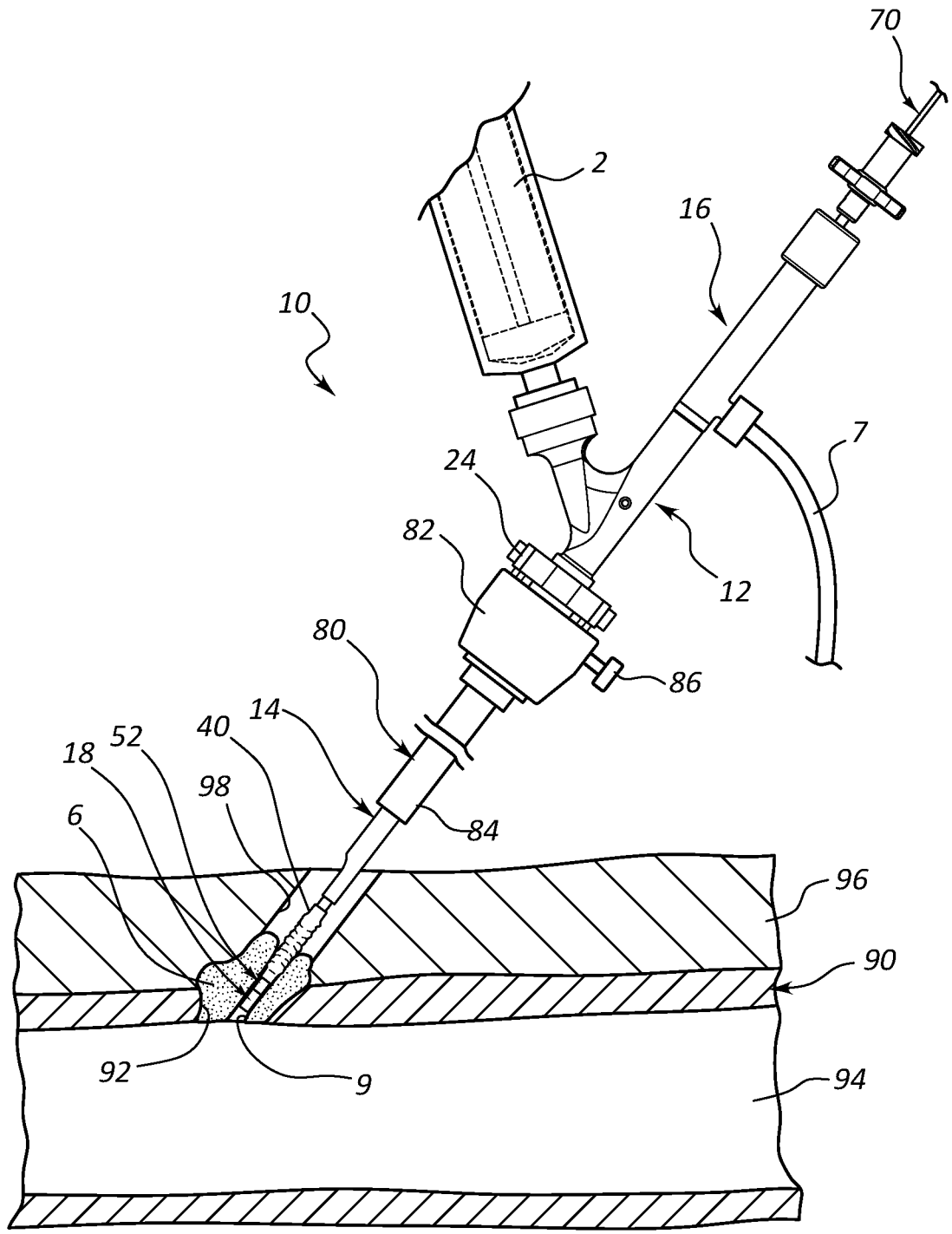

FIG. 6 shows the balloon 40 deflated and the vascular closure device 10 and sheath 80 withdrawn proximally to position the detachable sealing tip 18 in the first bioadhesive plug 6. Removing the vascular closure device 10 through the first bioadhesive plug 6 may create in a channel 9 formed in the first bioadhesive plug 6. The detachable sealing tip 18 may be positioned within the channel 9. The vascular closure device 10 may be operated to deposit the detachable sealing tip 18 within the channel 9. Various methods of detaching the detachable sealing tip 18 are possible, some of which are described with reference to other embodiments herein.

Figure 7:
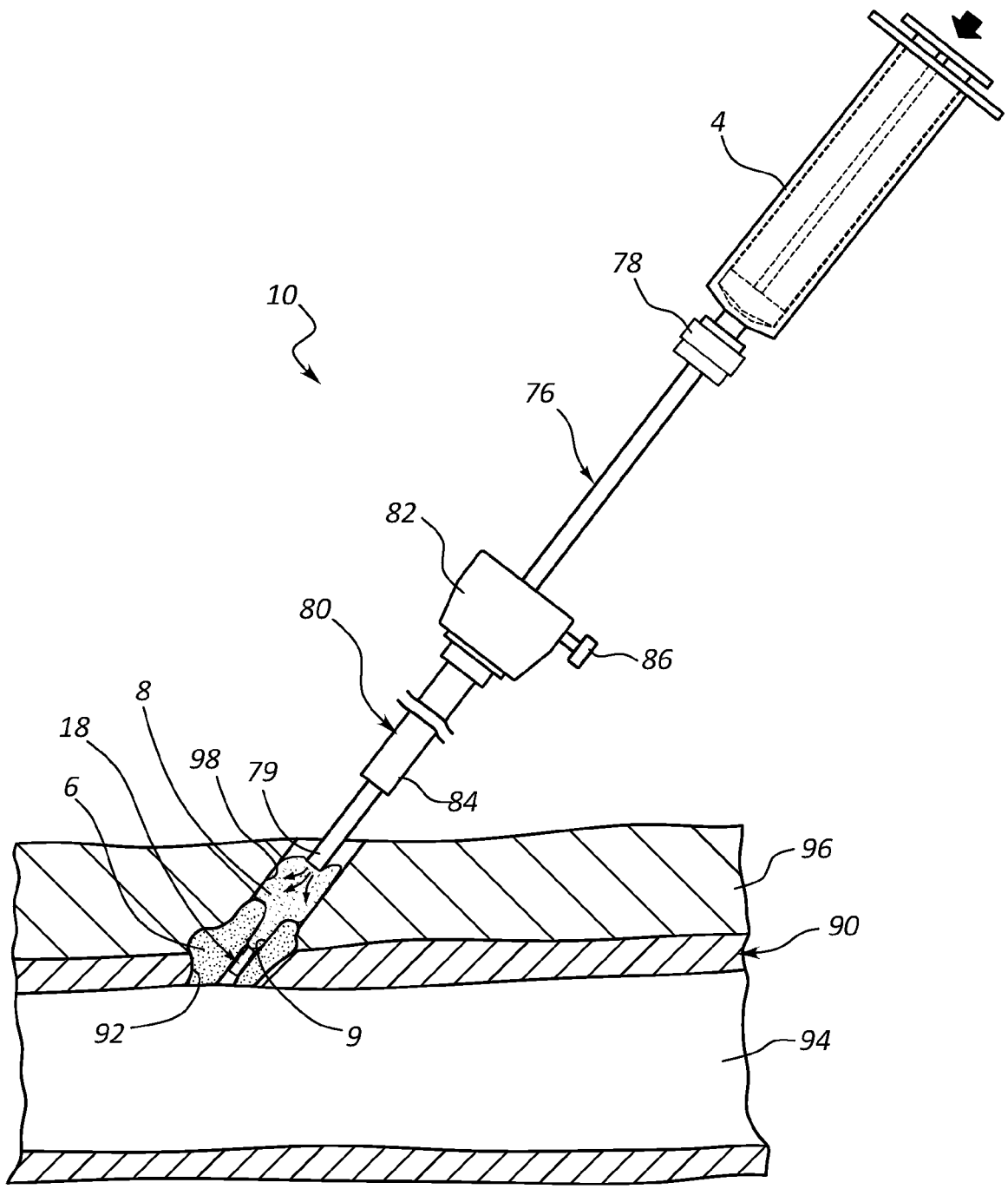
Figure 8:
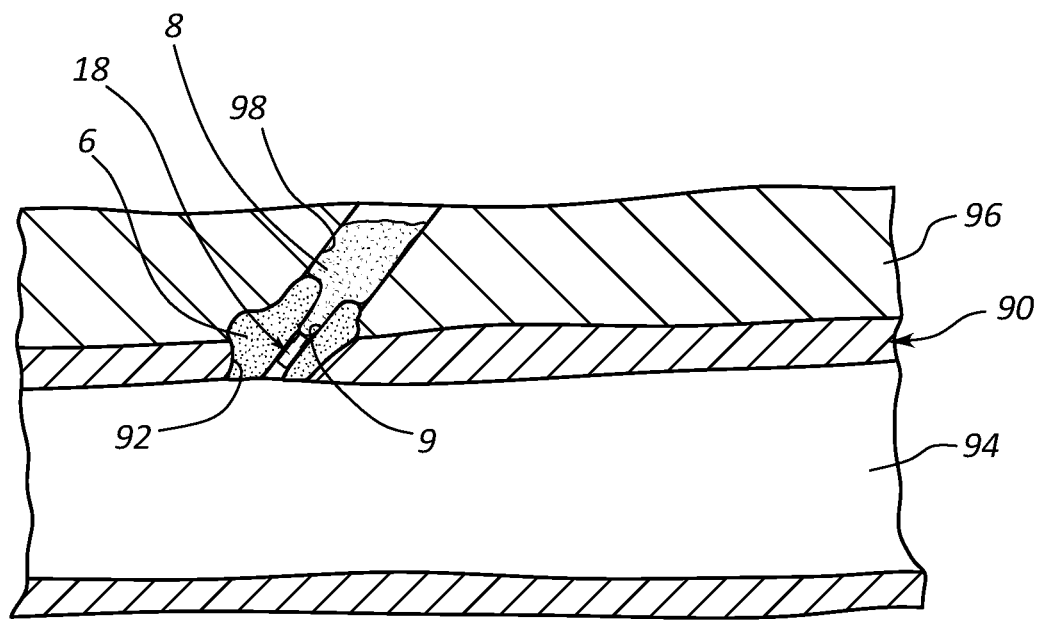

FIG. 7 shows the vascular closure device 10 removed from the sheath 80 and a separate dilator 76 is inserted through the sheath 80 to the tissue tract 98. The dilator 76 includes proximal and distal ends 78, 79. The distal end 79 is positioned within the tissue tract 98. The proximal end 78 is connected to a second bioadhesive carrier 4. The second bioadhesive carrier 4 is operated to deliver a second volume of bioadhesive into the tissue tract 98. The second volume of bioadhesive may form into a second bioadhesive plug 8, as shown in FIG. 8. The second bioadhesive plug 8 may further seal the tissue tract 98 and the vessel puncture 92. In at least some examples, portions of the second volume of bioadhesive flow into channel 9 to further seal the channel 9. The second volume of bioadhesive may also contact and bond with the detachable sealing tip 18. The connection between detachable sealing tip 18 and the second volume of bioadhesive may anchor the detachable sealing tip 18 to limit distal movement of the detachable sealing tip 18.

In other examples, after the steps shown in FIG. 6, the balloon location device 16 may be removed from the bioadhesive delivery device 11 and the dilator 76 is inserted through the first lumen 30 of the delivery tube 14 for delivery of the second volume of bioadhesive.

Referring now to FIGS. 9-16, another example vascular closure device 100 is shown including a bioadhesive delivery device 111 (see FIG. 10), a balloon location device 116 and a detachable sealing tip 118. The bioadhesive delivery device 111 includes a manifold 112 and a delivery tube 114. The balloon location device 116 is insertable through the manifold 112 and delivery tube 114 to expose a balloon 140 carried by the balloon location device 116 at a location distal of a distal end of the delivery tube 114. The detachable sealing tip 118 may be carried at the distal end of the balloon location device 116.

Figure 9B:
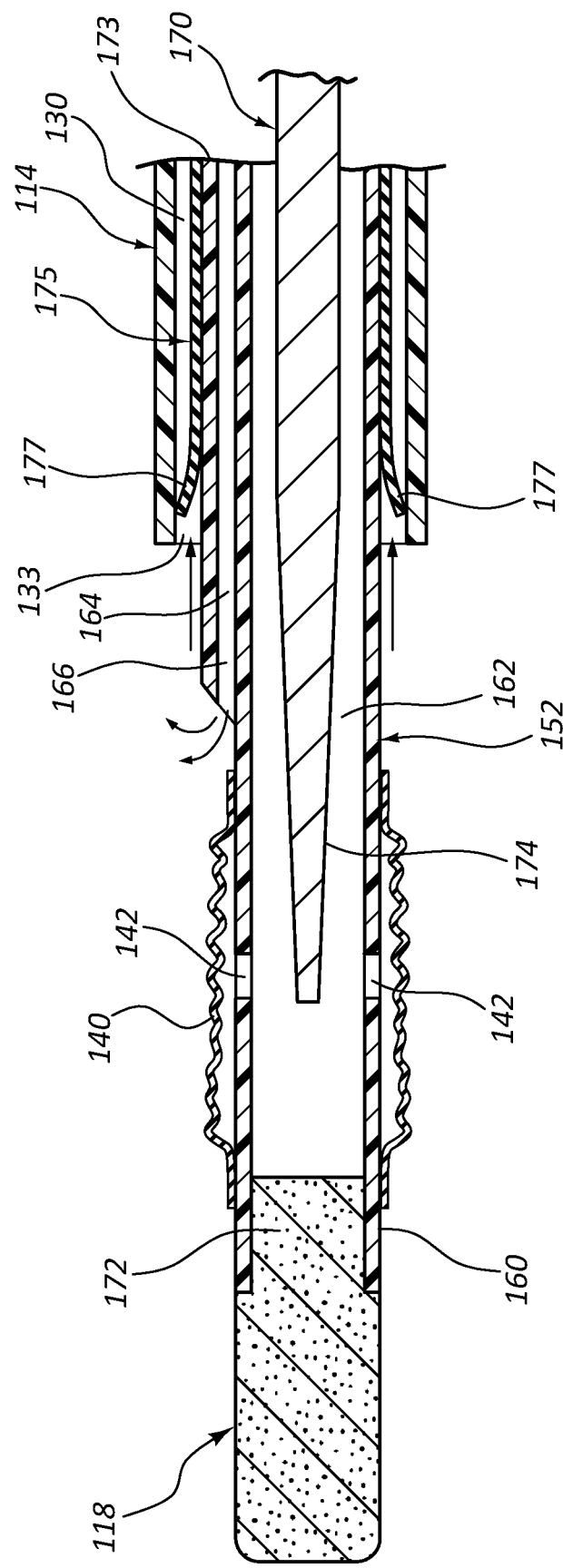
FIG. 9B is a cross-sectional view of a distal end portion of the vascular closure device of FIG. 9 taken along cross-section indicators 9B-9B.
Figures 12, 12A:
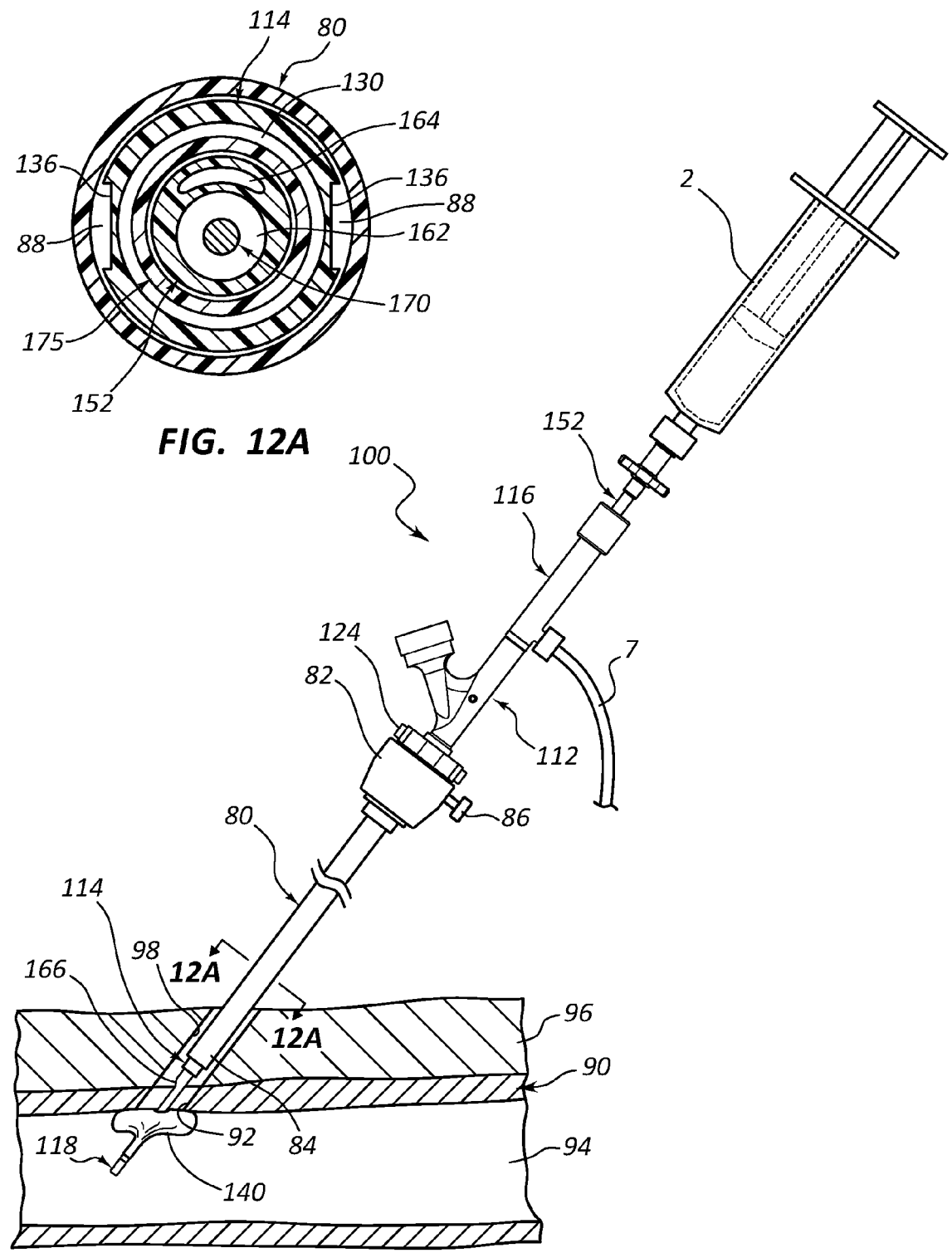

The manifold 112 may have the same or similar features to manifold 12 described above with reference to FIGS. 1-8. The manifold 112 may include an injection port 122, a latch 124, and a proximal seat 126. The delivery tube 114 may include a single lumen 130 as shown in FIGS. 9A and 9B. The lumen 130 may include a distal opening 133 (see FIG. 9B). The delivery tube 114 may include at least one cutout 136 extending longitudinally along an exterior surface thereof as shown in FIG. 9A. The cutouts 136 may provide a groove or channel that provides, for example, a pathway for aspiration or a blood flashback lumen when delivered tube 114 is inserted through sheath 80, as shown in FIG. 12A.

The balloon location device 116 includes a balloon 140, a housing 150, an inner tube 152, an inner tube manifold 154, and an inflation manifold 156. The inner tube 152 may include a plurality of inflation openings 142 that provide flow communication with the balloon 140 (see FIG. 9B). The inner tube 152 may include proximal and distal ends 158, 160, a first lumen 162, and a second lumen 164 (see FIG. 9A). The second lumen 164 may include a distal opening 166 (see FIG. 9B).

Figure 13:
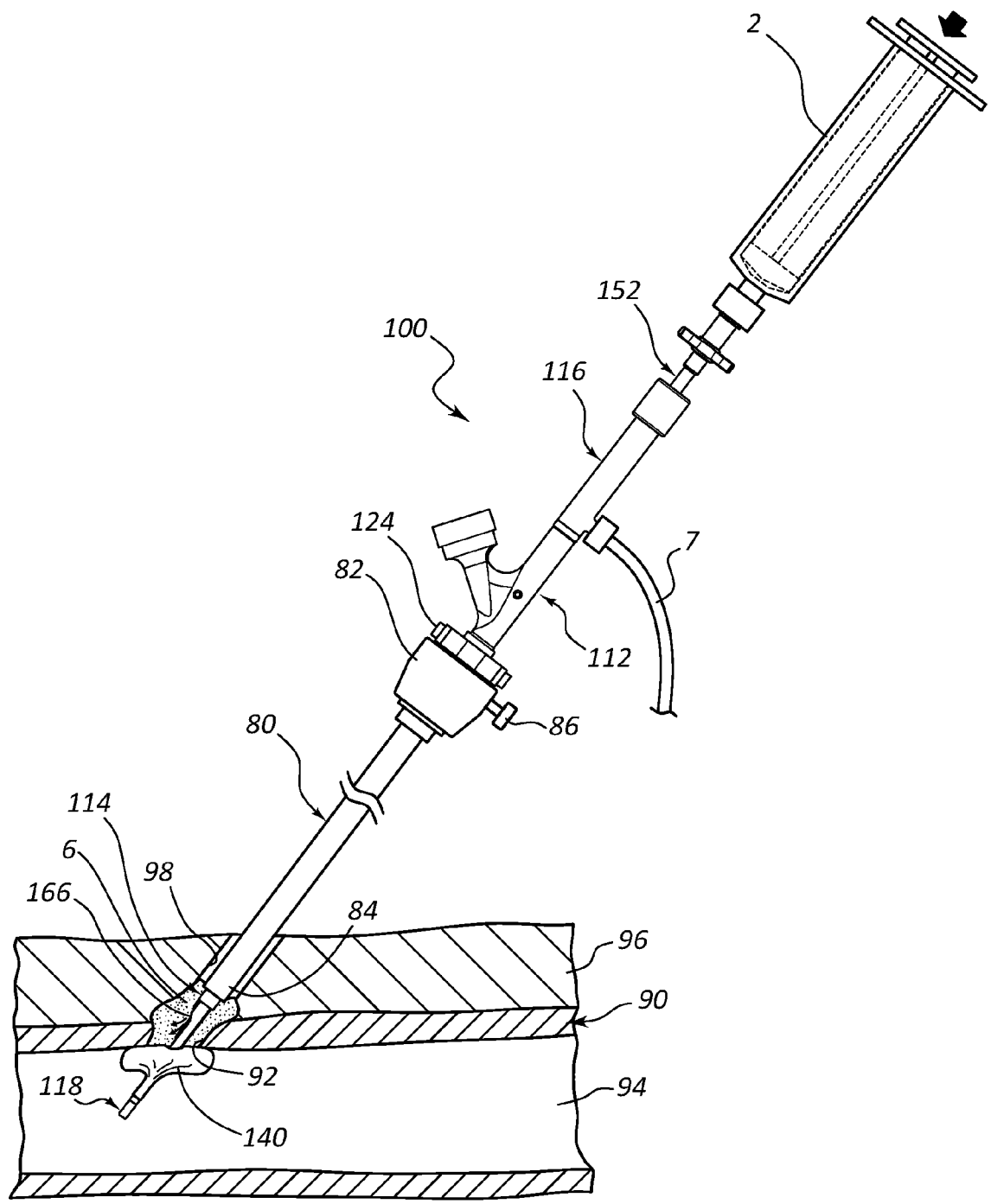

In at least one example, a first volume of bioadhesive is delivered through the second lumen 164 of the inner tube 152 as shown in FIGS. 9B and 13. In a later step, the second volume of bioadhesive is delivered through the lumen 130 of delivery tube 114 in a space between an inner surface of the delivery tube 114 and an outer surface of the balloon location device 116. In some arrangements, a separate hypotube 175 is inserted through the lumen 130. The hypotube 175 may include a flared distal end 177 and a lumen 173. The balloon location device 116 extends through the lumen 173 as shown in FIG. 9B. The flared distal end 177 may block backflow of the first volume of bioadhesive into the first lumen 130 as shown in FIG. 9B. In a later step, the hypotube 175 may be moved axially relative to the delivery tube 114 so that the flared distal end 177 no longer blocks a fluid path between the inner surface of delivery tube 114 and the outer surface of the balloon location device 116.

Figure 9C:
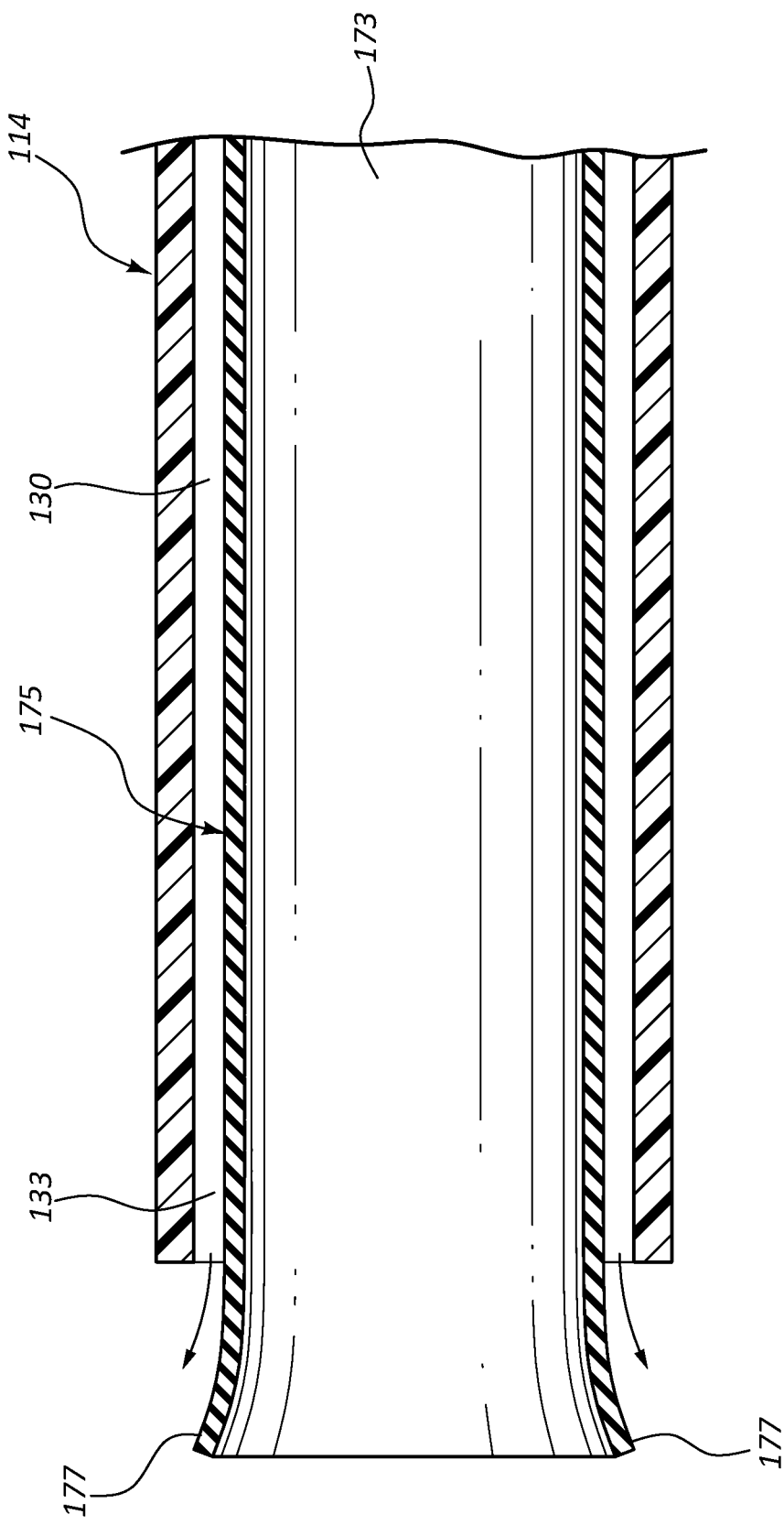
FIG. 9C is a cross-sectional view of the distal end portion of the vascular closure device of FIG. 9 with the vessel location device removed.
Figure 10:
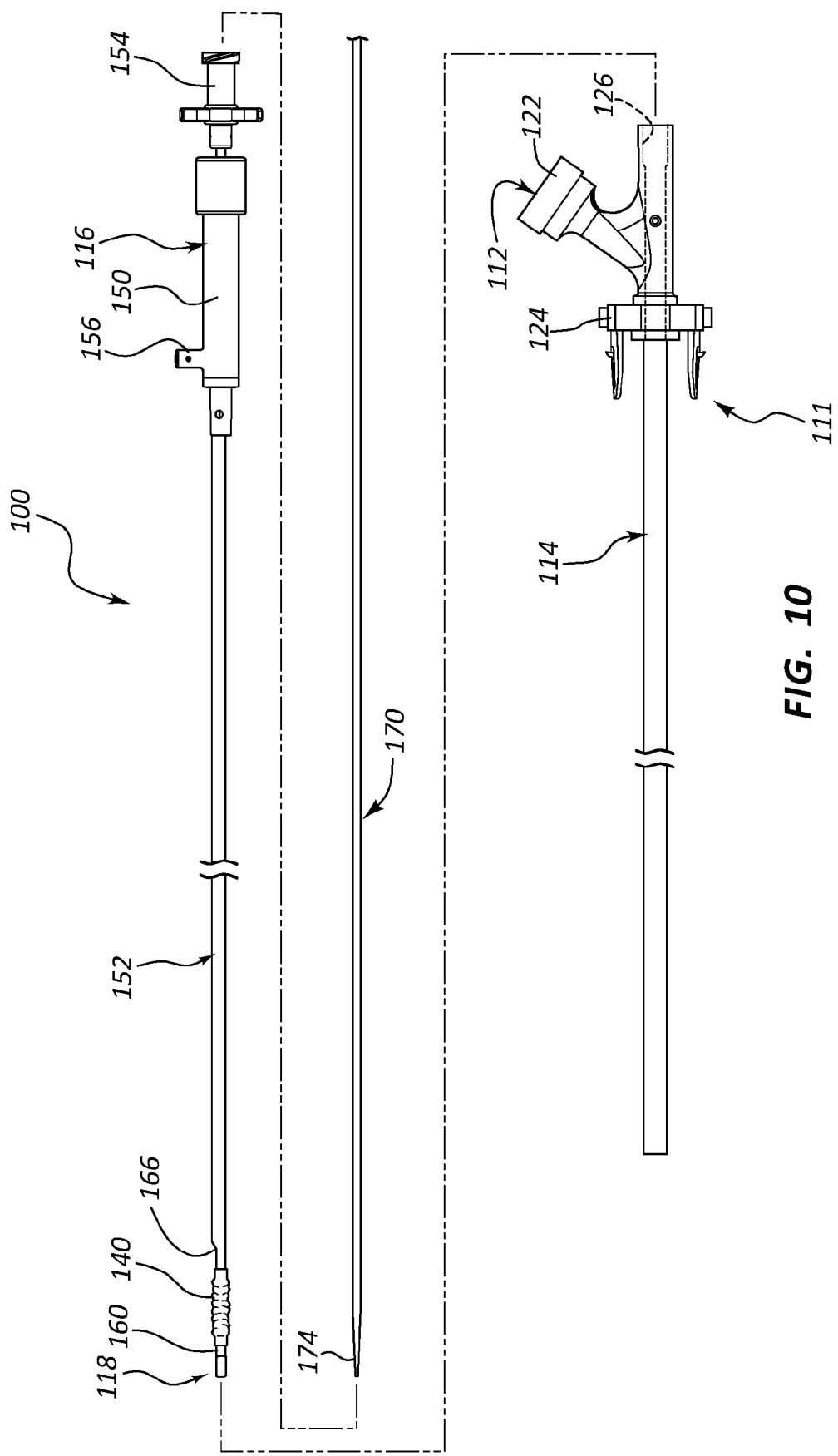
FIG. 10 is an exploded view of the vascular closure device of FIG. 9.

FIGS. 9B and 9C show a space for first lumen 130 being defined between an outer surface of hypotube 175 and the inner surface of delivery tube 114. FIG. 9C shows the hypotube 175 advanced distally so that the flared distal end 177 is removed so a second volume of bioadhesive may flow out of the distal opening 133. Advancing the hypotube 175 distally relative to delivery tube 114 may expel any portion of the first volume of bioadhesive that may have collected at the distal opening 133. The hypotube 175 may be advanced distally relative to delivery tube 114 while the balloon location device is positioned within lumen 173, or may be advanced after removal of the balloon location device 116 from the hypotube 175 as shown in FIG. 9C.

Referring to FIG. 9B, the detachable sealing tip 118 includes a proximal end 172, which may extend into the distal end 160 of the inner tube 152. A core wire 170 may extend through the first lumen 162 of the inner tube 152. The core wire 170 may provide increased stiffness and may resist kinking or bending of portions of the fastener closure device 10 such as the balloon location device 116. In some examples, the core wire 170 is connected to the detachable sealing tip 118 and may be detachable from the detachable sealing tip 118. The core wire 170 may have a tapered portion 174 at its distal end.

Figure 11:
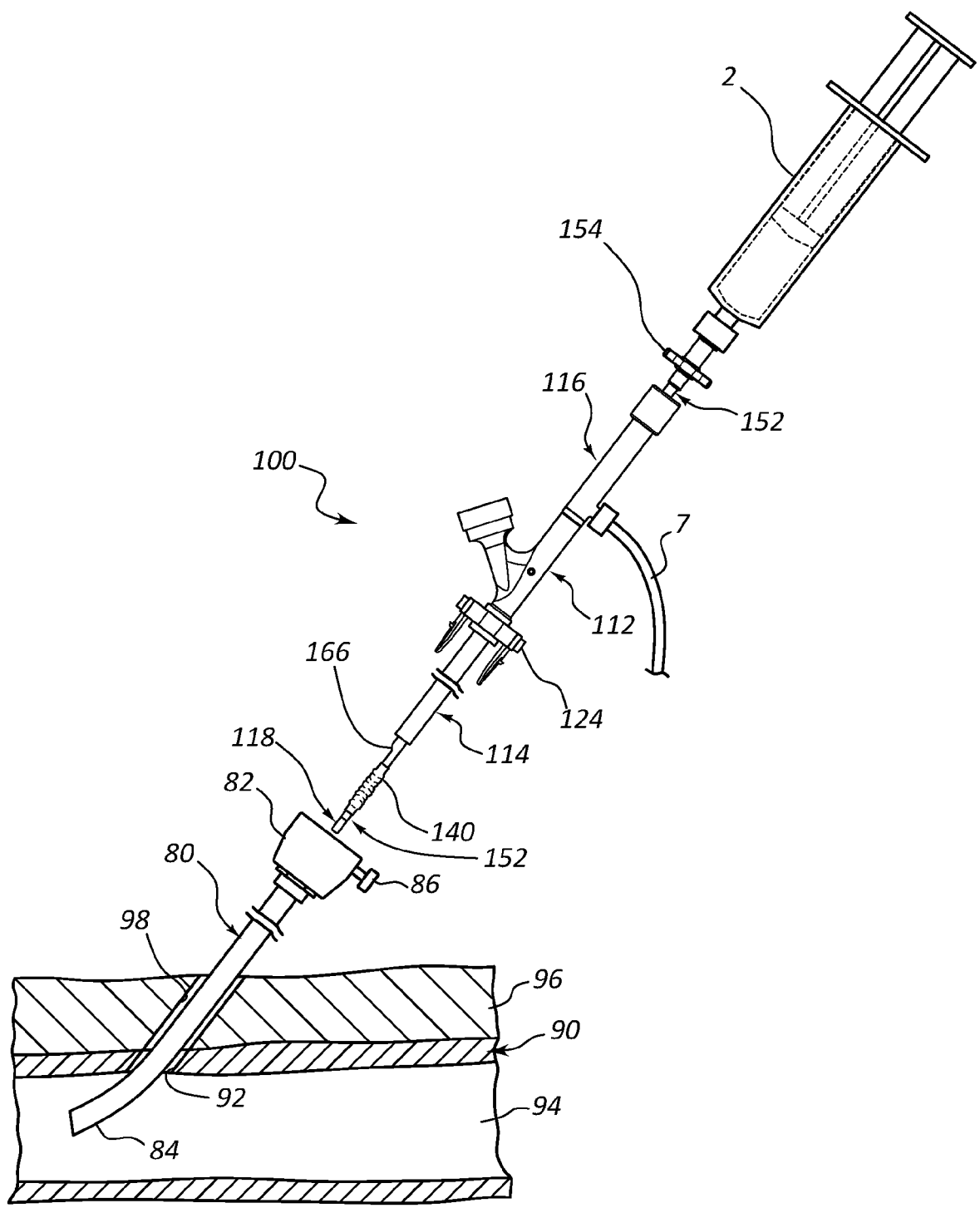
FIGS. 11-16 illustrate use of the vascular closure device of FIG. 9 with a sheath to seal a vessel puncture in accordance with the present disclosure.

Referring now to FIGS. 11-16, example steps of using vascular closure device 100 to seal vessel puncture 92 is shown and described. FIG. 11 shows the sheath 80 inserted through vessel puncture 92 to position the distal end 84 of sheath 80 within the vessel lumen 94. The vascular closure device 100 is aligned with the sheath 80. A first bioadhesive carrier 2 is mounted to the inner tube manifold 154 at a proximal end of the balloon location device 116.

FIG. 12 shows the vascular closure device 100 inserted through the sheath 80 to position the balloon 140 within the vessel lumen 94. The balloon 140 is inflated by delivering a volume of inflation fluid via the inflation fluid source 7. The vascular closure device 100 and sheath 80 are withdrawn proximately to contact the inflated balloon 140 against an inner surface of the vessel 90 to temporarily occlude blood flow through the vessel puncture 92. The area in and around the vessel puncture 92 may be aspirated via the aspiration lumen 88 and aspiration port 86 as shown in FIGS. 12 and 12A. The aspiration lumen 88 may be used as a blood flashback lumen as described above.

Referring to FIG. 13, the first bioadhesive carrier 2 is operated to deliver a first volume of bioadhesive through the second lumen 164 and out of the distal opening 166 into the area in and around the vessel puncture 92 and tissue tract 98. The first volume of bioadhesive may form the first bioadhesive plug 6. The first bioadhesive plug 6 may be cured into a solid or semi-solid state, which may assist in holding the first bioadhesive plug 6 within the tissue tract 98 and limit distal movement into the vessel lumen 94 after deflating balloon 140.

Figure 14:
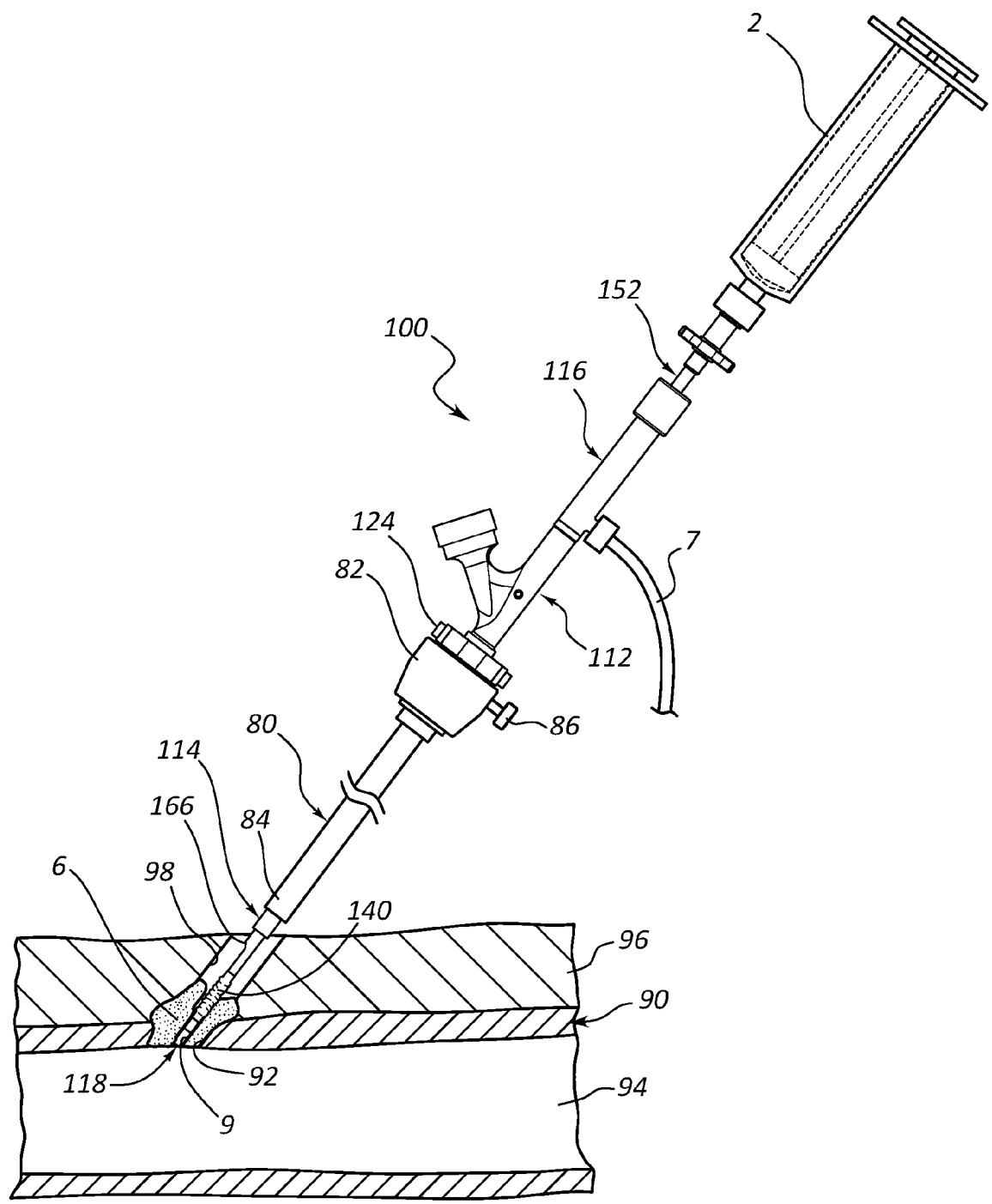

FIG. 14 shows the balloon 140 deflated and the vascular closure device 100 and sheath 80 withdrawn to a position in which the detachable sealing tip 118 is positioned within the channel 9 of the first bioadhesive plug 6. The vascular closure device 100 is operated to detach the detachable sealing tip 118 from the balloon location device 116 using any of the desired methods and systems disclosed herein. The detachable sealing tip 118 may substantially plug or seal the channel 9 to provide hemostasis through channel 9.

Figure 15:
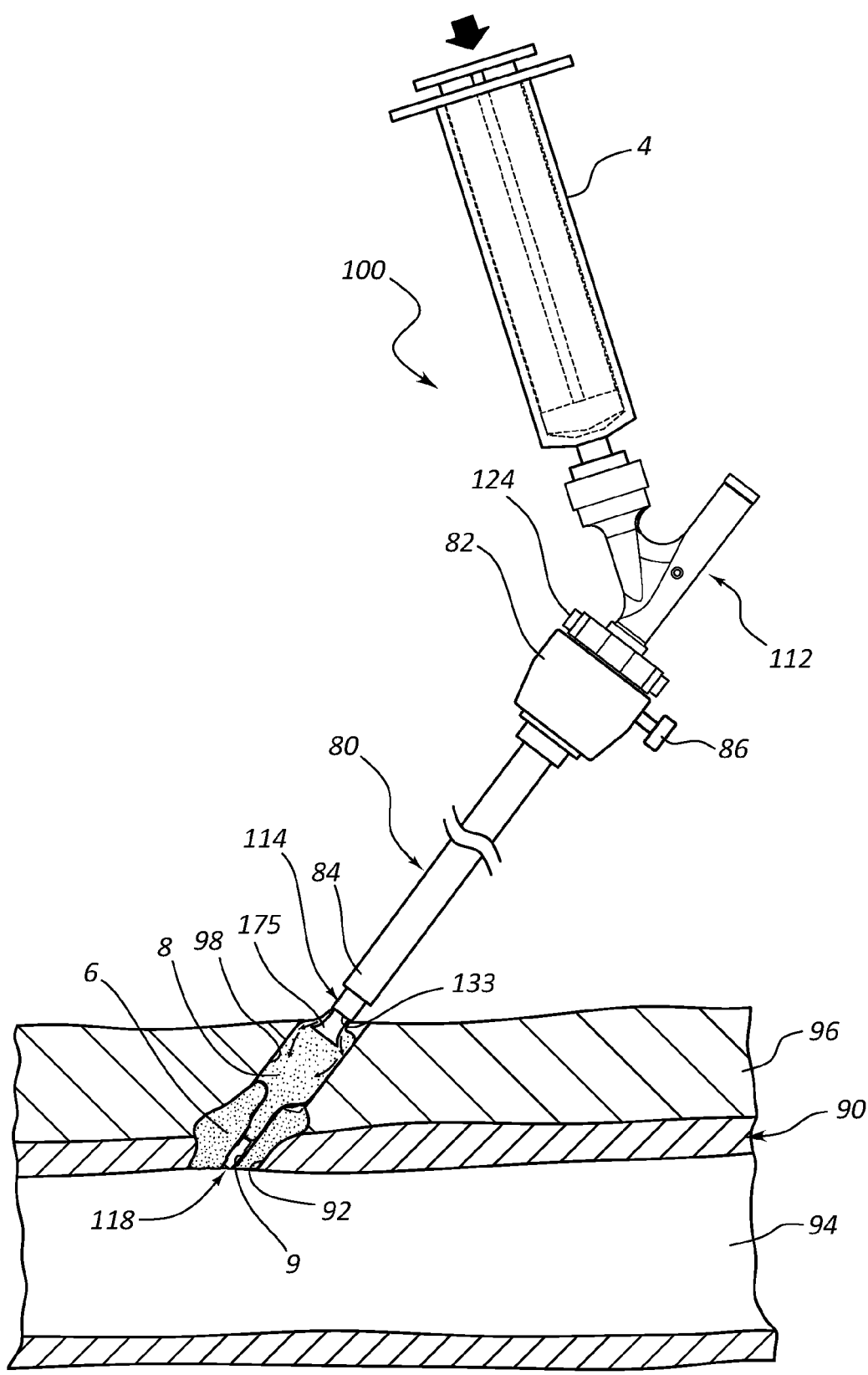

FIG. 15 show a second bioadhesive carrier 4 mounted to the injection port 122 and operated to deliver a second volume of bioadhesive through the lumen 130 of delivery tube 114 to the tissue tract 98. The hypotube 175 may be advanced distally relative to delivery tube 114 to open a channel or pathway through which the second volume of bioadhesive may travel between an outer surface of the hypotube 175 and an inner surface of the first lumen 130. In other arrangements, the second volume of bioadhesive may flow through the lumen 173 of hypotube 175 to be deposited within the tissue tract 98.

Figure 16:
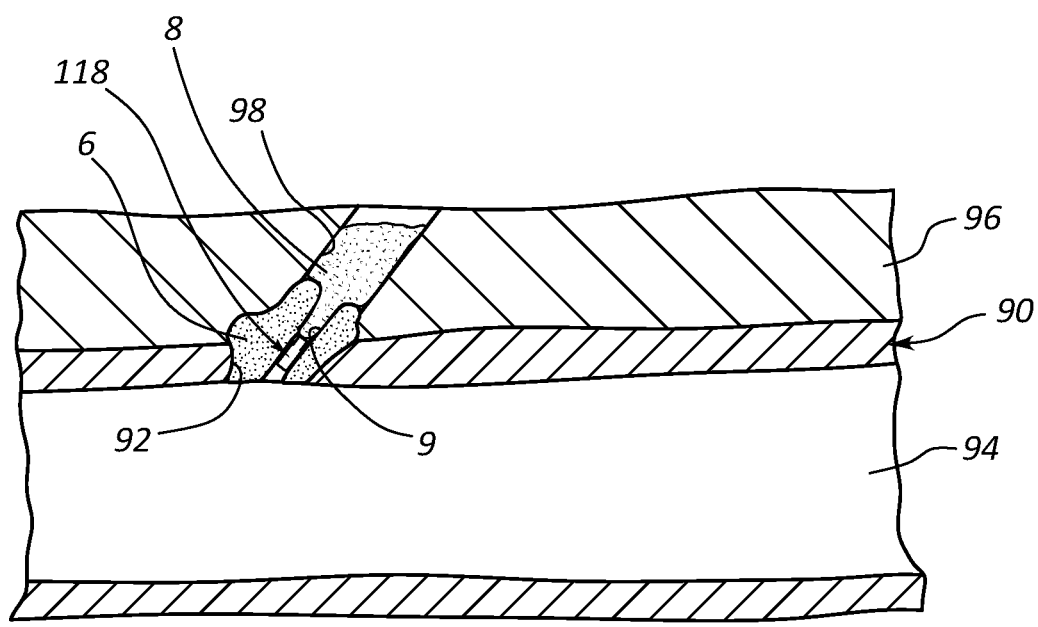

The second volume of bioadhesive may cure to form the second bioadhesive plug 8 as shown in FIG. 16. The second bioadhesive plug 8 may further seal channel 9 and tissue tract 98, and may bond with the detachable sealing tip 118 to provide anchoring of the detachable sealing tip 118.

Referring now to FIGS. 17-24, another example vascular closure device 200 is shown including a bioadhesive delivery device 211 (see FIG. 18), a balloon location device 216 and a detachable sealing tip 218. The detachable sealing tip 218 may be carried by the balloon location device 216. The balloon location device 216 may be inserted through a delivery tube 214 of the bioadhesive delivery device 211 to position a balloon 240 of the balloon location device 216 within a vessel lumen for temporarily sealing a vessel puncture.

The bioadhesive delivery device 211 may include a manifold 212 having the same or similar features as the manifold 12 described above. The manifold 212 may include an injection port 222, a latch 224, and a proximal seat 226. The delivery tube 214 includes first and second lumens 230, 232. The second lumen 232 includes a distal opening 234. The first and second lumens 230, 232 may be formed by separate and distinct first and second tubes 231, 233. The first and second tubes 231, 233 may be connected together using a sheath or shrink wrap member 238. The sheath 238 may secure the first and second tubes 231, 233 together along the length of the first and second tubes 231, 233 (see FIGS. 17A and 17B). In some arrangements, the first and second tubes 231, 233 may be secured together at multiple spaced apart locations long the length of the first and second tubes 231, 233.

The balloon location device 216 includes a balloon 240, a housing 250, an inner tube 252, an inner tube manifold 254, and an inflation manifold 256. The inner tube 252 includes proximal and distal ends 258, 260, and a first lumen 262. The lumen 262 may be arranged in flow communication with the balloon 240 via a plurality of inflation openings 242 (see FIG. 17B).

Figure 17B:
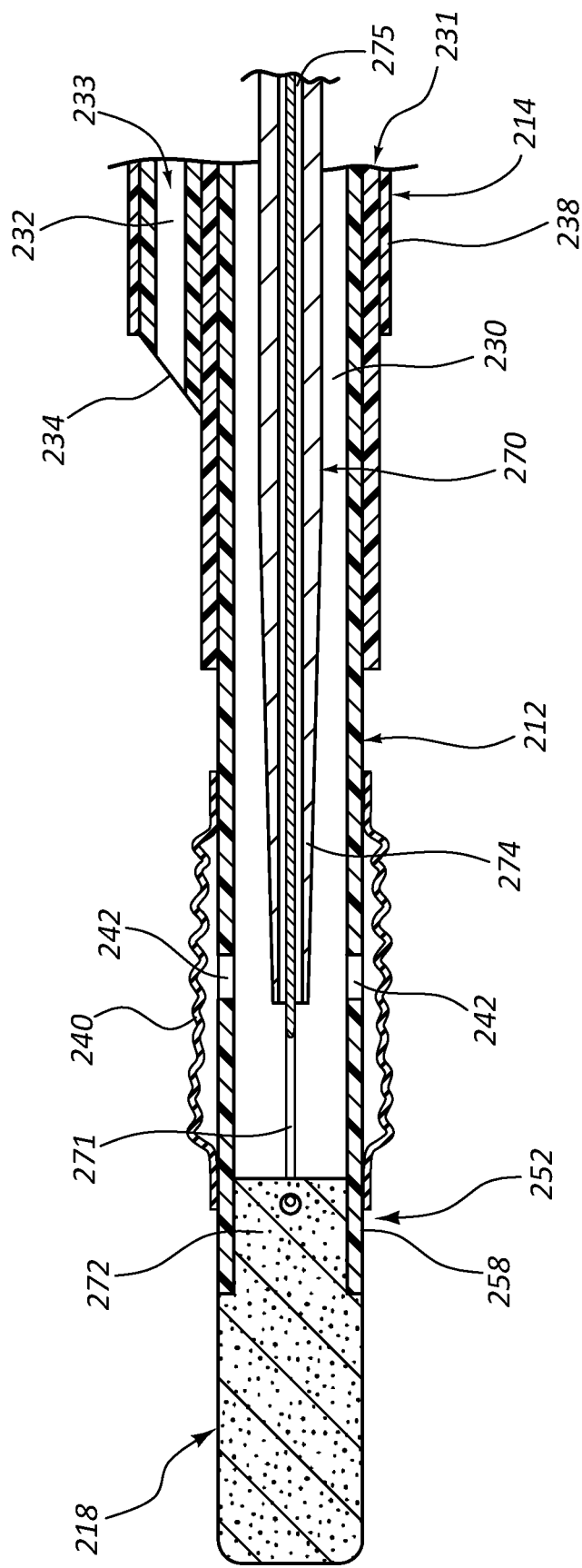
FIG. 17B is a cross-sectional view of a distal end portion of the vascular closure device of FIG. 17 taken along cross-section indicators 17B-17B.
Figure 18:
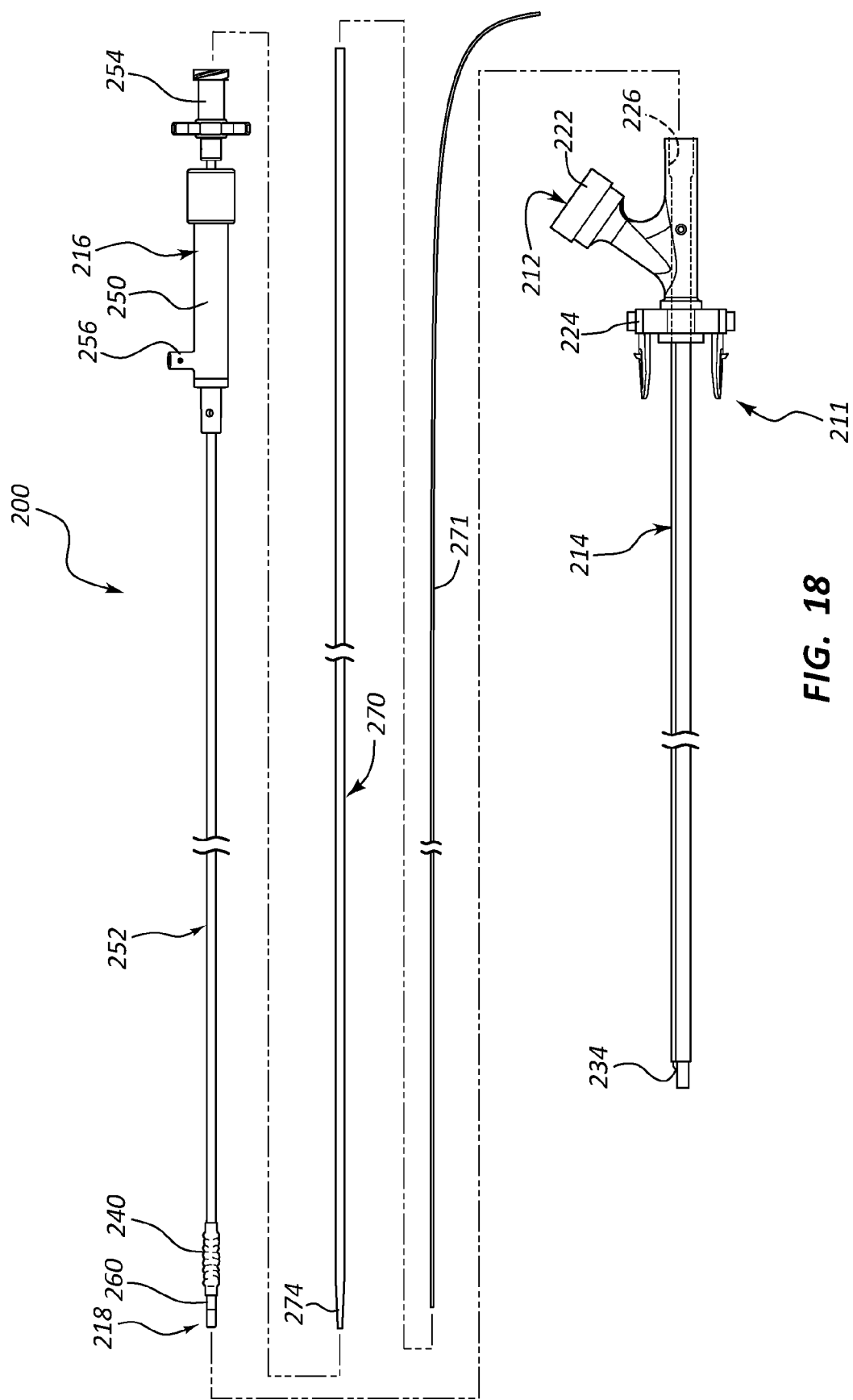
FIG. 18 is an exploded view of the vascular closure device of FIG. 17.

The detachable sealing tip 218 may include a proximal end 272. The proximal end 272 may extend into the first lumen 262. A filament 271 (e.g., a wire or suture) may be connected to the detachable sealing tip 218 as shown in FIG. 17B. A separate core wire or hypotube 270 may extend through the first lumen 262. The core wire 270 may include a tapered distal end portion 274 and a lumen 275. The filament 271 may extend through the lumen 275 as shown in FIG. 17B. The filament 271 may provide a positive attachment of the detachable sealing tip 218 to the balloon location device 216. Tension may be maintained in the filament 271 to hold the detachable sealing tip 218 assembled with the balloon location device 216 until a desired time for detaching the detachable sealing tip 218. In at least some examples, tension in the filament 271 is released by, for example, breaking the filament 271 or detaching the filament 271 from the detachable sealing tip 218. In other examples, the filament 271 remains attached to detachable sealing tip 218 after removal of the tension therein. The filament 271 may extend through the volumes of bioadhesive delivered to the vessel puncture. The filament 271 may be connected to at least one of the volumes of bioadhesive to provide additional anchoring of the detachable sealing tip 218 after the vascular closure device 200 is removed from the vessel puncture.

Figure 19:
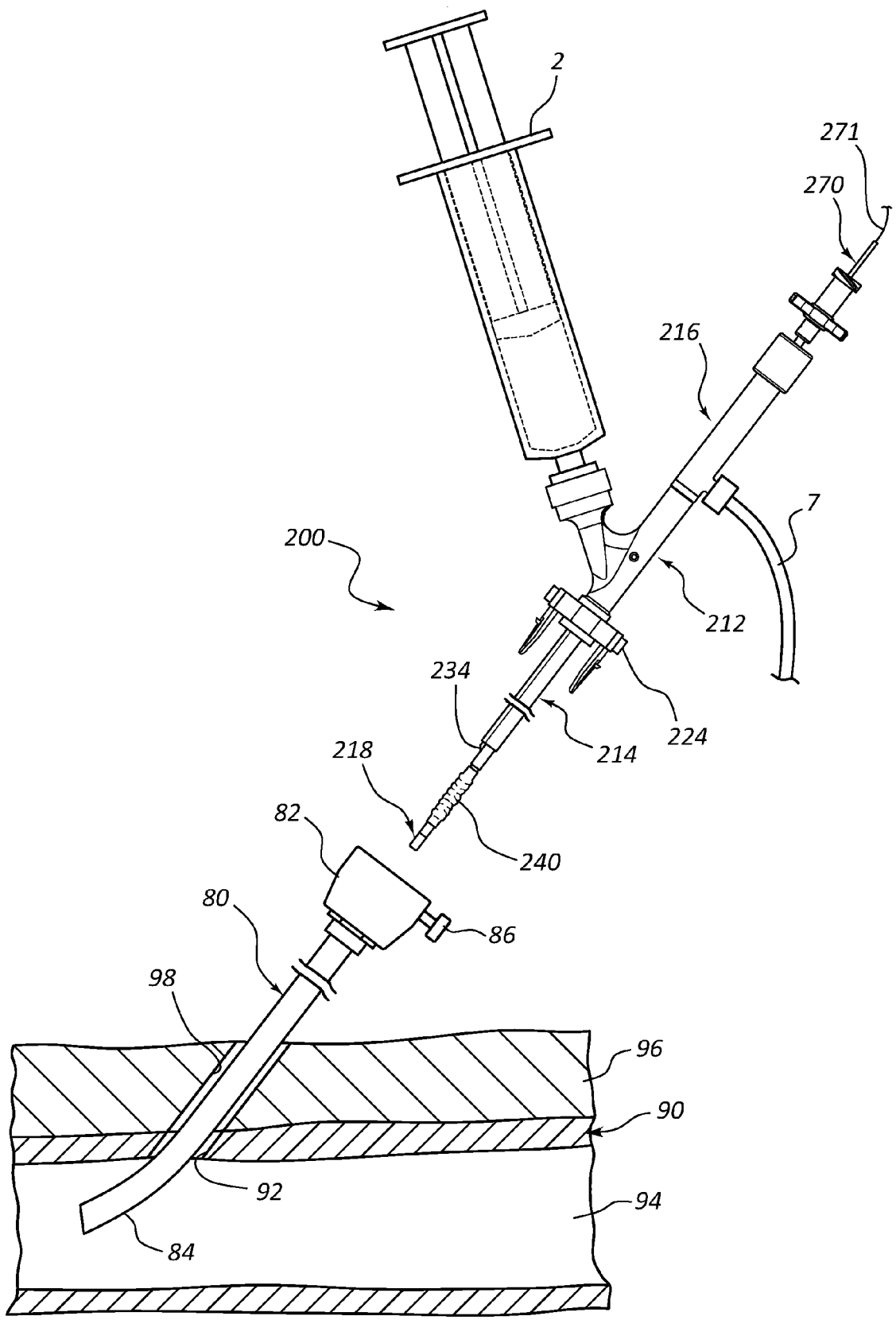

Referring to FIGS. 19-24, an example method of operating the vascular closure device 200 to seal vessel puncture 92 is shown and described. FIG. 19 shows the sheath 80 inserted through the vessel puncture 92 to position the distal end 84 within the vessel lumen 94. The vascular closure device 200 is aligned with the sheath 80. The first bioadhesive carrier 2 is mounted to the injection port 222.

FIG. 20 shows the vascular closure device 200 inserted through the sheath 80 to position the balloon 240 within the vessel lumen 94. A volume of inflation fluid is delivered from inflation fluid source 7 to expand balloon 240. The vascular closure device 200 and sheath 80 are withdrawn proximately to contact the inflatable balloon 240 against an inner surface of the vessel 90 to temporarily occlude blood flow through the vessel puncture 92. The area in and around vessel puncture 92 may be aspirated via, for example, the aspiration lumen 88 and aspiration port 86. Alternatively, the aspiration lumen 88 and aspiration port 86 may be used as a blood flashback indicator to provide a visual indication to the operator of a position of distal features of the vascular closure device 200 and sheath 80 relative to vessel lumen 94. FIG. 20A shows the aspiration lumen 88 extending around an exterior of the delivery tube 214 and within the sheath 80.

Figure 21:
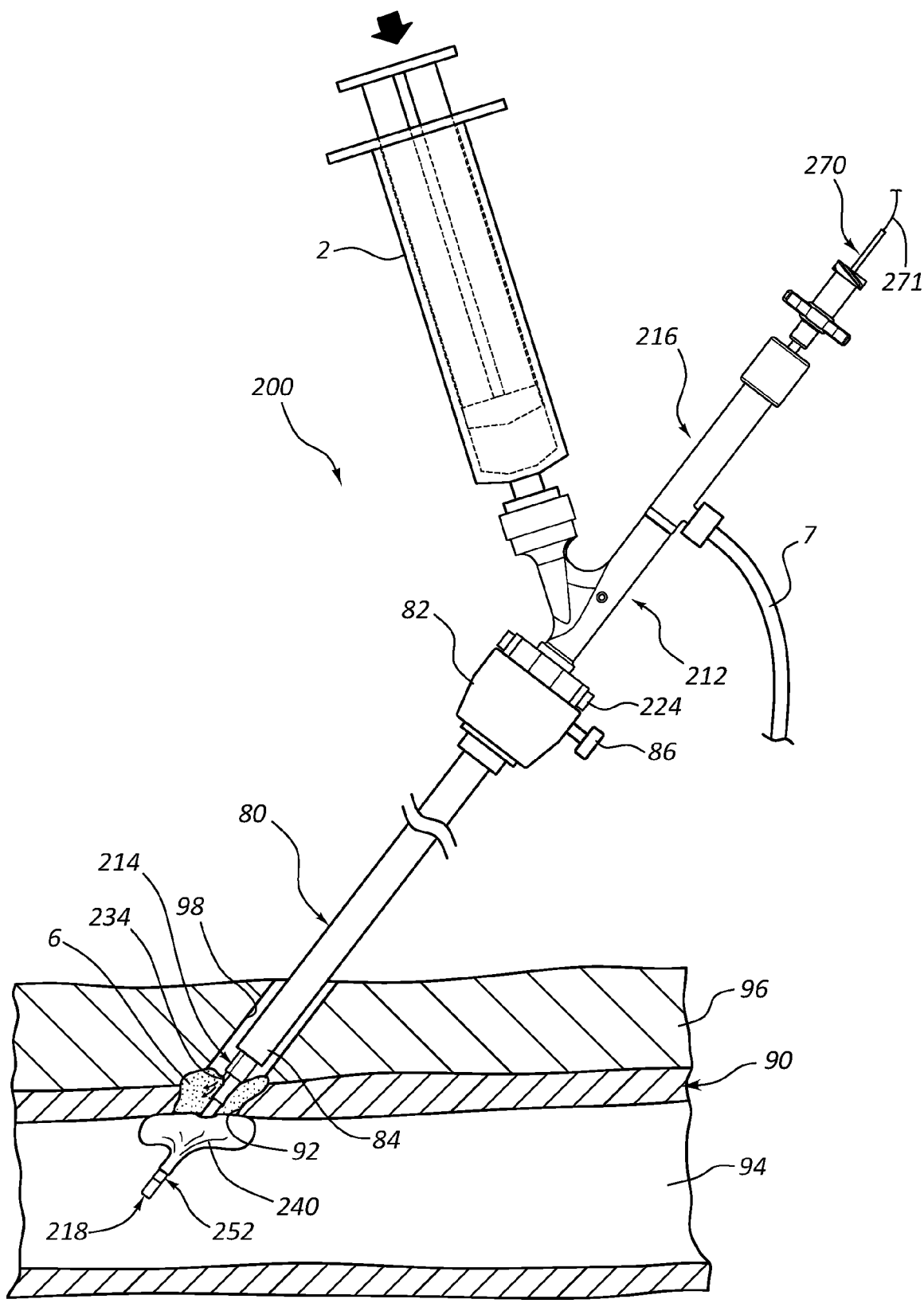

FIG. 21 shows the first bioadhesive carrier 2 operated to deliver a first volume of bioadhesive through the distal opening 234 of the second lumen 232 of delivery tube 214 and into vessel puncture 92 and tissue tract 98. The first volume of bioadhesive may cure to form a first bioadhesive plug 6. The first bioadhesive plug 6 may seal vessel puncture 92.

Figure 22:
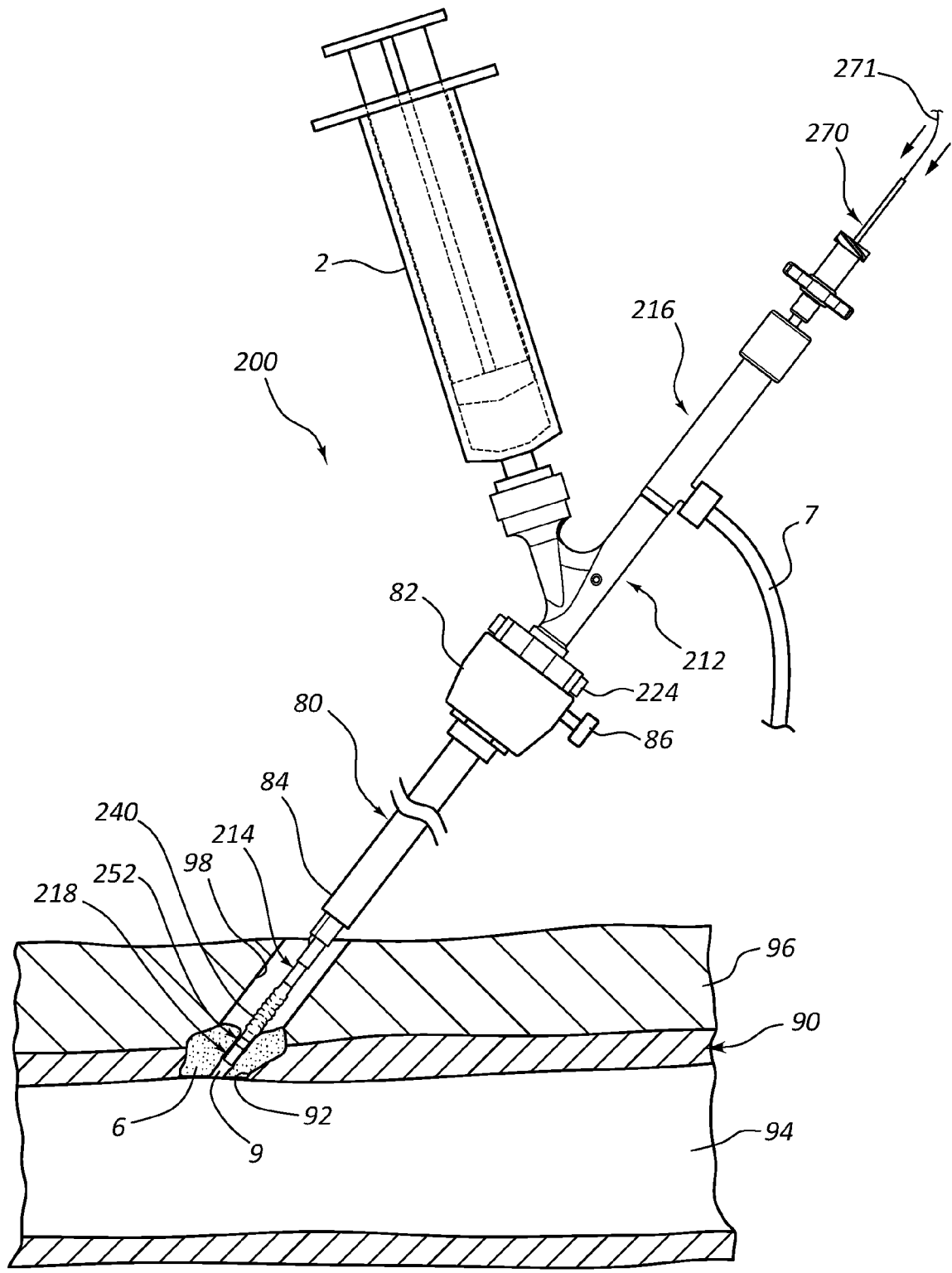

FIG. 22 shows the balloon 240 deflated and the vascular closure device 200 and sheath 80 withdrawn proximately until the detachable sealing tip 218 is positioned within channel 9 of the first bioadhesive plug 6. The vascular closure device 200 is operated to detach the detachable sealing tip 218 from the balloon location device 216. In at least one example, tension in filament 271 is released to permit the detachable sealing tip 218 to detach from the balloon location device 216. The detachable sealing tip 218 may occlude blood flow through the channel 9 and provide at least temporary sealing of the channel 9 until a second volume of bioadhesive is delivered to the vessel puncture.

Figure 23:
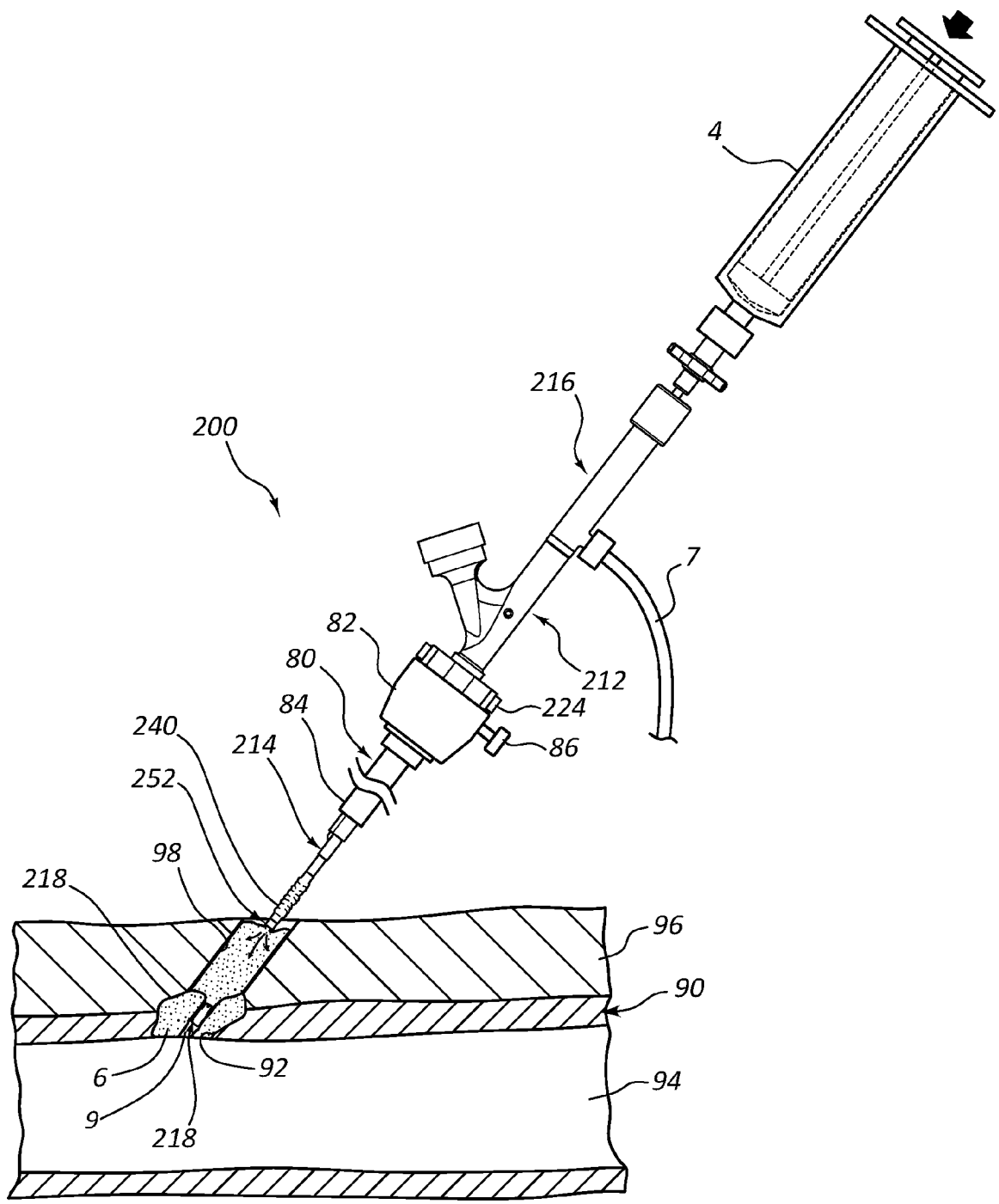
Figure 24:
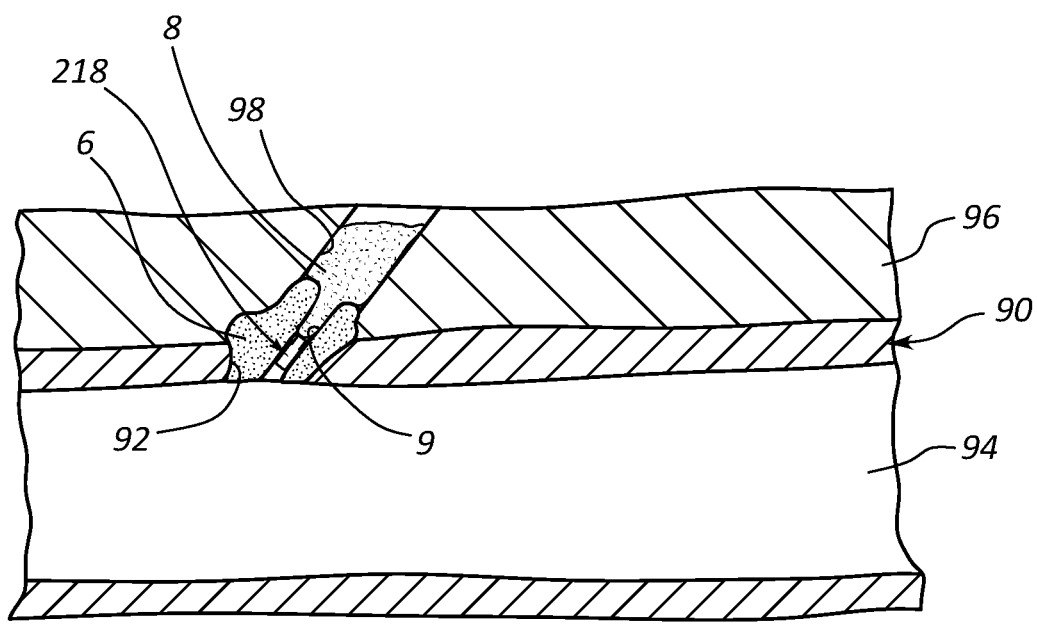

FIG. 23 shows a second bioadhesive carrier 4 coupled in flow communication with first lumen 262 of inner tube 252. The second bioadhesive carrier 4 may be operated to deliver a second volume of bioadhesive through, for example, the first lumen 262 and into the tissue tract 98. The second bioadhesive may flow into channel 9 to further seal channel 9. The second volume of bioadhesive may form into a second bioadhesive plug 8 as shown in FIG. 24. The second bioadhesive plug 8 may provide the same or similar functions as the second bioadhesive plug 8 described above with reference to FIGS. 1-16. Although not shown, the filament 271 may remain attached to detachable sealing tip 218 and extend through the second bioadhesive plug 8. The second bioadhesive plug 8 may connect to the filament 271 thereby providing further anchoring of detachable sealing tip 218.

Figure 25B:
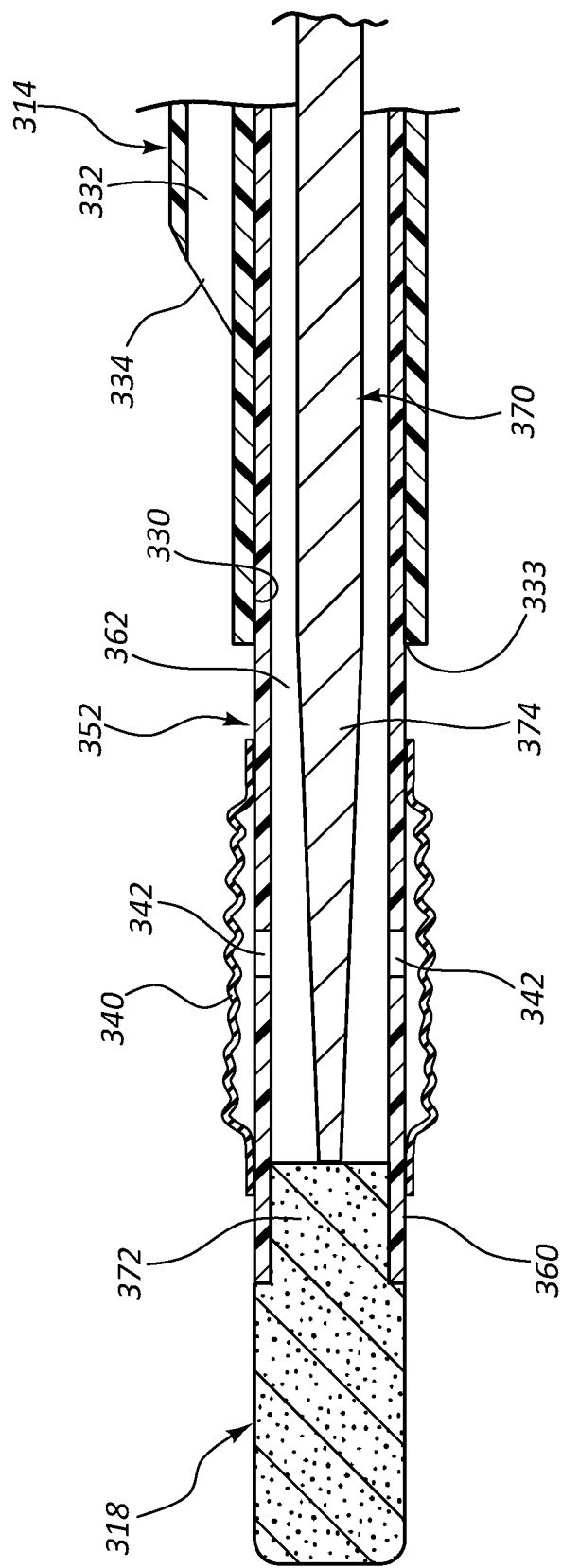
FIG. 25B is a cross-sectional view of a distal end portion of the vascular closure device of FIG. 25 taken along cross-section indicators 25B-25B.
Figure 25C:
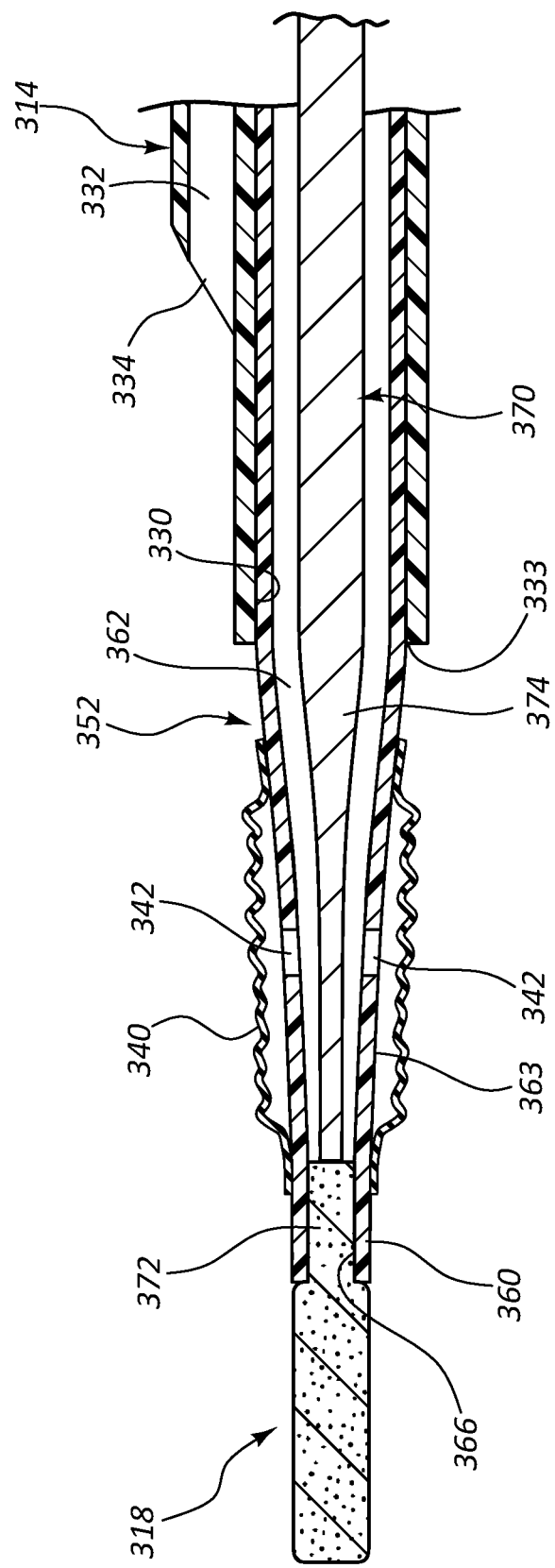
FIG. 25C is a cross-sectional view of an alternative embodiment of the distal end portion of the vascular closure device of FIG. 25 taken along cross-sectional indicators 25C-25C.
Figure 26:
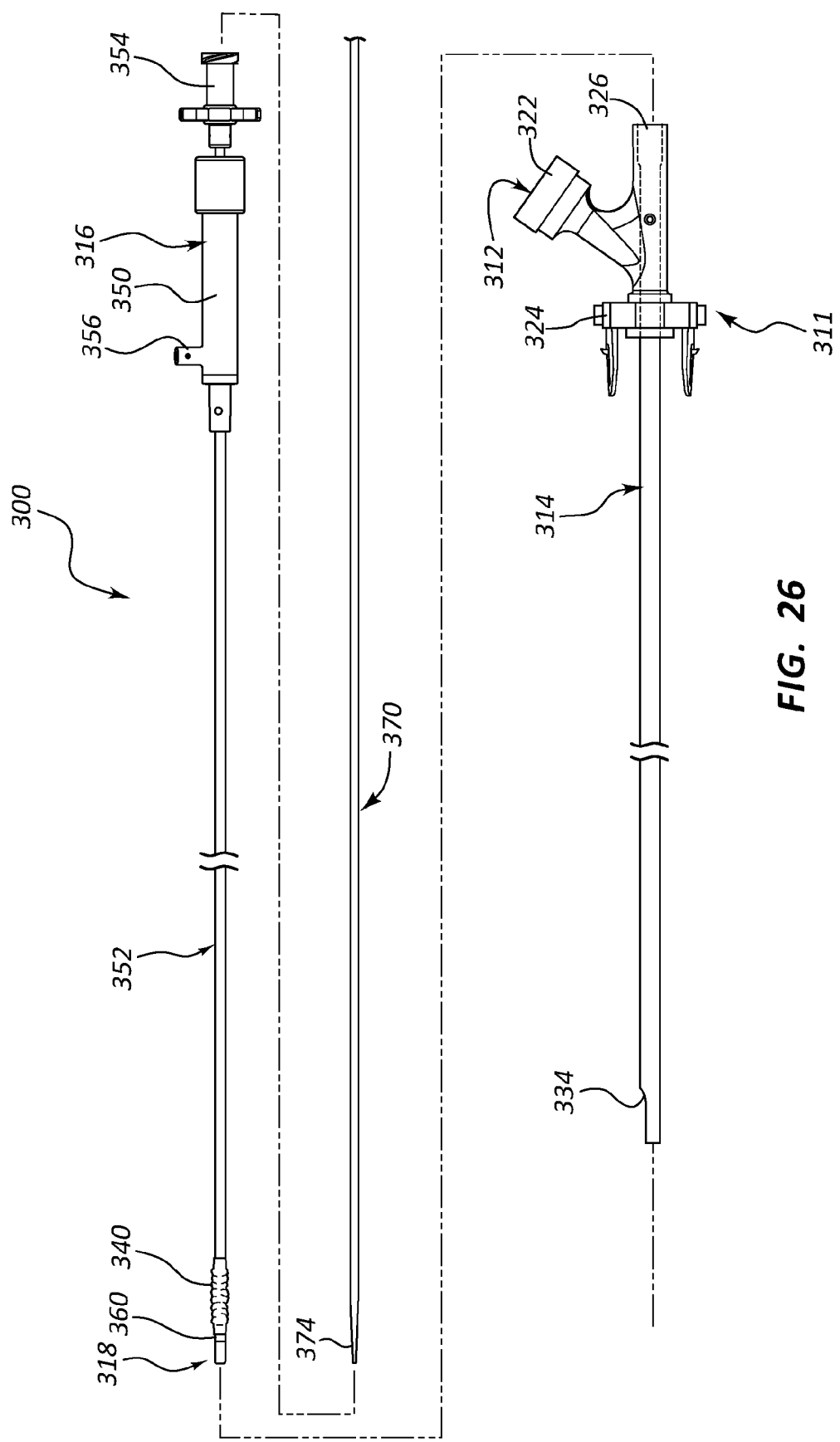
FIG. 26 is an exploded view of the vascular closure device of FIG. 25.

Referring now to FIGS. 25-33, another example vascular closure device 300 is shown including a bioadhesive delivery device 311 (see FIG. 26), a balloon location device 316, and a detachable sealing tip 318. The bioadhesive delivery device 311 is shown in FIG. 26 including a manifold 312 and a delivery tube 314. The manifold 312 includes an injection port 322, a latch 324, and a proximal seat 326. The manifold 312 may include the same or similar features as the manifold 12 described above. The delivery tube 314 includes a first lumen 330 having a distal opening 333, and a second lumen 332 having a distal opening 334 (see FIGS. 25A and 25B). The first lumen 330 is configured for insertion of a balloon location device 316 to position the detachable sealing tip 318 distal of the distal end of delivery tube 314.

The balloon location device 316 includes a balloon 340, a housing 350, an inner tube 352, an inner tube manifold 354, and an inflation manifold 356. The inner tube 352 includes proximal and distal ends 358, 360, and a first lumen 362. A core wire 370 may extend through the first lumen 362 at least during delivery of the vascular closure device 300 to the vessel puncture. The first lumen 362 may be connected in flow communication with an inflation balloon 340 via a plurality of inflation openings 342 (see FIG. 25B). The core wire 370 may be connected to the detachable sealing tip 318 as shown in FIG. 25B. In some arrangements, the core wire 370 may be detachable from the detachable sealing tip 318 as part of detaching the detachable sealing tip 318 from the balloon location device 316.

The detachable sealing tip 318 may include a proximal end 372 as shown in FIG. 25. The proximal end 372 may extend into the inner tube 352. The remaining portions of the detachable sealing tip 318 may extend distally from the balloon location device 316 and define a distal portion of the vascular closure device 300.

The core wire 370 may include a tapered distal portion 374 as shown in FIG. 25B. In other arrangements, the inner tube 352 may also include a tapered distal portion 363 as shown in FIG. 25C. The tapered distal portion 363 may align with the tapered distal portion 374 of core wire 370. The tapered features of the balloon location device 316 and core wire 370 shown in FIG. 25C may provide a reduced outer profile for the distal most portions of the balloon location device 316. An outer profile of the detachable sealing tip 318 may also may be minimized such that the entire distal end portion of the vascular closure device 300 has a reduced outer profile as compared to other embodiments disclosed herein, which may provide improved insertability through a vessel puncture.

Figure 27:
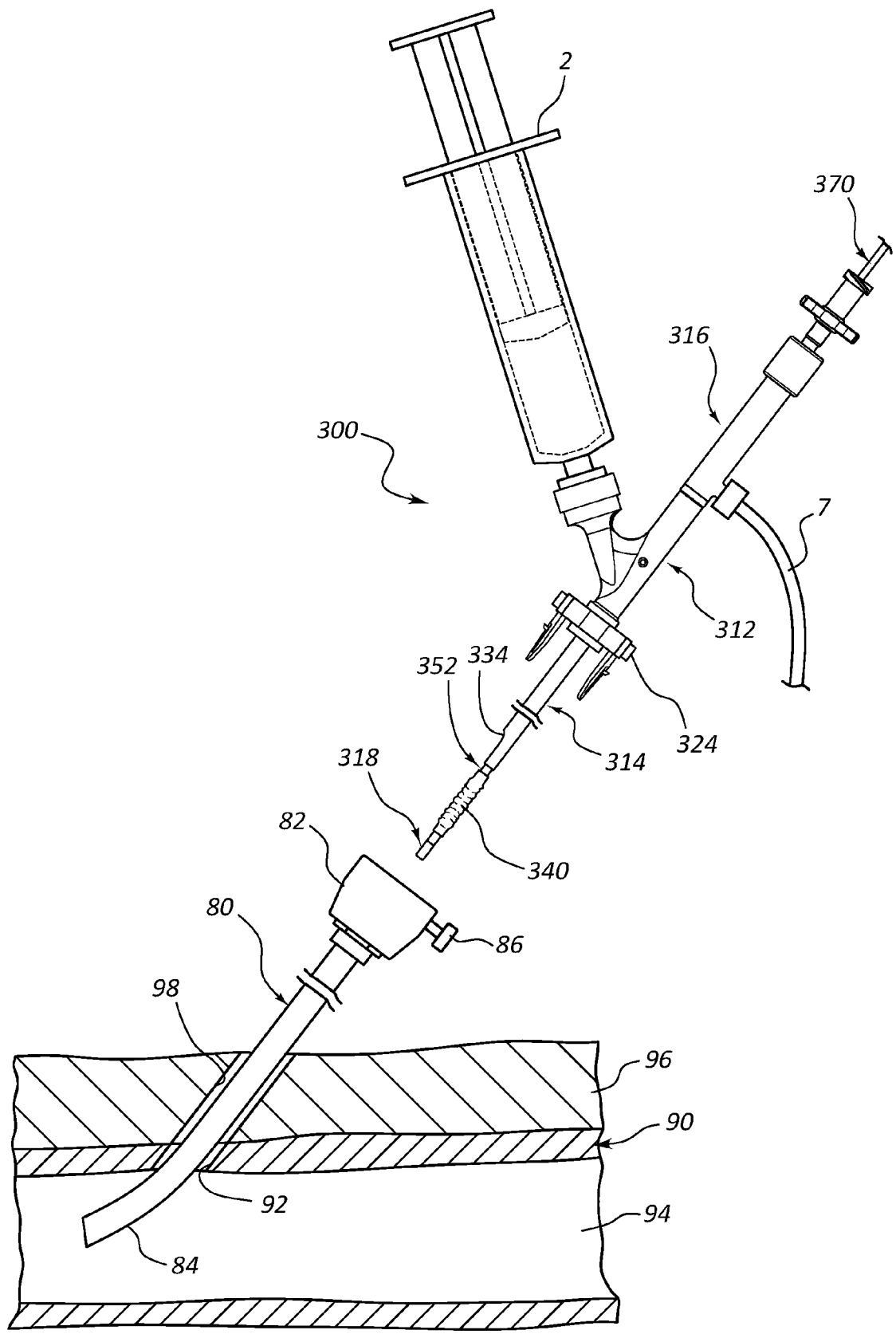
FIGS. 27-33 illustrate use of the vascular closure device of FIG. 25 with a sheath to seal a vessel puncture in accordance with the present disclosure.

FIGS. 27-33 show steps of an example method of using the vascular closure device 300 for sealing a vessel puncture 92. FIG. 27 shows sheath 80 extending through vessel puncture 92 and into vessel lumen 94. The vascular closure device 300 is aligned with the sheath 80 and prepared for insertion through the sheath 80 and into vessel lumen 94.

Figures 28, 28A:
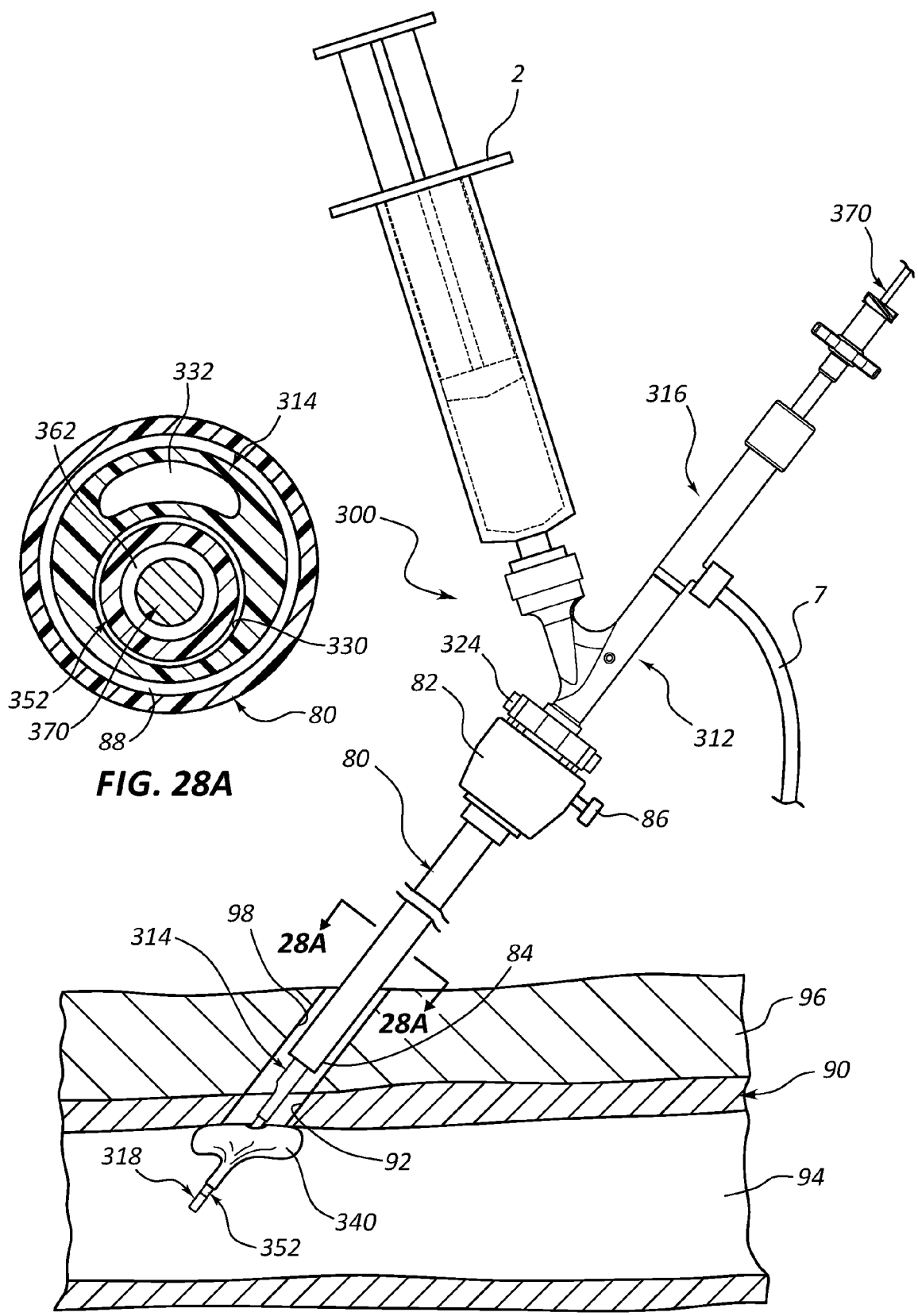

FIG. 28 shows the vascular closure device 300 inserted through the first lumen 330 of delivery tube 314 to position balloon 340 within vessel lumen 94. The latch 324 is connected to hub 82. The balloon 340 is inflated by delivering a volume of inflation fluid via inflation fluid source 7. The entire vascular closure device 300 and sheath 80 may be withdrawn proximately to contact the inflated balloon 340 against the inner surface of the vessel 90 to temporarily occlude blood flow through the vessel puncture 92. The area in and around vessel puncture 92 may be aspirated via aspiration lumen 88 and aspiration port 86 (see FIGS. 28 and 28A). The aspiration lumen 88 and aspiration port 86 may be used as blood flashback features for providing a visual indicator to the operator of a position of distal portions of the vascular closure device 300 and sheath 80 relative to vessel lumen 94.

Figure 29:
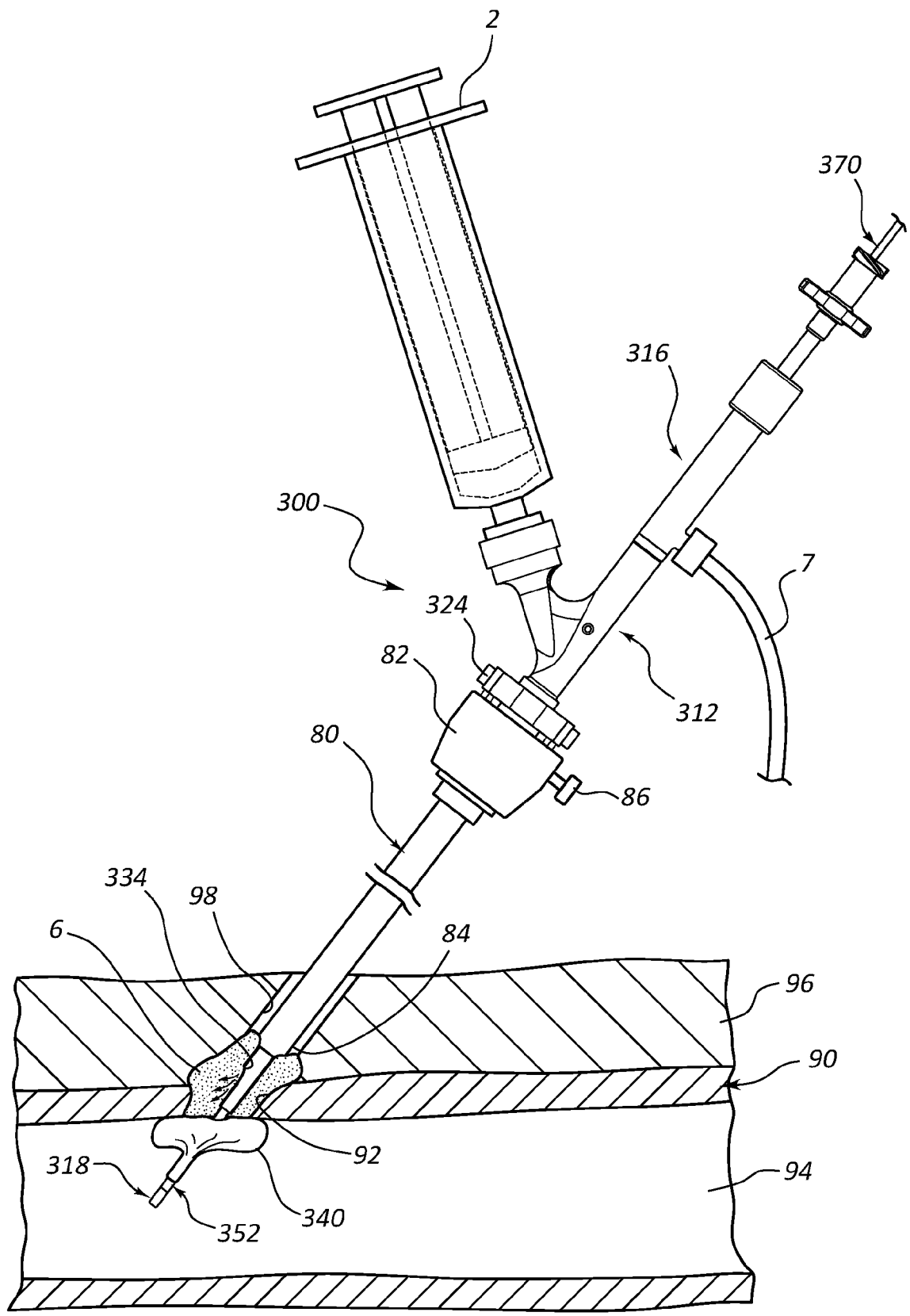

Referring to FIG. 29, a first bioadhesive carrier 2, which is coupled in flow communication with the injection port 322, is operated to deliver a first volume of bioadhesive to vessel puncture 92 and tissue tract 98. The first volume of bioadhesive is delivered to the second lumen 332 of the delivery tube 314 and injected at the distal opening 334. The first volume of bioadhesive is cured to form a first bioadhesive plug 6. The first bioadhesive plug 6 is cured into a solid or semi-solid state that limits distal movement of the first bioadhesive plug 6 after deflating balloon 340.

Figure 30:
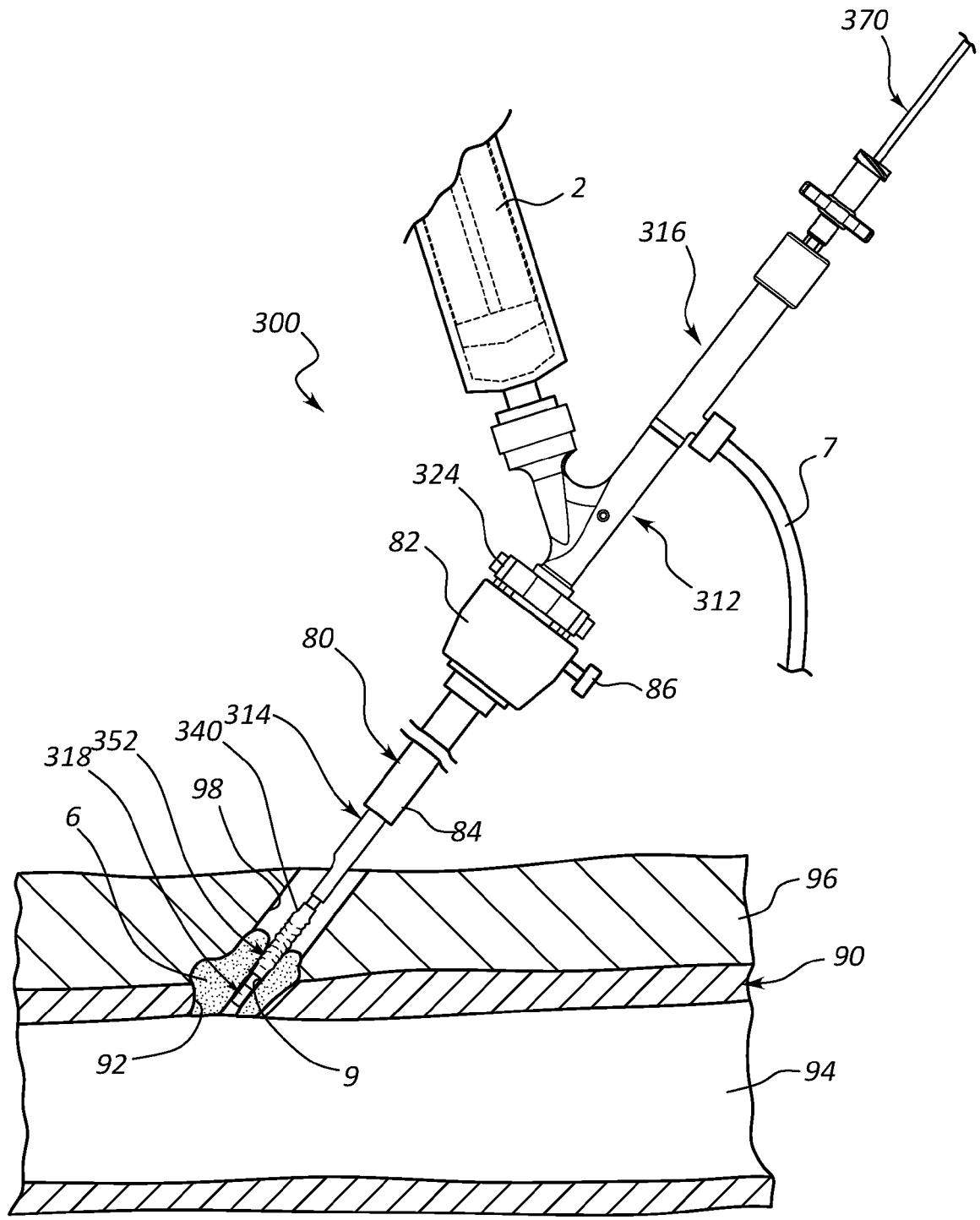

FIG. 30 shows the balloon 340 deflated and the vascular closure device 300 and sheath 80 withdrawn proximately to position detachable sealing tip 318 within channel 9 of the first bioadhesive plug 6. The vascular closure device 300 may be operated to detach the detachable sealing tip 318 from the balloon location device 316. In some arrangements, such as when the core wire 370 is connected to detachable sealing tip 318, the core wire 370 may be actuated to assist in detaching the detachable sealing tip 318 from balloon location device 316. The detachable sealing tip 318 provides at least temporary sealing of channel 9 to provide hemostasis after removal of the vascular closure device 300.

Figure 31:
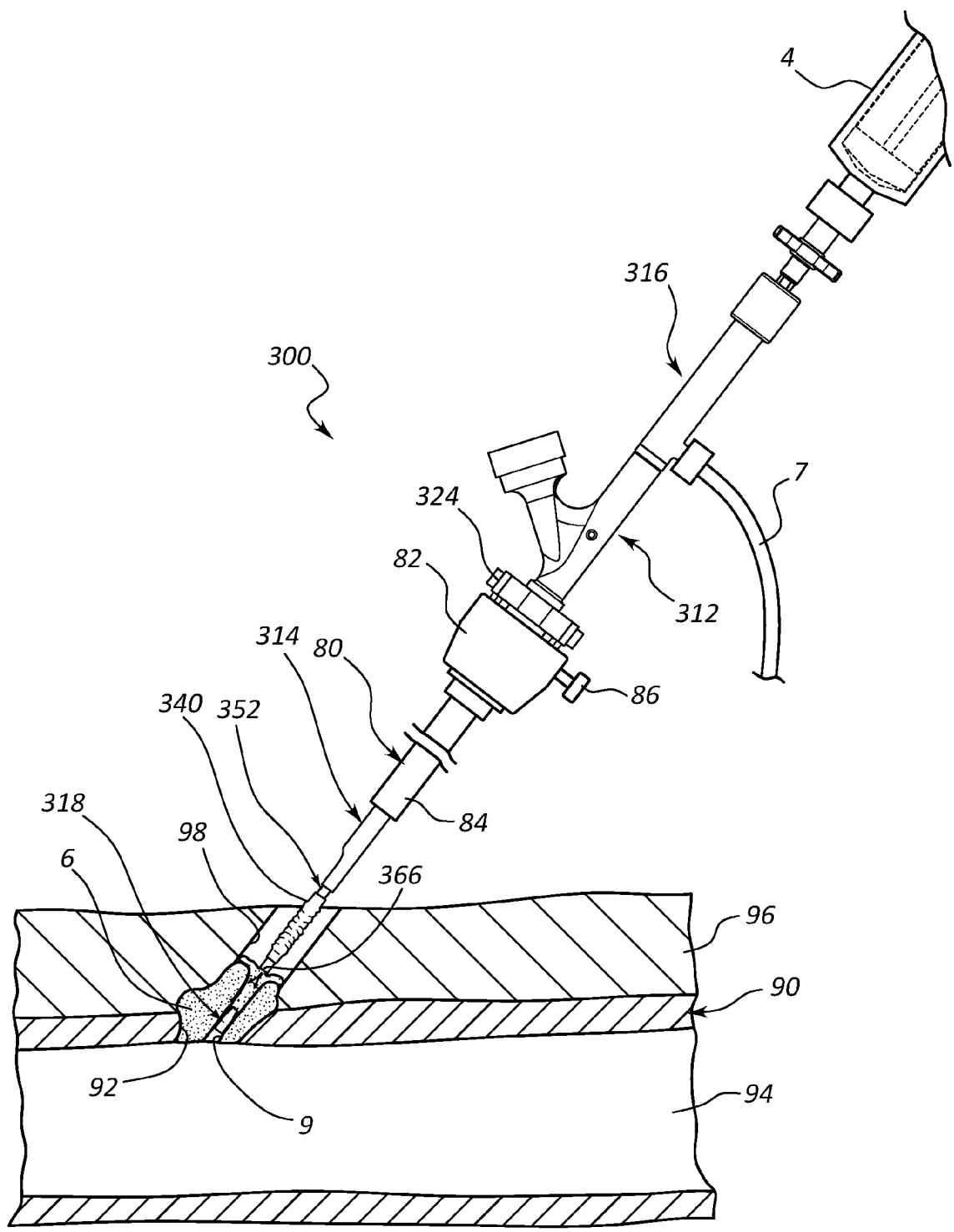
Figure 33:
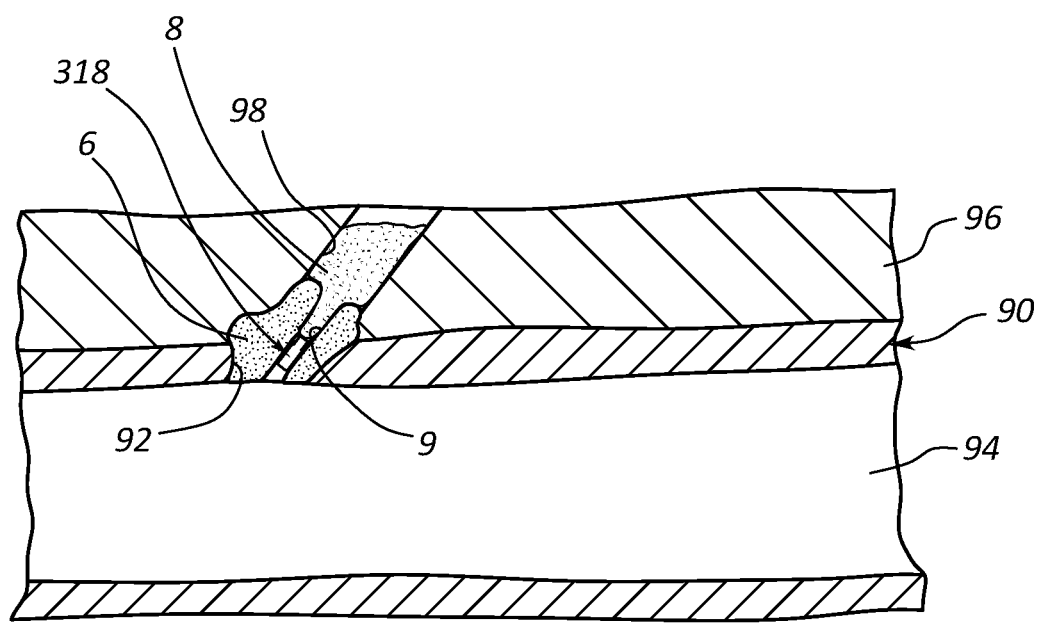

FIG. 31 shows a second bioadhesive carrier 4 mounted to the balloon location device 316 to provide a second volume of bioadhesive through the inner tube 352 to the tissue tract 98. In some arrangements, the core wire 370 is removed prior to delivering the second volume of bioadhesive. The second volume of bioadhesive may be ejected out of a distal opening 366 of first lumen 362 (see FIGS. 25C and 31). The second volume of bioadhesive may at least partially fill the tissue tract 98. The second volume of bioadhesive may flow into channel 9 to seal channel 9 and further seal vessel puncture 92 as shown in FIG. 33. The second volume of bioadhesive may bond to the detachable sealing tip 318 to provide anchoring of detachable sealing tip 318.

The second volume of bioadhesive may form a second bioadhesive plug 8 as shown in FIG. 33. The second bioadhesive plug 8 may be positioned proximal of the first bioadhesive plug 6 and may further seal channel 9 and vessel puncture 92.

Figure 32:
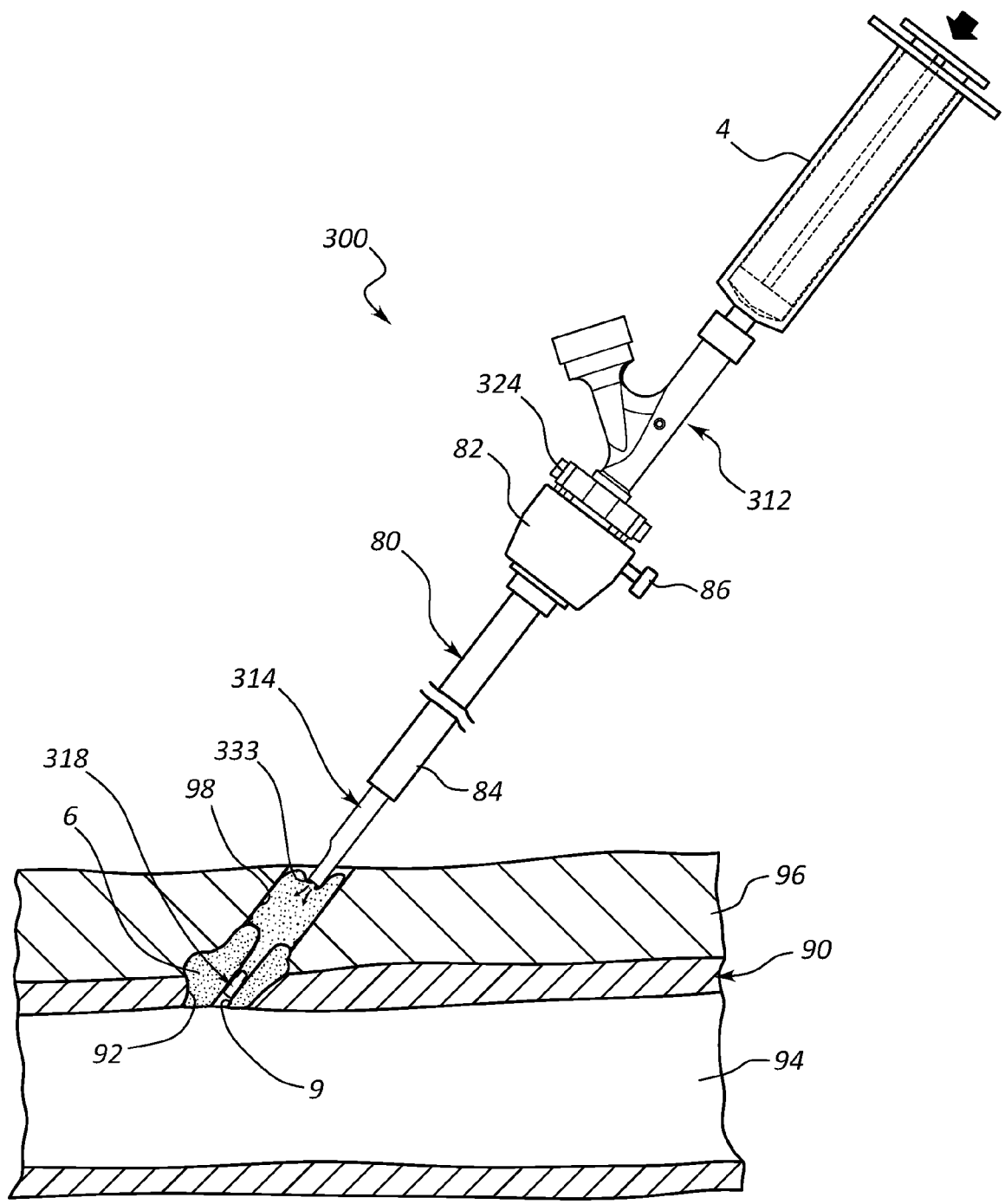

In an alternative arrangement, the second volume of bioadhesive is delivered through the first lumen 330 of the delivery tube 314 as shown in FIG. 32. The balloon location device 316 may be removed from the bioadhesive delivery device 311 as shown in FIG. 32. The second bioadhesive carrier 4 may be connected to manifold 312 to provide delivery of the second bioadhesive through the first lumen 330, out of the distal opening 333 and into the tissue tract 98 to form the second bioadhesive plug 8.

FIGS. 34-41 show another example vascular closure device 400. The vascular closure device 400 includes a bioadhesive delivery device 411 (see FIG. 35), a balloon location device 416, and a detachable sealing tip 418. A bioadhesive delivery device 411 includes a manifold 412 and a delivery tube 414. The manifold 412 includes an injection port 422, a latch 424 and a proximal seat 426. The manifold 412 may have the same or similar features and function as the manifold 12 described above.

The delivery tube 414 includes a first lumen 430 having a distal opening 433 and may further include a pass through channel 435. Delivery tube 414 also includes a second lumen 432 having a distal opening 434. A plurality of cutouts 436 may be formed in an outer surface of the delivery tube 414 as shown in at least FIGS. 34A and 37. The cutouts 436 may provide longitudinal grooves or channels for aspiration or blood flashback when the delivery tube 414 is used with sheath 80 as described below. The cutouts 436 may be used with any of the embodiments disclosed herein.

Figure 34B:
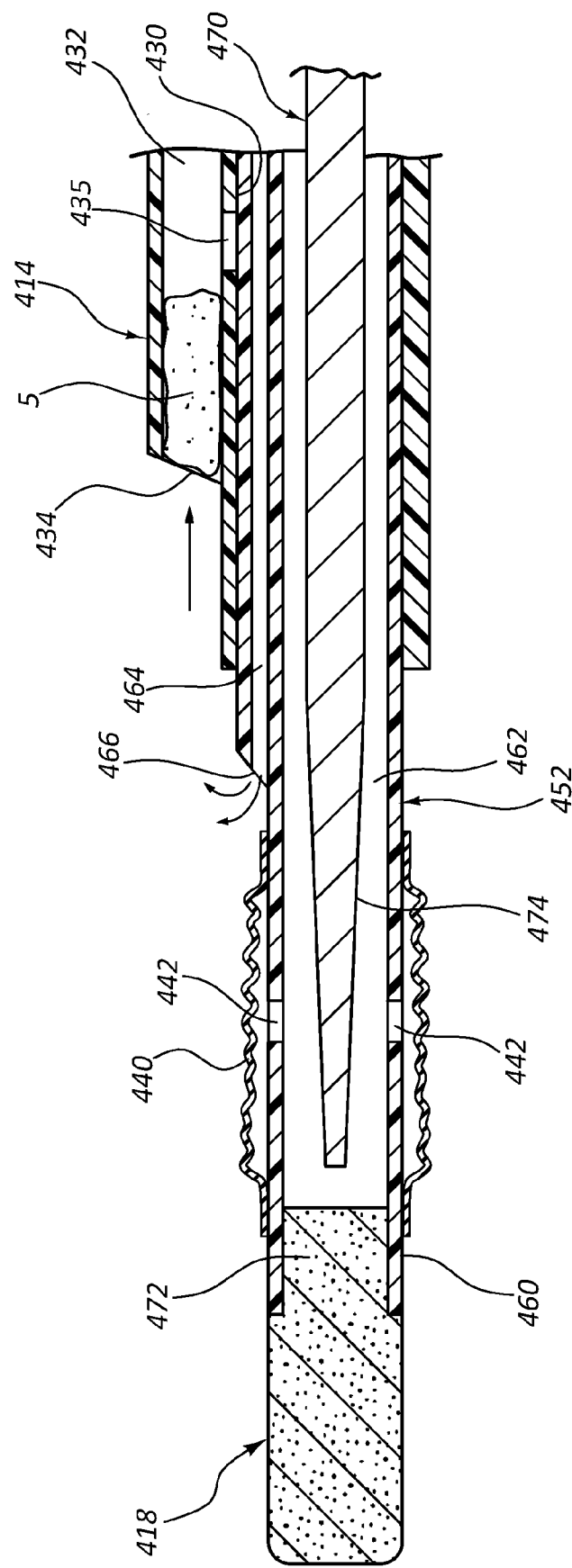
FIG. 34B is a cross-sectional view of a distal end portion of the vascular closure device of FIG. 34 taken along cross-section indicators 34B-34B.
Figure 34C:
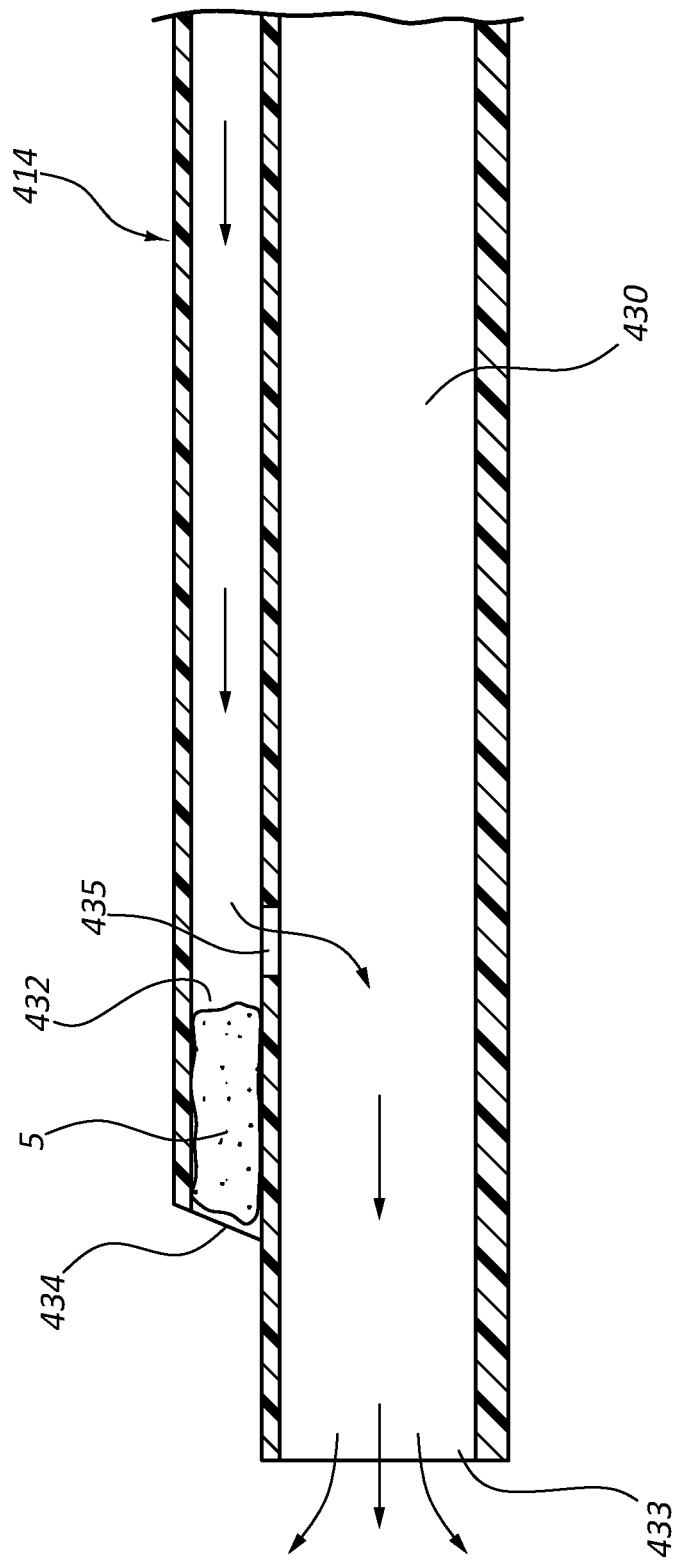
FIG. 34C is a cross-sectional view of an alternative embodiment of the distal end portion of the vascular closure device of FIG. 34 with a vessel locating device removed.
Figure 35:
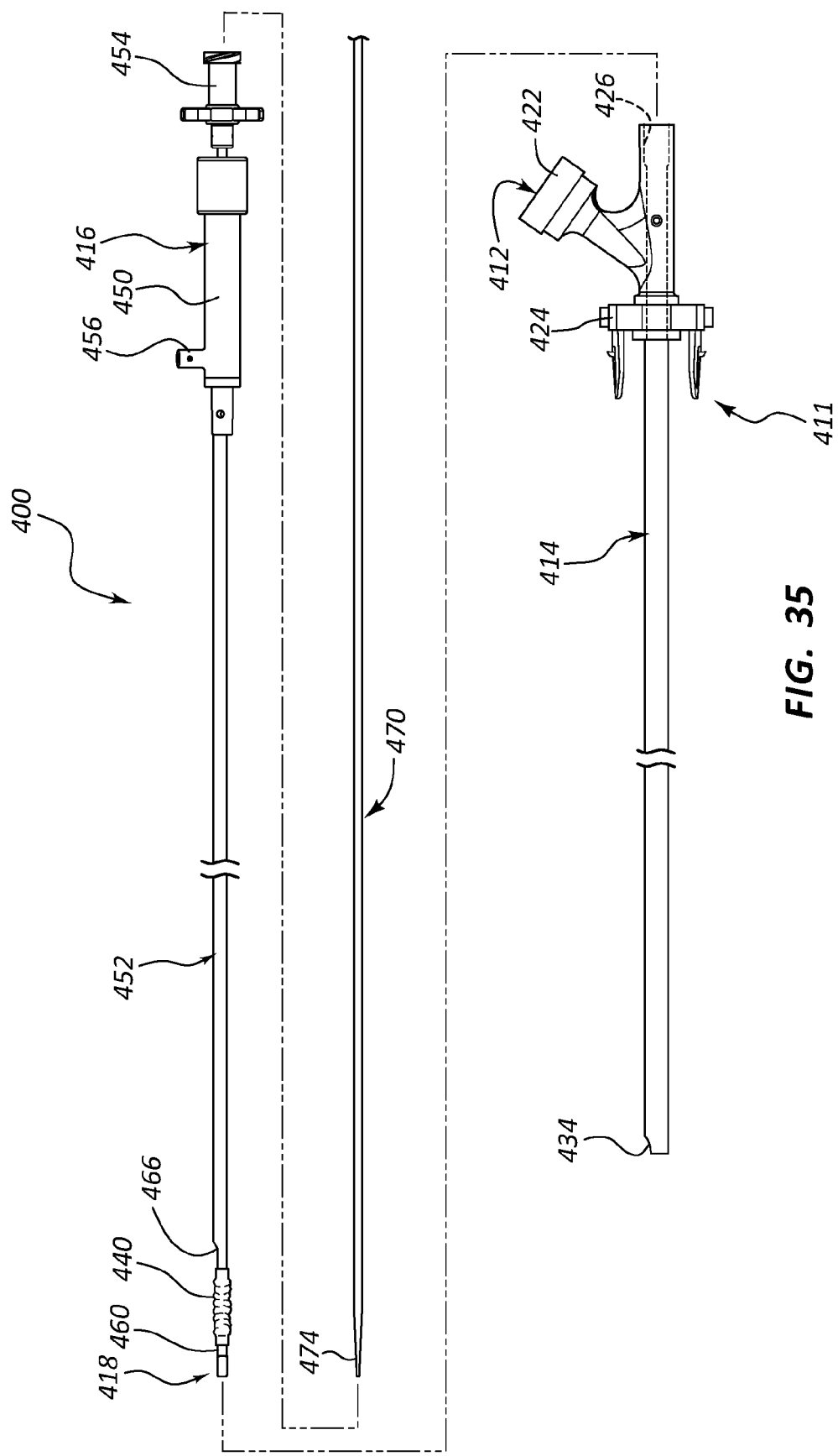
FIG. 35 is an exploded view of the vascular closure device of FIG. 34.

A path through channel 435 may extend between the first and second lumens 430, 432 as shown in FIGS. 34B and 34C. In at least some arrangements, the second lumen 432 may be plugged with a portion of the first volume of bioadhesive and is delivered to the vessel puncture. The path through channel 435 provides a pathway for a second volume of bioadhesive to flow through the second lumen 432 and out through the distal opening 433 of the first lumen 430, thereby bypassing a backflow plug 5 of the first volume of bioadhesive (see FIGS. 34B and 34C). Other arrangements are possible in which no pass through channel 435 is provided. In one such arrangement, delivering the second volume of bioadhesive through the second lumen 432 may eject any of the first volume of bioadhesive that may have entered into the distal opening 434 through the second lumen 432.

In other arrangements, a first volume of bioadhesive is delivered to the vessel puncture through the second lumen 432 and out through the distal opening 434. A second volume of bioadhesive is delivered through the balloon location device 416 (e.g., through a second lumen 464 as described below).

The balloon location device 416 includes a balloon 440, a housing 450, an inner tube 452, an inner tube manifold 454, and an inflation manifold 456. Inner tube 452 includes proximal and distal ends 458, 460, a first lumen 462, and a second lumen 464 having a distal opening 466 (see FIGS. 34A and 34B). The balloon 440 may be arranged in flow communication with the first lumen 462 via a plurality of inflation openings 442 (see FIG. 34B). The second lumen 464 may provide delivery of a first volume of bioadhesive to the vessel puncture. The distal opening 466 may be positioned proximal of balloon 440. Portions of the first volume of bioadhesive delivered to the vessel puncture via the second lumen 464 may, after being ejected, flow proximately into distal opening 434 of second lumen 432 of the delivery tube 414 as shown in FIG. 34B. The portion of the first volume of bioadhesive that enters into the second lumen 432 may form a backflow plug 5. The pass through channel 435 may provide a passageway for flow of a second volume of bioadhesive through the second lumen 432 and into the first lumen 430, for example, after the balloon location device 416 is removed from the bioadhesive delivery device 411 as shown in FIG. 34C. The second volume of bioadhesive may flow out of the distal opening 433 of the first lumen 430 as shown in FIG. 34C.

The detachable sealing tip 418 may include a proximal end 472, which may be inserted within the inner tube 452 as shown in FIG. 34B. The vascular closure device 400 includes a core wire 470, which extends along at least a portion of the length of the balloon location device 416. FIG. 34B shows the core wire 470 having a tapered distal portion 474. As discussed above, the core wire 470 may be connected to the detachable sealing tip 418 and may be detachable from the detachable sealing tip 418 as part of detaching the detachable sealing tip 418 from the balloon location device 416.

Figure 36:
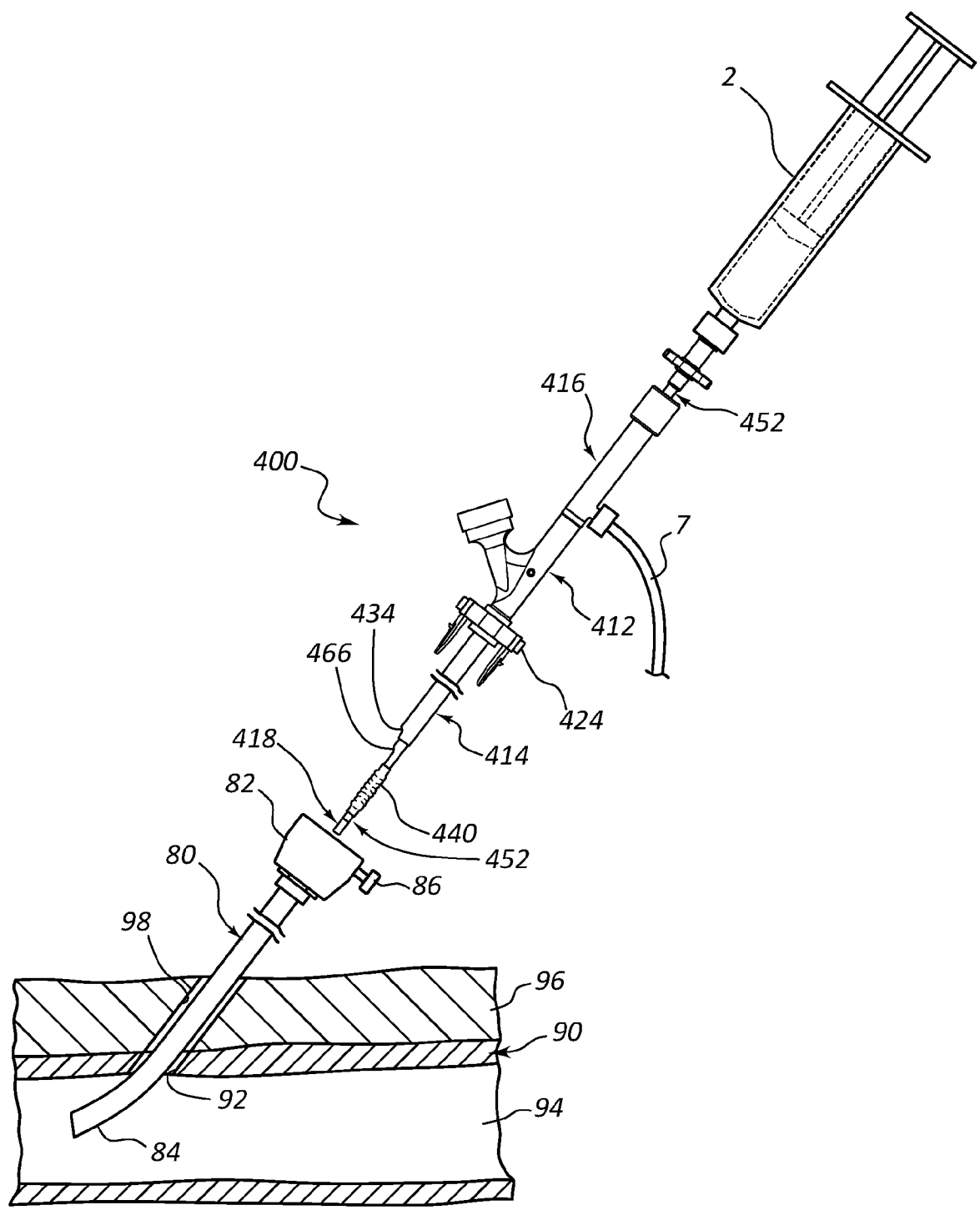
FIGS. 36-41 illustrate use of the vascular closure device of FIG. 34 with a sheath to seal a vessel puncture in accordance with the present disclosure.

FIGS. 36-41 show an example method of using vascular closure device 400 to seal a vessel puncture 92. FIG. 36 shows sheath 80 inserted through vessel puncture 92 to position distal end 84 within vessel lumen 94. The vascular closure device 400 is aligned with an opening into a proximal opening in sheath 80 as shown in FIG. 36. A first bioadhesive carrier 2 may be connected in flow communication with the second lumen 464 of the inner tube 452. The first bioadhesive carrier 2 may be connected to the balloon location device 416 at the inner tube manifold 454.

Figures 37, 37A:
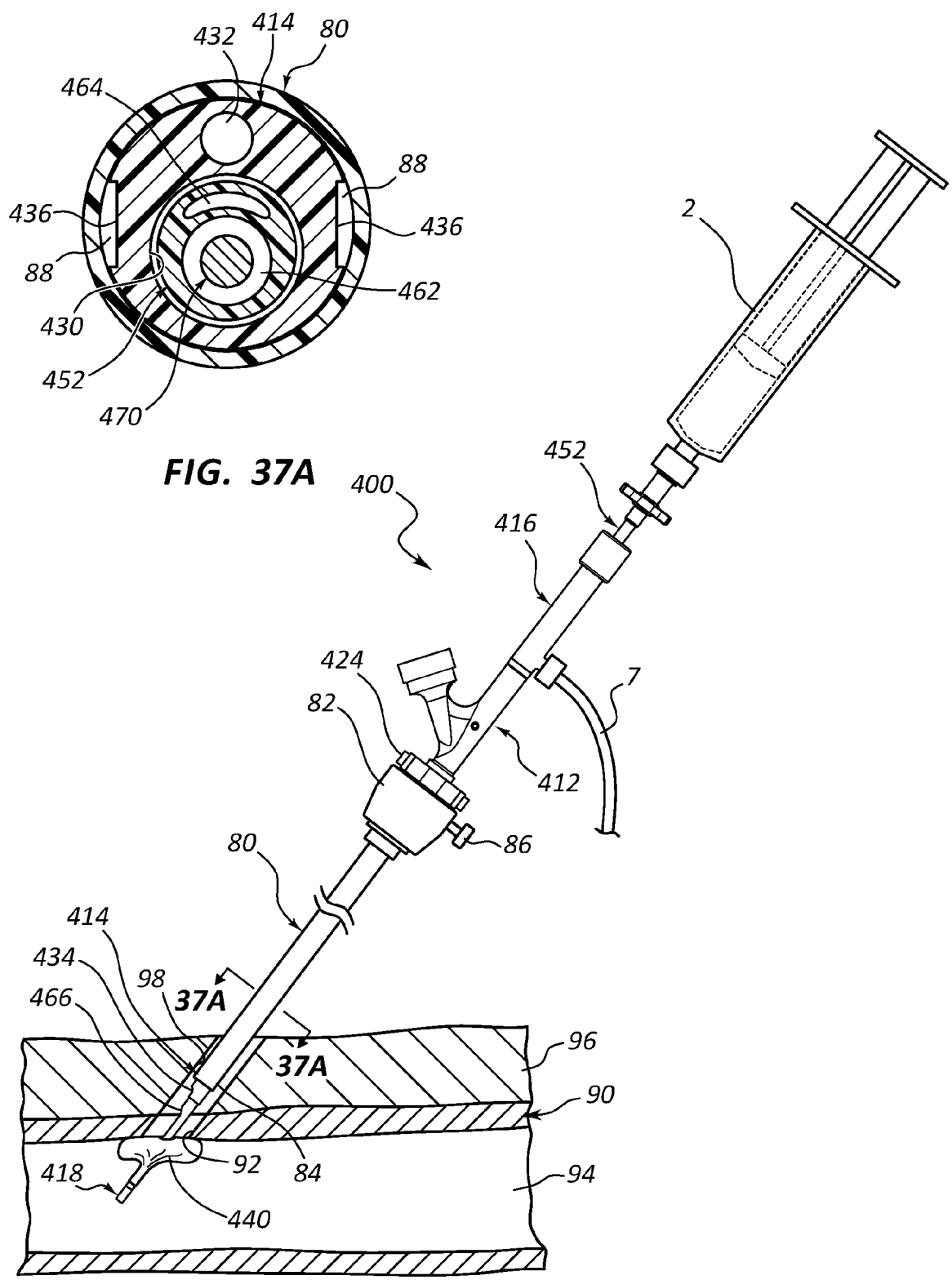

FIG. 37 shows the vascular closure device 400 inserted through the sheath 80 to position balloon 440 within vessel lumen 94. A volume of inflation fluid may be delivered via inflation fluid source 7 to inflate balloon 440. A vascular closure device 400 and sheath 80 may be withdrawn to contact the inflated balloon 440 against an inner surface of the vessel 90 to at least temporarily occlude blood flow through vessel puncture 92. The area in and around vessel puncture 92 may be aspirated via an aspiration lumen 88 and aspiration port 86 as shown in FIGS. 37 and 37A. The cutouts 436 in an outer surface of delivery tube 414 may provide an increased size for the aspiration lumen 88. The aspiration lumen 88 and aspiration port 86 may be used as part of a blood flashback feature of the vascular closure device 400 and sheath 80 to provide a visual indicator to the operator of a position of the distal portions of the vascular closure device 400 and sheath 80 relative to vessel lumen 94.

Figure 38:
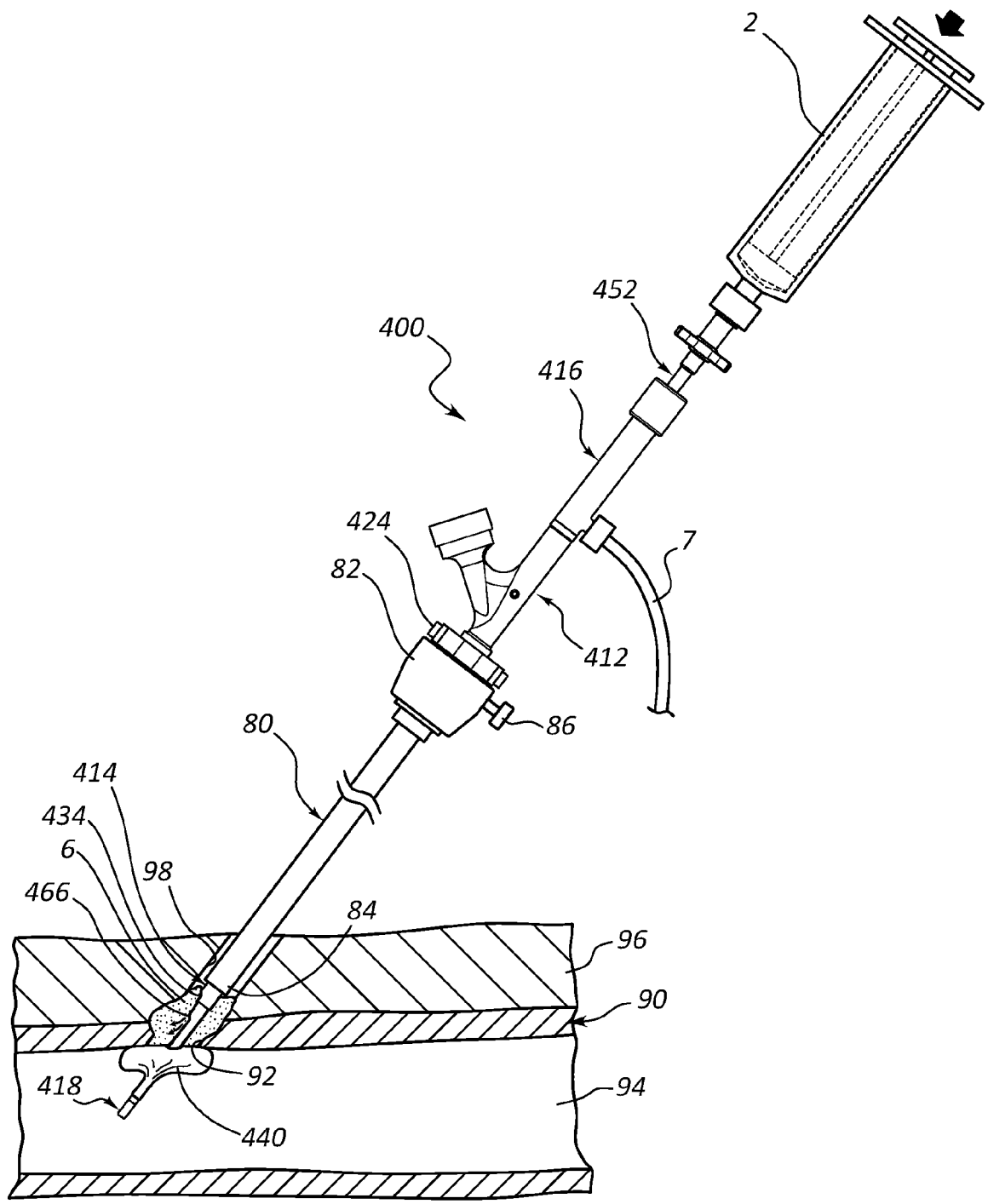

FIG. 38 shows the first bioadhesive carrier 2 operated to deliver a first volume of bioadhesive to the vessel puncture 92. The first volume of bioadhesive may travel through the second lumen 464 of inner tube 452 and out of the distal opening 466 as shown in FIG. 38. The first volume of bioadhesive may cure to form a first bioadhesive plug 6. The first bioadhesive plug 6 may be configured and sized to occlude blow flow through vessel puncture 92. The first bioadhesive plug 6 may cure to a solid or semi-solid state that limits distal movement of the first bioadhesive plug 6 into the vessel lumen 94 after deflating balloon 440.

Figure 39:
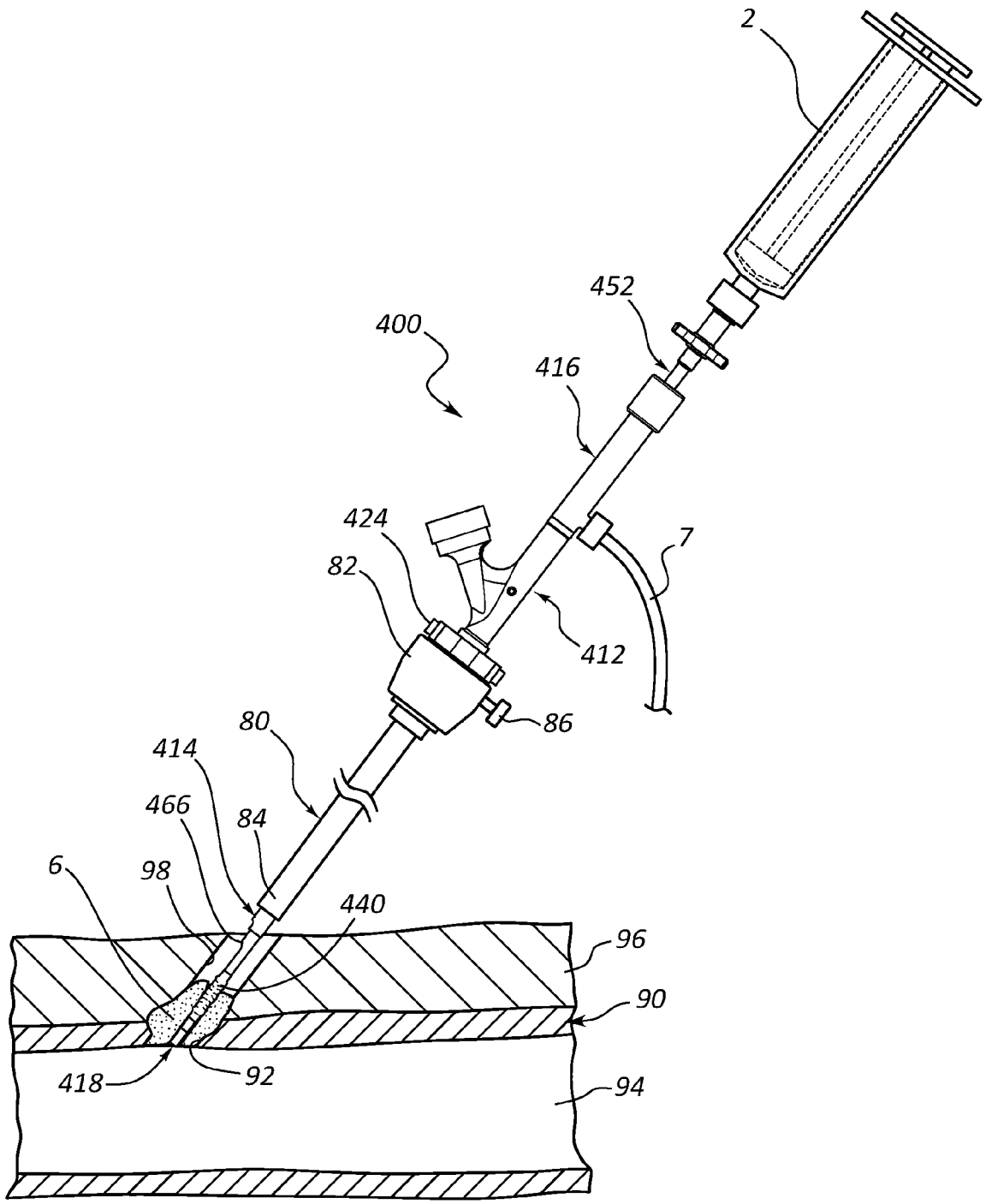

FIG. 39 shows balloon 440 deflated and the vascular closure device 400 and sheath 80 withdrawn further to position detachable sealing tip 418 within channel 9 of the first bioadhesive plug 6. The vascular closure device 400 may be operated to detach the detachable sealing tip 418 from the balloon location device 416. The detachable sealing tip 418 may occlude blood flow through channel 9. A second volume of bioadhesive may be delivered to the tissue tract 98 in a further sealing step.

Figure 40:
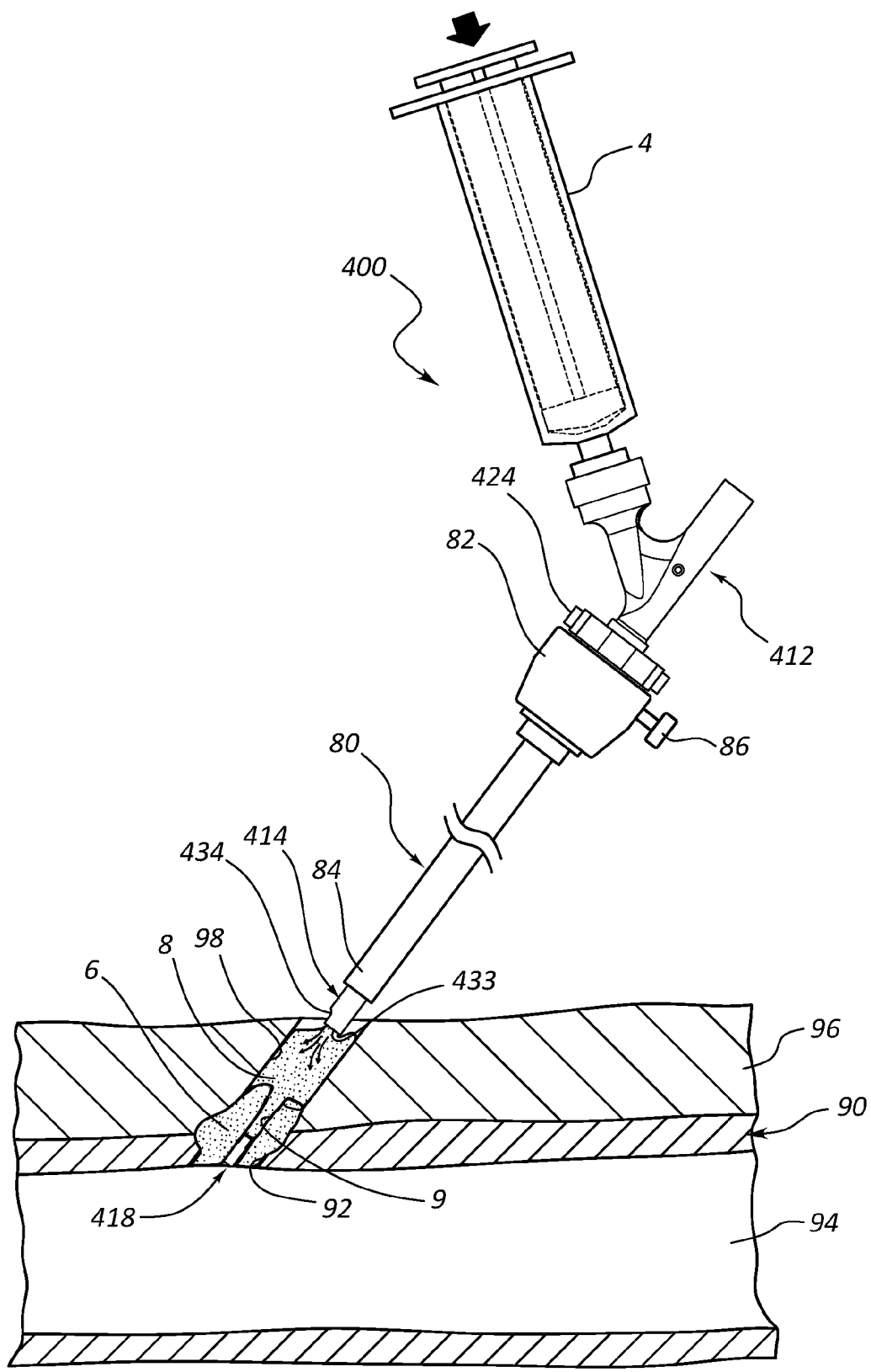
Figure 41:
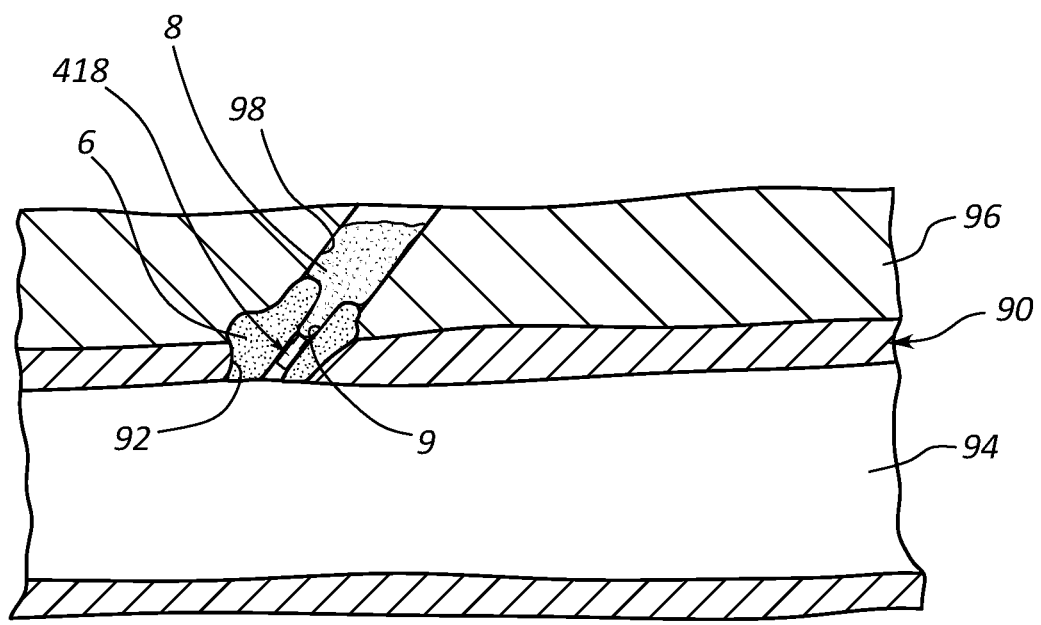

FIG. 40 shows the balloon location device 416 removed from the bioadhesive delivery device 411. A second bioadhesive carrier 4 is connected in flow communication with second lumen 432 of delivery tube 414. The second bioadhesive carrier 4 may be mounted to the injection port 422. The second bioadhesive carrier 4 is operated to deliver a second volume of bioadhesive through the second lumen 432, through the pass through channel 435, into the first lumen 430, out of delivery tube 414, and into the tissue tract 98 via the distal opening 433. A portion of the second volume of bioadhesive may flow into channel 9. The second volume of bioadhesive may cure to form a second bioadhesive plug 8. FIG. 41 shows the second bioadhesive plug 8 further sealing the tissue tract 98, channel 9 and vessel puncture 92 generally.

In other arrangements, when the distal opening 434 of second lumen 432 is not plugged with a backflow plug 5 as described above, the second volume of bioadhesive may flow through the second lumen 432 and distal opening 434 directly into the tissue tract 98 rather than passing through the pass through channel 435 or otherwise traveling through a portion of first lumen 430 or any other opening or lumen to reach the tissue tract 98.

The above-described examples with reference to FIGS. 1-41 describe and illustrate only some of the various options available for delivering two separate volumes of bioadhesive to a vessel puncture. A vascular closure device may include multiple features including a plurality of different lumens for delivering the volumes of bioadhesive. In some examples, more than two separate volumes of bioadhesive may be delivered to the vessel puncture. The volumes of bioadhesive may be delivered in sequence with a time delay between delivery. Providing separate lumens for delivering the separate volumes of bioadhesive may be particular relevant when using fast-setting bioadhesives. Fast-setting bioadhesives typically set up and clog a lumen through which it is delivered within in a few seconds or minutes after delivery. As such, separate lumens are typically required if attempting to deliver separate volumes of bioadhesive at spaced-apart times (e.g., a first volume to initially seal a vessel puncture when a balloon is used as a backstop with the vessel, and a second volume of bioadhesive after removing the balloon through the deposited first volume of bioadhesive), wherein the time spacing is greater than a minimum or threshold curing time.

The bioadhesives discussed herein may comprise a single component, or may comprise multiple sealant components that are mixed together. The multiple sealant components may further react together to form a cross-linked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical cross-linking. The sealant components may be cross-linked by any known method including, for example, condensation reactions, Michael addition, and free radical. Functional groups used for cross-linking may include, for example, thiols, acrylates, amines, succinimydyls and aldehydes, to name a few.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention.

What is claimed is:

1. A vascular closure system, comprising:
    a balloon location device having a balloon for temporarily sealing a vessel puncture internally, the balloon location device comprising a first lumen for delivering inflation fluid to the balloon and a second lumen for delivering a first volume of bioadhesive to the vessel puncture;
    a bioadhesive delivery device having a first lumen for delivery of the balloon location device to the vessel puncture and a second volume of bioadhesive to the vessel puncture;
    a sealing tip carried by the balloon location device at a location distal of the balloon and being releasable within a channel formed in the first volume of bioadhesive upon withdrawal of the balloon;
    a hypotube positioned in the first lumen of the bioadhesive delivery device, the hypotube having a hypotube lumen and a flared distal end, the balloon location device extending through the hypotube lumen, the flared distal end being movable between a first position blocking the first lumen of the bioadhesive delivery device to block backflow of the first bioadhesive into the first lumen of the bioadhesive delivery device and a second position not blocking the first lumen of the bioadhesive delivery device;
    wherein the second volume of bioadhesive is deliverable to the vessel puncture through the first lumen of the bioadhesive delivery device after the sealing tip is released in the channel.

2. The vascular closure system of claim 1, further comprising a core wire extending through the first lumen of the balloon location device.

3. The vascular closure system of claim 2, wherein the core wire is connected to the sealing tip and operable to release the sealing tip in the channel.

4. The vascular closure system of claim 1, wherein the flared distal end of the hypotube blocks backflow of the first volume of bioadhesive into a space between the first lumen of the bioadhesive delivery device and an outer surface of the hypotube when in the first position, and the hypotube is configured to advance distally to position the flared distal end out of the first lumen of the bioadhesive delivery device in the second position after delivery of the first volume of bioadhesive to permit delivery of the second volume of bioadhesive through the first lumen of the bioadhesive delivery device.

5. The vascular closure system of claim 1, wherein the flared distal end maintains a constant shape.

6. The vascular closure system of claim 1, wherein the flared distal end maintains a constant size.

7. A vascular closure device, comprising:
    a bioadhesive delivery device having at least one lumen;
    a balloon location device having a balloon carried at a distal end thereof and at least one lumen, the balloon location device being insertable through the at least one lumen of the bioadhesive delivery device to position the balloon through a vessel puncture, the balloon being expandable to temporarily seal the vessel puncture internally;

a hypotube positioned in the at least one lumen of the bioadhesive delivery device, the hypotube having a hypotube lumen and a flared distal end, the balloon location device being insertable through the hypotube lumen to position the balloon through a vessel puncture, and the hypotube being adjustable between a first position having the flared distal end blocking the at least one lumen of the bioadhesive delivery device and being arranged between the bioadhesive delivery device and the balloon location device and a second position outside of the bioadhesive delivery device and not blocking the at least one lumen of the bioadhesive delivery device;

wherein one of the bioadhesive delivery device and the balloon location device is configured for delivery of a first volume of bioadhesive to the vessel puncture through one of the at least one lumens, and one of the bioadhesive delivery device and the balloon location device is configured for delivery of a second volume of bioadhesive to the vessel puncture through another of the at least one lumens.

8. The vascular closure device of claim 7, wherein the at least one lumen of the balloon location device is configured for delivery of the first volume of bioadhesive and the at least one lumen of the bioadhesive delivery device is configured for delivery of the second volume of bioadhesive after delivery of the first volume of bioadhesive and after removal of the balloon location device.

9. The vascular closure device of claim 7, wherein the at least one lumen of the balloon location device includes first and second lumens, the first lumen being configured for delivery of inflation fluid to the balloon, and the second lumen being configured for delivery of the first volume of bioadhesive.

10. The vascular closure device of claim 7, wherein the second volume of bioadhesive is delivered between an outer surface of the hypotube and the at least one lumen of the bioadhesive delivery device.

11. The vascular closure device of claim 7, further comprising a sealing tip carried at a distal end of the balloon location device and configured to be deposited in a channel formed in the first volume of bioadhesive after removal of the balloon location device through the first volume of bioadhesive.

12. The vascular closure system of claim 7, wherein the flared distal end maintains a constant shape.

13. The vascular closure system of claim 7, wherein the flared distal end maintains a constant size.

* * * * *